United States Patent
Wang et al.

(10) Patent No.: US 10,172,824 B2
(45) Date of Patent: Jan. 8, 2019

(54) CRYSTAL FORMS OF SCUTELLARIN AGLYCONE AND PREPARATION THEREOF

(71) Applicants: YUNNAN INSTITUTE OF MATERIA MEDICA, Yunnan (CN); HLK Pharmaceuticals Co., Ltd., Guangdong Province (CN)

(72) Inventors: Zeren Wang, Guangdong Province (CN); Jun Xu, Guangdong Province (CN); Minghui Wang, Yunnan (CN); Zhaoyun Zhu, Yunnan (CN); Jingkun Wang, Yunnan (CN); Shuangxi Mei, Yunnan (CN); Wenqiang Sun, Yunnan (CN); Tao Cui, Yunnan (CN)

(73) Assignees: YUNNAN INSTITUTE OF MATERIA MEDICA, Yunnan (CN); HLK PHARMACEUTICALS CO., LTD., Guangdong Province (CN)

(*) Notice: Subject to any disclaimer, the term of this patent is extended or adjusted under 35 U.S.C. 154(b) by 0 days.

(21) Appl. No.: 15/535,609

(22) PCT Filed: Dec. 2, 2015

(86) PCT No.: PCT/CN2015/096208
§ 371 (c)(1),
(2) Date: Jun. 13, 2017

(87) PCT Pub. No.: WO2016/095702
PCT Pub. Date: Jun. 23, 2016

(65) Prior Publication Data
US 2017/0368019 A1    Dec. 28, 2017

(30) Foreign Application Priority Data
Dec. 15, 2014    (CN) .......................... 2014 1 0764911

(51) Int. Cl.
*C07D 311/30*    (2006.01)
*A61K 31/352*    (2006.01)

(52) U.S. Cl.
CPC .......... *A61K 31/352* (2013.01); *C07D 311/30* (2013.01)

(58) Field of Classification Search
CPC .......................... C07D 311/30; A61K 31/352
USPC .......................................... 549/403; 514/456
See application file for complete search history.

(56) References Cited

FOREIGN PATENT DOCUMENTS

| CN | 101434593 A | 5/2009 |
| CN | 101735291 A | 6/2010 |
| CN | 101824017 A | 9/2010 |
| CN | 102225958 A | 10/2011 |
| CN | 102618593 A | 8/2012 |
| CN | 103555784 A | 2/2014 |
| CN | 103570660 A | 2/2014 |
| CN | 104130230 A | 11/2014 |
| CN | 104592184 A | 5/2015 |

OTHER PUBLICATIONS

CN101824017A—Sep. 8, 2010, English Machine Translation.*
International Search Report of PCT/CN2015/096208 dated Mar. 7, 2016.
Office Action of CN Patent Application No. 201410764911.1 dated Jul. 12, 2016.
Abstract Translation of "Study of the Chemical COmposition of Scutellaria barbata D. Don," Chinese Tranditional and Herbal Drugs, 13:8:345-348 (1982).

* cited by examiner

*Primary Examiner* — Venkataraman Balasubramanian
(74) *Attorney, Agent, or Firm* — Abelman, Frayne & Schwab

(57) ABSTRACT

The invention belongs to the field of medicine and chemical industry, and particularly relates to multiple crystal forms of scutellarin aglycone and preparation thereof. The invention also relates to use of said crystal forms of scutellarin aglycone in the manufacture of a medicament for preventing and/or treating a cardiovascular or cerebrovascular disease, rheumatic arthritis or stroke sequelae, etc. The crystal forms of scutellarin aglycone according to the invention have good stability, and can solve the problems concerning poor oral absorption and low bioavailability of scutellarin.

7 Claims, 12 Drawing Sheets

CRYSTAL FORMS OF SCUTELLARIN AGLYCONE AND PREPARATION THEREOF

TECHNICAL FIELD

The invention belongs to the field of medicine and chemical industry, and particularly relates to multiple crystal forms of scutellarin aglycone and preparation thereof. The invention also relates to use of crystal forms of scutellarin aglycone in the manufacture of a medicament for preventing and/or treating a cardiovascular or cerebrovascular disease, rheumatic arthritis or stroke sequelae, etc.

BACKGROUND ART

Scutellarin is effective in improving cerebral blood circulation, enhancing cerebral blood flow, reducing blood viscosity, anti-platelet aggregation, and the like. Scutellarin is widely applied in clinical treatment, and is mainly applied to a cardiovascular or cerebrovascular disease, such as sequelae of paralysis caused by occlusive cerebrovascular disease, coronary heart disease, and angina pectoris. Scutellarin has a significant efficacy in the treatment of a cardiovascular or cerebrovascular disease, rheumatic arthritis, stroke sequelae and the like (Tang Yuping, Li Nianguang, Duan Jinao, Scutellarein derivative as well as preparation method and application thereof [P]. Jiangsu: CN101891728A, 2010-11-24.). In addition, breviscapine is also clinically useful in the treatment of a renal disease such as nephritic syndrome, diabetic nephropathy and chronic glomerulonephritis; a hepatic disease such as antituberculosis drug-induced liver injury, acute jaundice hepatitis, chronic hepatitis and refractory ascites due to cirrhosis; acute exacerbation of chronic obstructive pulmonary disease with hypoxemia; a diabetic chronic complication such as diabetic peripheral neuropathy and diabetic foot; an ocular disease such as commotio retinae, ischemic optic neuropathy, and ocular central serous chorioretinopathy; and a disease such as sudden deafness and fetal growth restriction (Sun Hua, Song Yi, Extending application of breviscapine in clinic [J]. ASIA-PACIFIC TRADITIONAL MEDICINE, 2013, 05:63-64.).

Since the purification process was not well-established previously, breviscapine is generally used as a crude drug in the clinical treatment of diseases. The problem concerning the administration of breviscapine resides in that breviscapine itself is a mixture of scutellarin, scutellarin isomer-isoscutellarin, and others, and has complex components, and therefore there are some difficulties in quality control. Scutellarin is the principal component breviscapine, and is resulted from technical development. However, scutellarin has a poor oral absorption, and a low oral availability.

Scutellarin aglycone is the hydrolysis product of scutellarin (Liu Jianming, Xiong Yuqing, Advances in studies on pharmacokinetics of scutellarin and scutellarein [J]. CHINA JOURNAL OF CHINESE MATERIA MEDICA, 2009, 24:3165-3168.), also called scutellarein, CAS NO. 529-53-3, with a molecular formula of $C_{15}H_{10}O_6$, and a molecular weight of 286.2.

With the development in purification and isolation techniques as well as detection techniques, in combination with the researches and discoveries on scutellarin and its aglycone, it has been found that scutellarin aglycone has a higher permeability in gastrointestinal tract than scutellarin, and has an oral absorption that is about 3-fold of that of scutellarin. Che Qingming et al., studied the intragastric administration of an equal amount of scutellarin aglycone and scutellarin to rats, respectively, and showed that oral administration of scutellarin aglycone facilitated absorption, and scutellarin aglycone was metabolically stable relative to scutellarin, and had a relative bioavailability of 301.8% (Chen Qingming, Chen Ying, Pan Liyi, He Hong, Scutellarein's pharmacokinetics in rats [J]. CHINESE JOURNAL OF NEW DRUGS, 2006, 18: 1557-1561.). Che Qingming et al. also found that after oral administration, seutellarin aglycone was mainly converted to the effective ingredient (i.e. scutellarin) of Erigeron breviscapus injection in vivo, and its blood distribution was close to that of Erigeron breviscapus injection (Chen Qingming, Pan Liyi, Chen Ying, He Hong, Study on Pharmacokinetics of Scutellarein in Rats [J], CHINESE PHARMACEUTICAL JOURNAL, 2007, 18: 1418-1421.). In other words, seutellarin aglycone almost has the same pharmacological activity as scutellarin. Lv et al. studied the pharmacokinetics of scutellarin liposomes in brain tissues, and based on the existing research results, it shows that scutellarin could cross the blood brain barrier and was distributed in brain tissues (Int J Pharm. 2005 Dec. 8: 306(1-2): 99-106. Distribution of liposomal breviscapine in brain following intravenous injection in rats. Lv W I, Guo J, Li J, Huang L, Ping Q.). When scutellarin aglycone was orally administered at a dose of 200 mg/kg, both scutellarin aglycone and scutellarin could be detected in rat plasma, while when scutellarin aglycone was orally administered at a dose of 20 mg/kg, only scutellarin was detected, and no crude drug was detected (Che Qingming, Chen Ying, Pan Liyi, He Hong, Study on bile excretion of scutellarein [J], CHINA JOURNAL OF CHINESE MATERIA MEDICA, 2006, 20: 1710-1712.). Ju Wenzheng et al. determined the blood concentration and the clinical pharmacokinetics of scutellarin; 360 mg scutellarin was orally administered to a subject, and blood was collected at 1, 3, 5, 8 h to determine the concentration of scutellarin: 20 ng/mL of scutellarin was determined only at 5 h, while a large amount of scutellarin aglycone was detected in plasma and urine, suggesting that scutellarin might be hydrolyzed to scutellarin aglycone in colon and then absorbed (Ju Wenzheng, Chu Jihong, Tan Renxiang, Xiang Ningning, Study on metabolites of scutellarin in gastrointestinal tract by UPLC-MS/MS method [J]. CHINESE JOURNAL OF CLINICAL PHARMACOLOGY AND THERAPEUTICS, 2006, 03: 292-295.).

Due to the poor oral absorption of scutellarin, the oral availability is low. However, scutellarin aglycone can be converted to scutellarin in vivo, and is superior to scutellarin in terms of oral absorption. If scutellarin aglycone can be obtained in its stable crystal forms, it will be more favorable for drug development and industrial production.

CONTENTS OF INVENTION

The invention prepared multiple crystal forms of scutellarin aglycone and a crystal form of scutellarin aglycone's ammonium salt by methods such as slow evaporation and crystallization, suspending and stirring, slow cooling, addition of anti-solvent, reverse addition of anti-solvent, liquid-solid gas-phase permeation, liquid-liquid gas-phase permeation, ionic liquid-induced crystallization, polymer-induced crystallization, humidity induction, wet grinding, and heating induction, and thereby accomplished the invention.

In an aspect, the invention relates to crystal form A of scutellarin aglycone, characterized in that said crystal form A has an X-ray powder diffraction pattern having main characteristic absorption peaks at least at about the following 2θ positions: 14.5±2°, 16.9±0.2°, 22.0±0.2°, 26.7±0.2° and 27.4±0.2°, as determined by using Cu—Kα radiation.

In one embodiment of the invention, the X-ray powder diffraction pattern of said crystal form A further has one or more characteristic absorption peaks at about 2θ position selected from: 11.2±0.2°, 13.8±0.2°, 20.4±0.2°, 24.8±0.2°, 28.7±0.2°, 30.4±0.2°, etc., as determined by using Cu—Kα radiation.

In a particular embodiment of the invention, the X-ray powder diffraction pattern of said crystal form A has the characteristic absorption peaks at about the following 2θ positions: 7.2±0.2°, 11.2±0.2°, 13.8±0.2°, 14.5±0.2°, 16.9±0.2°, 20.4±0.2°, 21.3±0.2°, 22.0±0.2°, 23.0±0.2°, 24.4±0.2°, 24.8±0.2°, 26.7±0.2°, 27.4±0.2°, 28.7±0.2°, 30.4±0.2°, 31.1±0.2°, 32.3±0.2°, 33.1±0.2°, 33.8±0.2°, 34.8±0.2° and 37.3±0.2°, as determined by using Cu—Kα radiation.

In a particular embodiment of the invention, its typical X-ray powder diffraction pattern is shown in FIG. 1.

The crystal form A according to any aspect of the invention has a melting point (onset temperature) in a range of 366.1±3.0° C. as determined by differential scanning calorimetry.

In a particular embodiment of the invention, it has a melting point of about 366.1° C. as determined by differential scanning calorimetry.

In a particular embodiment of the invention, its typical DSC thermogram is shown in FIG. 2.

The crystal form A according to any aspect of the invention, has a purity of ≥90%, preferably ≥95%.

The invention also relates to a method for preparing the crystal form A according to any aspect of the invention, comprising the following steps of:

(1) scutellarin is added with a water-miscible organic solvent (e.g., propylene glycol or ethylene glycol) having a reflux temperature of 120° C. to 220° C. (e.g., 180° C.), and heated to reflux, to completely dissolve scutellarin;

(2) the resultant solution of step (1) is dropwise added with an add (e.g., dilute hydrochloric acid or dilute sulfuric acid) solution, and further heated to reflex for 6-16 h;

(3) the resultant solution of step (2) is cooled to generate a precipitate and subjected to filtration to obtain a filter cake; the filter cake is washed with the reflux solvent (e.g., propylene glycol or ethylene glycol) in the step (1) and water respectively, and optionally is subjected to the step of drying or crushing, to obtain the crystal form A of scutellarin aglycone; and (4) optionally, scutellarin solid (including crystal form A, amorphous form or other crystal forms) is subjected to one or more of suspending and stirring, slow cooling, addition of anti-solvent reverse addition of anti-solvent, liquid-solid gas-phase permeation, ionic liquid-induced crystallization, humidity induction and wet grinding, to obtain the crystal form A.

In an embodiment of the invention, the method in said step (4) is selected from one of more of the following eight methods:

(1) to scutellarin aglycone solid (e.g., crystal form A), adding water or ethanol or acetic acid or acetonitrile or acetone or methyl isobutyl ketone or tetrahydrofuran or isopropyl acetate or methyl tert-butyl ether or 1,4-dioxane n-hexane or toluene or a mixed solvent of ethylene glycol/water or a mixed solvent of propylene glycol/water or a mixed solvent of PEG400/heptane or a mixed solvent of N-methylpyrrolidone/water or a mixed solvent of dimethyl sulfoxide/water or a mixed solvent of dimethylformamide/water, to obtain a suspension, stirring the suspension at room temperature (RT) or 40-60° C. (e.g., 50° C.) for 4-8 days (e.g., 6 days), and separating the solid by centrifugation to obtain the crystal form A;

(2) to scutellarin aglycone solid (e.g., crystal form A), adding a mixed solvent of dimethyl sulfoxide/ethanol or a mixed solvent of dimethyl sulfoxide/tetrahydrofuran or a mixed solvent of N-methylpyrrolidone/methyl tert-butyl ether or a mixed solvent of N-methylpyrrolidone/ethyl acetate or a mixed solvent of dimethylformamide/acetone or a mixed solvent of dimethylformamide/acetonitrile, equilibrating the resultant mixture at 40-60° C. (e.g., 50° C.) for a period of time (e.g., 30 min) and then cooling it for 2-5 days (e.g., 3 days) to 3-10° C. (e.g. 5° C.), stirring the suspension for 1-4 days (e.g., 2 days) at the temperature and separating the solid by centrifugation to obtain the crystal form A;

(3) to scutellarin aglycone solid (e.g., crystal form A), adding a solvent, to completely dissolve the solid, and then slowly adding an anti-solvent to the clear solution to generate a precipitate, and is optionally subjected to evaporation at room temperature to obtain a solid, wherein the precipitate or the solid obtained after evaporation is the crystal form A of scutellarin aglycone; the combination of a solvent and an anti-solvent may be N-methylpyrrolidone/water or dimethyl sulfoxide/methanol or dimethyl sulfoxide/acetone or dimethylformamide/water;

(4) to scutellarin aglycone solid (e.g., crystal form A), adding a solvent, to completely dissolve the solid, and then slowly adding the clear solution to an anti-solvent to generate a precipitate, and is optionally subjected to evaporation at room temperature to obtain a solid, wherein the precipitate or the solid obtained after evaporation at room temperature is the crystal form A of scutellarin aglycone; the combination of a solvent and an anti-solvent may be N-methylpyrrolidone/water or dimethyl sulfoxide/methanol or dimethyl sulfoxide/acetone or dimethylformamide/water;

(5) adding scutellarin aglycone solid (e g., crystal form A) to a bottle, and placing the bottle in a sealed glass bottle containing dichloromethane or ethanol or methanol or toluene or acetonitrile tetrahydrofuran or dimethylformamide or acetone, at room temperature in dark for a period of time (e.g., 13 days), wherein the solid obtained is the crystal form A;

(6) adding scutellarin aglycone solid (e.g., crystal form A) to a bottle, adding a mixed solvent of dimethyl sulfoxide/tetrahydrofuran or a mixed solvent of dimethylformamide/acetonitrile or a mixed solvent of dimethyl sulfoxide/ethanol, to obtain a clear solution, adding an ionic liquid to the clear solution, and evaporating the solvent in the resultant solution at room temperature slowly, to obtain the crystal form A; the ionic liquid, for example, refers to 1-butyl-3-methylimidazolium cation solution;

(7) adding scutellarin aglycone solid (e.g., crystal form A) to a bottle, and placing the bottle in a vessel at a constant humidity (e.g., 30%-99%, e.g., 2.8% or 57.6% or 75.3% or 97.3%), and storing it at room temperature for a period of time (e.g., 11 days), to obtain the crystal form A; and (8) adding scutellarin aglycone solid (e.g., crystal form A) in a mortar, adding isopropanol or acetic acid or acetonitrile or acetone or isopropyl acetate, and grinding the resultant mixture (e.g., 15 min) to obtain the crystal form A.

The invention further relates to crystal form D of scutellarin aglycone, characterized in that said crystal form D has an X-ray powder diffraction pattern having characteristic absorption peaks at least at about the following 2θ positions: 14.1±0.2°, 15.8±0.2°, 24.1±0.2°, 26.1±0.2°, 28.0±0.2°, as determined by using Cu—Kα radiation, In one embodiment of the invention, the X-ray powder diffraction pattern of said crystal form D further has one or more characteristic absorption peaks at about 2θ position selected from: 10.0±0.2°, 11.2±0.2°, 18.0±0.2°, 24.6±0.2°, 25.6±0.2°, 29.5±0.2°, 29.8±0.2°, etc., as determined by using Cu—Kα radiation.

In a particular embodiment of the invention, the X-ray powder diffraction pattern of said crystal form D has the characteristic absorption peaks at about the following 2θ positions: 7.0±0.2°, 9.9±0.2°, 11.1±0.2°, 14.1±0.2°, 15.7±0.2°, 18.0±0.2°, 19.9±0.2°, 21.2±0.2°, 22.4±0.2°, 24.1±0.2°, 24.6±0.2°, 25.2±0.2°, 25.5±0.2°, 26.0±0.2°, 27.9±0.2°, 29.4±0.2°, 29.8±0.2°, 30.9±0.2°, 31.8±0.2°, 35.0±0.2°, 36.8±0.2° and 38.6±0.2°, as determined by using Cu—Kα radiation.

In a particular embodiment of the invention, its typical X-ray powder diffraction pattern is shown in FIG. 7.

The crystal form D according to any aspect of the invention has a melting point of about 363.2±3.0° C., as determined by differential scanning calorimetry.

In a particular embodiment of the invention, it has a melting point of about 363.2° C. as determined by differential scanning calorimtry.

In a particular embodiment of the invention, its typical DSC thermogram is shown in FIG. 8.

The crystal form D according to any aspect of the invention has a purity of ≥90%, preferably ≥95%.

The invention further relates to a method for preparing the crystal form D according to any aspect of the invention, which is selected from one of the following seven methods:

(1) scutellarin aglycone solid (e.g., crystal form A) is added with a mixed solvent of pyridine-acetone (for example, at a volume ratio of 3:1) or of pyridine-heptane (for example, at a volume ratio of 3:1), and is completely dissolved to obtain a clear solution; the solvent is evaporated at room temperature slowly to dryness to obtain a solid, wherein the solid obtained after evaporation is the crystal form D of scutellarin aglycone;

(2) scutellarin aglycone solid (e.g., crystal form A) is added with pyridine and completely dissolved, then is added with ethanol slowly to generate a precipitate, and is optionally subjected to evaporation at room temperature to obtain a solid, wherein the precipitate or the solid obtained after evaporation is the crystal form D of scutellarin aglycone; alternatively, the crystal form D can be obtained by the same process in which dimethylformamide is used as a solvent, and tetrahydrofuran is used as an anti-solvent;

(3) scutellarin aglycone solid (e.g., crystal form A) is added with N-methylpyrrolidone and completely dissolved to generate a clear solution, and then the clear solution is added to acetonitrile slowly to generate a precipitate, and is optionally subjected to evaporation at room temperature to obtain a solid, wherein the precipitate or the solid obtained after evaporation is the crystal form D of scutellarin aglycone; alternatively, the crystal form D can be obtained by the same process in which pyridine is used as a solvent and ethanol is used as an anti-solvent, or when dimethylformamide is used as a solvent and tetrahydrofuran is used as an anti-solvent;

(4) scutellarin aglycone solid (e.g., crystal form A) is added with a mixed solvent of DMF/MEK (for example, at a volume ratio of 1:1) to obtain a clear solution, a mixed polymer is added to the clear solution, and the solvent is evaporated at room temperature slowly, to obtain the crystal form D of scutellarin aglycone;

(5) scutellarin aglycone solid (e.g., crystal form A) is dissolved in pyridine/ethyl acetate (for example, at a volume ratio of 3:1), and the solvent is evaporated at room temperature with the container's mouth open, to obtain the crystal form D of scutellarin aglycone;

(6) scutellarin aglycone solid (e.g., crystal form A) is added with acetone or acetonitrile to obtain a suspension, the suspension is stirred at room temperature (RT) and 40-60° C. (e.g., 50° C.) for 4-8 days (e.g., 6 days) to obtain a solid, and the resultant solid is separated by centrifugation to obtain a mixture of the crystal form A and crystal form D; and (7) scutellarin aglycone solid (e.g., crystal form A) is added with dimethylformamide and completely dissolved, then added with water slowly to generate a precipitate, and is optionally subjected to evaporation at room temperature to obtain a solid, wherein the precipitate or the solid obtained after evaporation is a mixture of the crystal form A and the crystal form D.

In an embodiment of the invention, the mixed polymer is a polymer prepared by mixing polyvinyl pyrrolidone (PVP), polyvinyl alcohol (PVA), polyvinyl acetate) (PVAc), polyvinyl chloride (PVC), hydroxypropyl methyl cellulose (HPMC) and methylcellulose (MC) at a mass ratio of 1:1:1:1:1:1.

The invention further relates to crystal form E of scutellarin aglycone, characterized in that said crystal form E has an X-ray powder diffraction pattern having main characteristic absorption peaks at least at about the following 2θ positions: 9.6±0.2°, 14.0±0.2°, 15.3±0.2°, 17.8±0.2° and 26.6±0.2°, as determined by using Cu—Kα radiation.

In one embodiment of the invention, the X-ray powder diffraction pattern of said crystal form E further has one or more characteristic absorption peaks at about 2θ position selected from: 10.2±0.2°, 10.9±0.2°, 16.1±0.2°, 19.3±0.2°, 21.2±0.2°, 28.5±0.2°, 29.8±0.2°, 31.1±0.2°, etc., as determined by using Cu—Kα radiation.

In a particular embodiment of the invention, the X-ray powder diffraction pattern of said crystal form E has the characteristic absorption peaks at about the following 2θ positions: 9.6±0.2°, 10.2±0.2°, 10.9±0.2°, 14.0±0.2°, 15.3±0.2°, 16.1±0.2°, 17.8±0.2°, 19.3±0.2°, 21.2±0.2°, 25.8±0.2°, 26.6±0.2°, 28.5±0.2°, 29.8±0.2° and 31.1±0.2°, as determined by using Cu—Kα radiation.

In a particular embodiment of the invention, its typical X-ray powder diffraction pattern is shown in FIG. 9.

The crystal form E according to any aspect of the invention, has a melting point of about 364.0±3.0° C. as determined by differential scanning calorimetry.

In a particular embodiment of the invention, it has a melting point of about 364.0° C. as determined by differential scanning calorimetry.

In a particular embodiment of the invention, its typical DSC thermogram is shown in FIG. 10.

The crystal form F according to any aspect of the invention, has a purity of ≥90%, preferably ≥95%.

The invention further relates to a method for preparing the crystal form E according to any aspect of the invention, comprising the following steps of:

heating scutellarin aglycone solid (e.g., crystal form A) to 250-350° C. (e.g., 300° C.), and then naturally cooling it to room temperature, to obtain the crystal form E of scutellarin aglycone.

The invention further relates to a crystal form of scutellarin aglycone's ammonium salt, characterized in that said crystal form has an X-ray powder diffraction pattern having main characteristic absorption peaks at least at about the following 2θ positions: 9.0±0.2°, 10.5±0.2°, 14.9±0.2°, 23.6±0.2° and 26.6°±0.2°, as determined by using Cu—Kα radiation.

In one embodiment of the invention, the X-ray powder diffraction pattern of said crystal form further has one or more characteristic absorption peaks at about 2θ position selected from: 6.4±0.2°, 12.8±0.2°, 13.8±0.2°, 15.3±0.2°, 22.7±0.2°, 25.7±0.2°, 27.7±0.2°, 29.1±0.2°, 32.0±0.2°, etc., as determined by using Cu—Kα radiation, In a particular embodiment of the invention, the X-ray powder diffraction pattern of said crystal form has the characteristic absorption peaks at about the following 2θ positions: 6.4±0.2°, 9.0±0.2°, 10.5±0.2°, 12.8±0.2°, 13.8±0.2°, 14.9±0.2°, 15.3±0.2°, 17.1±0.2°, 18.2±0.2°, 22.7±0.2°, 23.6±0.2°, 25.7±0.2°, 26.6±0.2°, 27.7±0.2°, 29.1±0.2°, 30.1±0.2°, 32.0±0.2°, 34.8±0.2° and 37.8±0.2°, as determined by using Cu—Kα, radiation.

In a particular embodiment of the invention, its X-ray powder diffraction pattern is shown in FIG. 19.

The crystal form of the ammonium salt according to any aspect of the invention is a hydrate.

The invention further relates to a method for preparing the crystal form of the ammonium salt according to any aspect of the invention, which is the method (1) or (2):

(1) to scutellarin aglycone solid (e.g., crystal form A), adding a certain volume of ammonia water, stirring the resultant mixture at room temperature, adding ammonia water to the initial volume when the volume of ammonia water decreases, and keeping stirring, wherein the crystal form of scutellarin aglycone's ammonium salt is obtained after 13-17 days (e.g., 15 days);

(2) to scutellarin aglycone solid (e.g., crystal form A), adding ammonia water, and adding acetone to obtain a suspension, stirring the suspension at room temperature for 4-8 days (e.g., 6 days), and separating the solid in the suspension by centrifugation to obtain a mixture of the crystal form of scutellarin aglycone's ammonium salt and the crystal form A of scutellarin aglycone.

The invention further relates to crystal form B of scutellarin aglycone, characterized in that said crystal form B has an X-ray powder diffraction pattern having main characteristic absorption peaks at least at about the following 2θ positions: 7.2±0.2°, 9.9±0.2°, 14.6±0.2°, 15.7±0.2° and 26.2±0.2°, as determined by using Cu—Kα radiation.

In one embodiment of the invention, the X-ray powder diffraction pattern of said crystal form B further has one or more characteristic absorption peaks at about 2θ position selected from: 11.2±0.2°, 14.1±0.2°, 18.9±0.2°, 20.8±0.2°, 25.0±0.2°, 28.0±0.2°, etc., as determined by using Cu—Kα radiation.

In a particular embodiment of the invention, the X-ray powder diffraction pattern of said crystal form B has the characteristic absorption peaks at about the following 2θ positions: 7.24±0.2°, 9.9±0.2°, 11.2±0.2°, 14.1±0.2°, 14.6±0.2°, 15.7±0.2°, 18.9±0.2°, 20.8±0.2°, 22.0±0.2°, 25.0±0.2°, 26.2±0.2°, 28.0±0.2° and 35.5±0.2°, as determined by using Cu—Kα radiation.

In a particular embodiment of the invention, its typical X-ray powder diffraction pattern is shown in FIG. 3.

The crystal form B according to any aspect of the invention, has a melting point of about 361.6±3.0° C. as determined by differential scanning calorimetry.

In particular embodiments of the invention, it has a melting point of about 361.6° C. as determined by differential scanning calorimetry.

In a particular embodiment of the invention, its DSC thermogram is shown in FIG. 4.

The crystal form B according to any aspect of the invention, has a purity of ≥90% preferably ≥95%.

The invention further relates to a method for preparing the crystal form B according to any aspect of the invention, which is the method (1) or (2) or (3):

(1) scutellarin aglycone solid (e.g., crystal form A) is added to a mixed solvent of pyridine-water (for example, at a volume ratio of 3:1) and completely dissolved to obtain a clear solution, and the resultant solution is subjected to evaporation at room temperature slowly, wherein the crystal form B of scutellarin aglycone is obtained after the solvent is evaporated to dryness;

(2) scutellarin aglycone solid (e.g., crystal form A) is added to a mixed solvent of pyridine-acetonitrile (for example, at a volume ratio of 3:1) and completely dissolved to obtain a dear solution, and the resultant solution is subjected to evaporation at room temperature slowly, wherein the crystal form B of scutellarin aglycone is obtained after the solvent is evaporated to dryness;

(3) scutellarin aglycone solid (e.g., crystal form A) is added to a mixed solvent of pyridine-ethyl acetate (for example, at a volume ratio of 3:1) and is completely dissolved to obtain a clear solution, and the resultant solution subjected to evaporation at room temperature slowly, wherein the form B of scutellarin aglycone is obtained after the solvent is evaporated to dryness.

The invention further relates to crystal form C of scutellarin aglycone characterized in that said crystal form C has an X-ray powder diffraction pattern having characteristic absorption peaks at least at about the following 2θ positions: 7.2±0.2°, 14.6±0.2°, 19.5±0.2°, 20.6±0.2° and 25.0±0.2°, as determined by using Cu—Kα radiation.

In one embodiment of the invention, the X-ray powder diffraction pattern of said crystal form C further has one or more characteristic absorption peaks at about 2θ position selected from: 9.2±0.2°, 16.4±0.2°, 16.9±0.2°, 17.7±0.2°, 18.2±0.2°, 18.9±0.2°, 21.5±0.2°, 22.0±0.2°, 22.8±0.2°, 25.7±0.2°, 27.0±0.2°, 27.7±0.2°, 28.7±0.2°, 29.3±0.2°, 32.4±0.2°, etc., as determined by using Cu—Kα radiation.

In a particular embodiment of the invention, the X-ray powder diffraction pattern of said crystal form C has the characteristic absorption peaks at about the following 2θ positions: 7.2±0.2°, 9.2±0.2°, 10.0±0.2°, 10.6±0.2°, 10.9±0.2°, 14.6±0.2°, 15.0±0.2°, 15.9±0.2°, 16.1±0.2°, 16.4±0.2°, 17.6±0.2°, 18.2±0.2°, 18.9±0.2°, 19.5±0.2°, 20.3±0.2°, 20.7±0.2°, 21.5±0.2°, 22.0±0.2°, 22.9±0.2°, 23.7±0.2°, 24.6±0.2°, 24.9±0.2°, 25.8±0.2°, 27.0±0.2°, 27.7±0.2°, 28.7±0.2°, 32.4±0.2°, 35.5±0.2° and 38.0±0.2°, as determined by using Cu—Kα radiation.

In a particular embodiment of the invention, its typical X-ray powder diffraction pattern is shown in FIG. 5.

The crystal form C according to any aspect of the invention, has a melting point of about 363.2±3.0° C. as determined by differential scanning calorimetry.

In a particular embodiment of the invention, it has a melting point of about 363.2° C. as determined by differential scanning calorimetry.

In a particular embodiment of the invention, its typical DSC thermogram is shown in FIG. 6.

The crystal form C according to any aspect of the invention, has a purity of ≥90%, preferably ≥95%.

The invention further relates to a method for preparing the crystal form C according to any aspect of the invention, which is the method (1) or (2):

(1) scutellarin aglycone solid (e.g., crystal form A) is added with pyridine and completely dissolved, then is added with heptane slowly to generate a precipitate, and is optionally subjected to evaporation at room temperature to obtain a solid, wherein the precipitate or the solid obtained after evaporation is the crystal form C of scutellarin aglycone;

(2) scutellarin aglycone solid (e.g., crystal form A) is added with pyridine and completely dissolved, and then slowly added to heptane tea generate a precipitate, and is optionally subjected to evaporation at room temperature to obtain a solid, wherein the precipitate or the solid obtained after evaporation is the crystal form C of scutellarin aglycone.

The invention further relates to crystal form F of scutellarin aglycone, characterized in that said crystal form F has an X-ray powder diffraction pattern having characteristic absorption peaks at least at about the following 2θ positions: 18.1±0.2°, 31.7±0.2° and 37.3±0.2°, as determined by using Cu—Kα radiation.

In a particular embodiment of the invention, the X-ray powder diffraction pattern of said crystal form F has the characteristic absorption peaks at about the following 2θ positions: 18.1±0.2°, 18.3±0.2°, 31.7±0.2° and 37.3±0.2°, as determined by using Cu—Kα radiation.

In a particular embodiment of the invention, its typical X-ray powder diffraction pattern is shown in FIG. 11.

The crystal form F according to any aspect of the invention, has a melting point of about 328.4±3.0° C. as determined by differential scanning calorimetry, In a particular embodiment of the invention, it has a melting point of about 328.4° C. as determined by differential scanning calorimetry.

In a particular embodiment of the invention, its typical DSC thermogram is shown in FIG. 12.

The invention further relates to a method for preparing the crystal form F according to any aspect of the invention, comprising the following steps of;

to scutellarin aglycone solid (e.g., crystal form A), adding n-hexane or toluene to obtain a suspension, stirring the suspension at room temperature (RT) and 40-60'C. (e.g., 50° C.) for 4-8 days (e.g., 6 days), and separating the solid in the suspension by centrifugation to obtain a mixture of the crystal form A and the crystal form F.

The invention further relates to crystal form G of scutellarin aglycone, characterized in that said crystal form G has an X-ray powder diffraction pattern having main characteristic absorption peaks at least at about the following 2θ positions: 8.3±0.2°, 14.3±0.2°, 18.2±0.2°, 20.7±0.2° and 23.6±0.2°, as determined by using Cu—Kα radiation.

In one embodiment of the invention, the X-ray powder diffraction pattern of said crystal form C further has one or more characteristic absorption peaks at about 2θ position selected from: 7.2±0.2°, 10.9±0.2°, 15.8±0.2°, 16.7±0.2°, 22.4±0.2°, 24.8±0.2°, 25.7±0.2°, 27.7±0.2°, etc., as determined by using Cu—Kα radiation.

In a particular embodiment of the invention, the X-ray powder diffraction pattern of said crystal form G has the characteristic absorption peaks at about the following 2θ positions: 6.8±0.2°, 7.2±0.2°, 8.3±0.2°, 9.9±0.2°, 10.9±0.2°, 14.2±0.2°, 15.8±0.2°, 16.7±0.2°, 18.2±0.2°, 20.4±0.2°, 20.7±0.2°, 21.9±0.2°, 22.3±0.2°, 23.6±0.2°, 24.8±0.2°, 25.7±0.2°, 27.7±0.2°, 28.9±0.2°, 30.9±0.2°, 32.2±0.2° and 37.7±0.2°, as determined by using Cu—Kα radiation.

In a particular embodiment of the invention, its typical X-ray powder diffraction pattern is shown in FIG. 13.

The crystal form according to any aspect of the invention, has a melting point of about 358.8±3.0° C. as determined by differential scanning calorimetry.

In a particular embodiment of the invention, it has a melting point of about 358.8° C. as determined by differential scanning calorimetry.

In a particular embodiment of the invention, its typical DSC thermogram is shown in FIG. 14.

The crystal form C according to any aspect of the invention, has a purity of ≥90%, preferably ≥95%.

The invention further relates to a method for preparing the crystal form C according to any aspect of the invention, which is method (I) or method (2):

(1) scutellarin aglycone solid (e.g., crystal form A) is added with a mixed solvent of pyridine/heptane (for example, at a volume ratio of 1:1) to obtain a clear solution, which is added with a mixed polymer and subjected to evaporation at room temperature slowly, to obtain the crystal form C of scutellarin aglycone;

(2) scutellarin aglycone solid (e.g., crystal form A) is added with pyridine/methanol (for example, at a volume ratio of 3:1) or pyridine/1,4-dioxane (for example, at a volume ratio of 3:1) or pyridine/methyl tert-butyl ether (for example, at a volume ratio of 3:1) or pyridine/2-methyl tetrahydrofuran (for example, at a volume ratio of 3:1) or pyridine/toluene (for example, at a volume ratio of 3:1) or pyridine, to obtain a clear solution, which is added with a mixed polymer and subjected to evaporation at room temperature slowly, to obtain the crystal form G of scutellarin aglycone.

In the embodiments of the invention, the mixed polymer refers to a polymer prepared by mixing polyvinyl pyrrolidone (PVP), polyvinyl alcohol (PVA), poly(vinyl acetate) (PVAc), polyvinyl chloride (PVC), hydroxypropyl methyl cellulose (HPMC) and methylcellulose (MC) at a mass ratio of 1:1:1:1:1:1.

The invention further relates to crystal form H scutellarin aglycone, characterized in that said crystal form H has an X-ray powder diffraction pattern having characteristic absorption peaks at least at about the following 2θ positions: 7.4±0.2°, 14.8±0.2°, 19.1±0.2°, 21.0+0.2° and 25.0±0.2°, as determined by using Cu—Kα radiation.

In one embodiment of the invention, the X-ray powder diffraction pattern of said crystal form H further has one or more characteristic absorption peaks at about 2θ position selected from: 10.1±0.2°, 10.9±0.2°, 11.5±0.2°, 16.2±0.2°, 19.8±0.2°, 22.2±0.2°, 23.2±0.2°, 27.7±0.2°, 29.0±0.2° etc., as determined by using Cu—Kα radiation.

In a particular embodiment of the invention, the X-ray powder diffraction pattern of said crystal form H has the characteristic absorption peaks at about the following 2θ positions: 7.4±0.2°, 10.1+0.2°, 10.9±0.2°, 11.5±0.2°, 13.7±0.2°, 14.8±0.2°, 15.7±0.2°, 16.2±0.2°, 17.2±0.2°, 18.6±0.2°, 19.1±0.2°, 19.8±0.2°, 20.2±0.2°, 21.0±0.2°, 21.7±0.2°, 22.2±0.2°, 23.2±0.2°, 23.9±0.2°, 25.0±0.2°, 25.5±0.2° and 26.0±0.2° as determined by using Cu—Kα radiation.

In a particular embodiment of the invention, its typical X-ray powder diffraction pattern is shown in FIG. 15.

The crystal form H according to any aspect of the invention, has a melting point of about 364.4±3.0° C. as determined by differential scanning calorimtry.

In a particular embodiment of the invention, it has a melting point of about 364.4° C. as determined by differential scanning calorimtry.

In a particular embodiment of the invention, its typical DSC thermogram is shown in FIG. 16.

The invention further relates to a method for preparing the crystal form. H according to any aspect of the invention, comprising the following steps of:

dissolving scutellarin aglycone solid (e.g., crystal form A) in a mixed solvent of pyridine/ethyl acetate (for example, at a volume ratio of 3:1), and evaporating the solvent in the resultant solution at room temperature, to obtain the crystal form D; dissolving the obtained crystal form D in pyridine/ethyl acetate (for example, at a volume ratio of 3:1), and evaporating the solvent in the resultant solution at room temperature, to obtain the crystal form H.

The invention further relates to crystal form I of scutellarin aglycone, characterized in that said crystal form I has an X-ray powder diffraction pattern having main characteristic absorption peaks at least at about the following 2θ positions: 6.9±0.2°, 15.6±0.2°, 19.9±0.2°, 22.3±0.2° and 26.8±0.2°, as determined by using Cu—Kα radiation.

In one embodiment of the invention, the X-ray powder diffraction pattern of said crystal form I further has one or more characteristic absorption peaks at about 2θ position selected from: 21.0±0.2°, 25.8±0.2°, 26.3±0.2°, etc., as determined by using Cu—Kα radiation.

In one embodiment of the invention, the X-ray powder diffraction pattern of said crystal form I has the characteristic absorption peaks at about the following 2θ positions: 6.6±0.2°, 6.9±0.2°, 7.0±0.2°, 12.8±0.2°, 14.0±0.2°, 15.6±0.2°, 15.7±0.2°, 17.0±0.2°, 19.0±0.2°, 19.9±0.2°, 21.0±0.2°, 21.7±0.2°, 22.0±0.2°, 22.3±0.2°, 23.2±0.2°, 25.8±0.2°, 26.3±0.2°, 26.8±0.2°, 27.7±0.2°, 28.2±0.2° and 29.0±0.2°, as determined by using Cu—Kα radiation.

In a particular embodiment of the invention, its typical X-ray powder diffraction pattern is shown in FIG. 17.

The crystal form I according to any aspect of the invention, has a melting point of about 362.1±3.0° C. as determined by differential scanning calorimetry.

In a particular embodiment of the invention, it has a melting point of about 362.1° C. as determined by differential scanning calorimetry, In a particular embodiment of the invention, its typical DSC thermogram is shown in FIG. 18.

The invention further relates to a method for preparing the crystal form I according to any aspect of the invention, comprising the following steps:

dissolving scutellarin aglycone solid (e.g., crystal form A) in a mixed solvent of pyridine/ethyl acetate (for example, at a volume ratio of 3:1), and evaporating the solvent in the resultant solution at room temperature, to obtain the crystal form I.

The invention further relates to the crystal form A, crystal form D, crystal form E, or crystal form F according to any aspect of the invention, which is an anhydrous substance.

The invention further relates to the crystal form B, crystal form C, crystal form G, crystal form H, or crystal form I according to any aspect of the invention, which is a solvate, a pyridine complex.

The invention further relates to a pharmaceutical composition, comprising at least one of the crystal form A, crystal form B, crystal form C, crystal form D, crystal form E, crystal form F, crystal form G, crystal form H, crystal form I, or the crystal form of the ammonium salt according to any aspect of the invention, and a pharmaceutically acceptable carrier or excipient.

The invention further relates to use of the crystal form A, crystal form B, crystal form C, crystal form D, crystal form F, crystal form F, crystal form G, crystal form H, crystal form I, or the crystal form of the ammonium salt according to any aspect of the invention in the manufacture of a medicament for prevention and/or treatment of a cardiovascular or cerebrovascular disease (e.g., sequelae of paralysis caused by occlusive cerebrovascular disease, coronary heart disease, angina pectoris), rheumatic arthritis, stroke sequelae, a renal disease such as nephritic syndrome, diabetic nephropathy and chronic glomerulonephritis, a hepatic disease such as antituberculosis drug-induced liver injury, acute jaundice hepatitis, chronic hepatitis and refractory ascites due to cirrhosis, acute exacerbation of chronic obstructive pulmonary disease with hypoxemia, a diabetic chronic complication such as diabetic peripheral neuropathy and diabetic foot, an ocular disease such as commotio retinae, ischemic optic neuropathy, and ocular central serous chorioretinopathy, a disease such as sudden deafness or fetal growth restriction.

The invention further relates to a method for preventing and/or treating a cardiovascular or cerebrovascular disease (e.g., sequelae of paralysis caused by occlusive cerebrovascular disease, coronary heart disease, angina pectoris), rheumatic arthritis, stroke sequelae, a renal disease such as nephritic syndrome, diabetic nephropathy and chronic glomerulonephritis, a hepatic disease such as antituberculosis drug-induced liver injury, acute jaundice hepatitis, chronic hepatitis and refractory ascites due to cirrhosis, acute exacerbation of chronic obstructive pulmonary disease with hypoxemia, a diabetic chronic complication such as diabetic peripheral neuropathy and diabetic foot, an ocular disease such as commotio retinae, ischemic optic neuropathy, and ocular central serous chorioretinopathy, a disease such as sudden deafness or fetal growth restriction, comprising the step of administering a prophylactically and/or therapeutically effective amount of the crystal form A, crystal form B, crystal form C, crystal form D, crystal form E, crystal form F, crystal form G, crystal form H, crystal form I, or the crystal form of the ammonium salt according to any aspect of the invention to a subject in need thereof.

In the invention, the subject is a mammal such as human.

The various crystal forms of scutellarin aglycone according to the invention can be used alone, or in combination with a pharmaceutically acceptable carrier or excipient in the form of a pharmaceutical composition. When used in the form of a pharmaceutical composition, a suitable administration form or dosage form is generally prepared from an effective amount of the crystal form of scutellarin aglycone, and one or more pharmaceutically acceptable carriers or excipients. The process involves mixing, granulating, compressing or dissolving the components by suitable means.

The pharmaceutical composition according to the invention may be administered by any of the following means: oral administration, spray inhalation, rectal administration, intranasal administration, vaginal administration, topical administration, parenteral administration such as subcutaneous, intravenous, intramuscular, intraperitoneal, intrathecal, intraventricular, intrasternal intracranial injection or input, or administration by virtue of an explant reservoir, wherein oral administration, muscular injection, intraperitoneal administration, or intravenous administration is preferred.

The pharmaceutically acceptable carrier comprised in the pharmaceutical composition of the invention includes, but is not limited to, ion exchanger, aluminum oxide, aluminum stearate, lecithin, serum protein such as human serum protein; buffer substance such as phosphate, glycerol, sorbic acid, potassium sorbate, a partial glyceride mixture of saturated plant fatty acid, water, salt or electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, lanocerin and the like. In a pharmaceutical composition, the carrier is present in an amount of 1%~98% by weight, generally of about 80% by weight. For the convenience of use, local anesthetics, preservatives, buffers and the like may be directly dissolved in the carrier.

Oral formulations such as oral tablets and capsules may comprise excipients such as binders, e.g., syrup, arabic gum, sorbitol, Astragalus gummifer, or polyvinylpyrrolidone; fillers, such as lactose, sucrose, corn starch, calcium phosphate, sorbitol, and aminoacetic acid; lubricants, such as magnesium stearate, talc, polyethylene glycol, and silica; disintegrants, such as potato starch; or acceptable lubrication-enhancing agents, such as sodium lauryl sulfate. The tablet may be coated by methods well known in pharmaceutics.

The pharmaceutical composition of the invention in an oral liquid form may be prepared into a suspension of water and oil, a solution, an emulsion, a syrup or an elixir, or into a dry product, which is supplemented with water or other suitable medium prior to use. The liquid formulation may comprise conventional additives such as suspending agent, sorbitol, methyl cellulose, glucose syrup, gel, hydroxyethyl cellulose, carboxymethyl cellulose, aluminum stearate gel, hydrogenated edible fat, emulsifier such as lecithin, sorbitan monooleate, gum arabic; or non-aqueous carrier (which may comprise edible oil), such as almond oil, fat such as glycerol, ethylene glycol or ethanol; preservative, such as methyl or propyl parahydroxybenzoate, sorbic acid. If necessary, a flavoring agent or a coloring agent may be added. Suppositories may comprise conventional suppository bases, such as cocoa butter or other glycerides. For parenteral administration, a liquid dosage form is generally prepared from a compound and at least one sterilized or aseptic carrier. The most preferred carrier is water. Depending on the selected carrier and the concentration of a drug, the compound may be dissolved in the carrier or be prepared into a suspension solution. When preparing a solution for use in injection, the compound is dissolved in water first, and is packaged into a seal bottle or an ampoule after filtration and sterilization.

When topically administered to skin, the compounds of the invention may be prepared in a suitable form of ointments, lotions or creams, wherein the active ingredient is suspended or dissolved in one or more carriers. The carriers for use in ointment preparations include, but are not limited to: mineral oil, liquid vaseline, white vaseline, propylene glycol, polyethylene oxide, polypropylene oxide, emulsifying wax and water; carriers for use in lotions and creams include, but are not limited to: mineral oil, sorbitan monostearate, Tween 60, hexadecylester wax, hexadecane aromatic alcohol, 2-octyl dodecanol, benzyl alcohol and water.

Depending on the administration route, the composition according to the invention may comprise an active ingredient in an amount of 0.1% by weight, or more suitably 10-60% by weight. However, when the composition is in a unit dosage form, each unit best comprises 50~500 mg active ingredient. Depending on the administration route and the administration frequency, a therapeutic dose suitable for an adult, for example, is 100-3000 mg per day, such as 1500 mg per day.

It has to be realized that the optimal administration dose and interval of the crystal forms of scutellarin aglycone depend on the severity of a disease or disorder, the properties of the compound, and the conditions such as administration form, route and site, and the particular mammal to be treated. The best administration dose can be determined by a physician.

The scutellarin aglycone provided in the invention has a formula of:

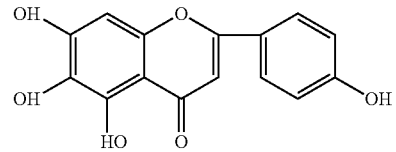 [SMILES: O=c1cc(-c2ccc(O)cc2)oc2cc(O)c(O)c(O)c12]

The chemical name of the compound is 5,6,7-trihydroxy-2-(4-hydroxyphenyl)-4H-benzopyran-4-one.

In the invention, the melting point refers to the onset temperature of melting in DSC test.

In the invention, the obtained crystal forms of scutellarin aglycone has a purity of ≥90% (weight percentage), e.g., ≥95% (weight percentage).

In the invention, the purity of a crystal form refers to, the content of said crystal form after removing for example the scutellarin aglycone in other crystal forms or amorphous form, as well as other impurity, which is measured by HPLC method.

In the invention, the position of the absorption peak in the X-ray powder diffraction pattern for each crystal form may be within the range of the disclosed value±0.2°, for example, within the range of the disclosed value±0.1°, and the melting point measured by differential scanning calorimetry may be within the range of the disclosed value±3.0° C.

In the invention, the expression "about a numerical value" refers to a range of 90%-110% of the numerical value, e.g., a range of 95%-105% of the numerical value.

It should be understood that when a different type of apparatus or a different test condition is used, a slightly different melting point may be read. The correct value for a crystal form depends on the purity of a compound, the weight of a sample, the heating rate, the particle size, as well as the checkout and maintenance of a test apparatus. The numerical value provided cannot be regarded as an absolute value.

It should be understood that when a different type of apparatus or a different test condition is used, a slightly different XRPD pattern and peak value may be obtained. The pattern, the peak value and the relative intensity of diffraction peak of a crystal form depend on the purity of a compound, the pretreatment of a sample, the scanning speed, the particle size, as well as the checkout and maintenance of a test apparatus. The numerical value provided cannot be regarded as an absolute value.

BENEFICIAL TECHNICAL EFFECTS OF THE INVENTION

Pharmacodynamic and pharmacokinetic studies show that after oral administration of scutellarin, the true absorption form in vivo is scutellarin aglycone (Fu Xiaozhong, Zhang Wei, Wang Yonglin, Lan Yanyu, Wang Aimin, Thou Wen, Huang Yong, Li Jing, Xing Fengjing, Liu Ying, Design, synthesis and anti-oxidative evaluation of 4'-L-amino add prodrugs of scutellarein [J]. Acta Pharmaceutica Sinica, 2011, 05: 548-555). Therefore, the use of scutellarin aglycone as a crude drug in the development of formulations has the advantages such as a good oral absorption and a higher bioavailability.

The invention prepares multiple crystal forms of scutellarin aglycone, which have a good stability and a high purity, and are suitable for development of new drugs and industrial production.

SPECIFIC MODES FOR CARRYING OUT THE INVENTION

The embodiments of the invention are illustrated in detail by reference to the following examples. However, it is understood by those skilled in the art that the examples are used only for the purpose of illustrating the invention, rather than limiting the protection scope of the invention. When the particular conditions are not indicated in Examples, it is carried out according to the conventional conditions or the conditions recommended by the manufacturer. When the manufacturers of reagents or devices used are not indicated, they are the conventional products that are commercially available.

Abbreviation:
XRPD-X ray powder diffraction (also called XRD)
TGA-Thermogravimetric Analysis
DSC-differential scanning calorimetry
RT-room temperature
GC-gas chromatography
HNMR-Proton Nuclear Magnetic Resonance Spectra Conditions for X-ray powder diffraction test:
XRPD patterns were collected in PANalytical Empyrean X-ray power diffractometer, the typical XRPD parameters are shown in Table 1.

TABLE 1

Conditions for X-ray powder diffraction test

| | Reflection parameters |
|---|---|
| X-ray | Cu, Kα, Kα1(Å): 1.540598; Kα 2 (Å): 1.544426 Kα2/Kα1 intensity ratio: 0.50 |
| X-ray tube setting | 45 kv, 40 mA |
| Divergence slit | automatic |
| Monochromator | none |
| Scanning pattern | continuous |
| Scan range (°2Theta) | 3°-40° |
| Step length of scanning (°2Theta) | 0.017 |
| Scan time (min) | 3'56" |

Conditions for TGA and DSC tests:
TGA and DSC are performed by TA Q500 TGA device and TA Q200 differential scanning calorimeter, and the typical parameters are listed in Table 2.

TABLE 2

Conditions for TGA and DSC tests

| | TGA | DSC |
|---|---|---|
| Specimen disc | Platinum disk, open wide | Aluminum disk, capped |
| Temperature range/° C. | RT-360° C. | RT-400° C. |
| Scan rate/° C./min | 10 | 10 |
| Protective gas | $N_2$ | $N_2$ |

A typical sample in the following examples refer to a crystal form sample with a good crystallinity, a high purity, little residual solvent and a definite melting point, which is selected from the crystal form sample prepared by a certain method.

EXAMPLE 1

Preparation of Crystal Form A of Scutellarin Aglycone 100 g scutellarin (purchased from Yunnan Plant Pharmaceutical Co., Ltd.) was weighed and put into a 5000 mL round-bottom flask, and 4000 mL propylene glycol or ethylene glycol was added. The resultant mixture was stirred and heated to reflux, and scutellarin was completely dissolved under reflux at the temperature. To the resultant solution, 5% hydrochloric acid solution (20 mL) was slowly added; after further reflux for 6-16 h, the hydrolysis reaction was accomplished. The solution was cooled, and a lot of precipitates appeared. After filtration, the filter cake was washed with propylene glycol or ethylene glycol, and water separately, and then dried and crushed to obtain the crystal form A of scutellarin aglycone, with a content (determined by HPLC) not less than 96%.

Figure 1:
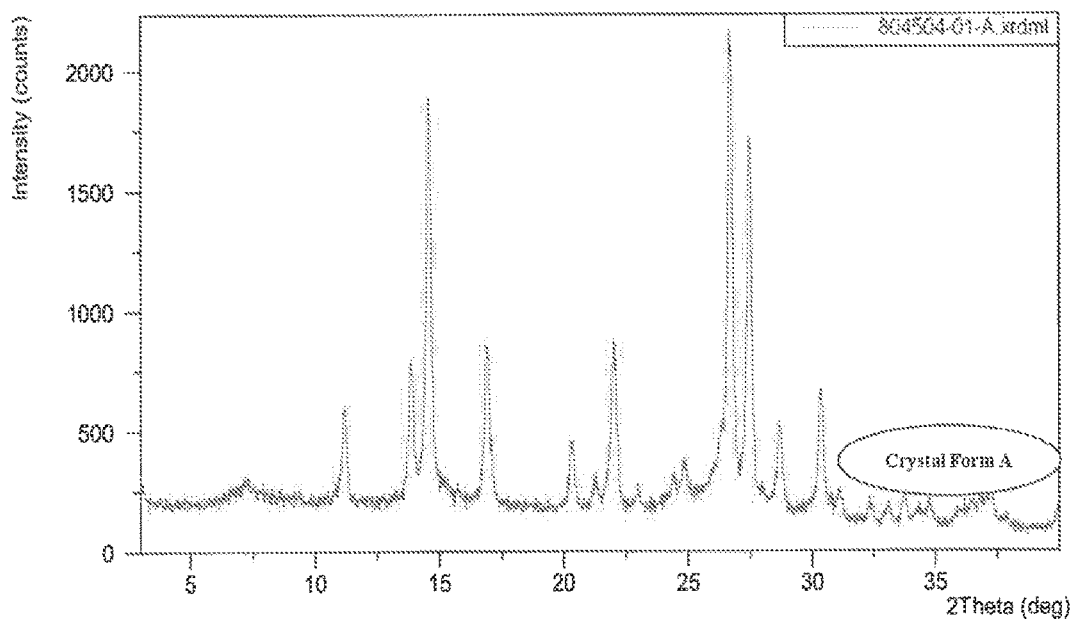
FIG. 1 shows the XRPD pattern of crystal form A of scutellarin aglycone.
Figure 2:
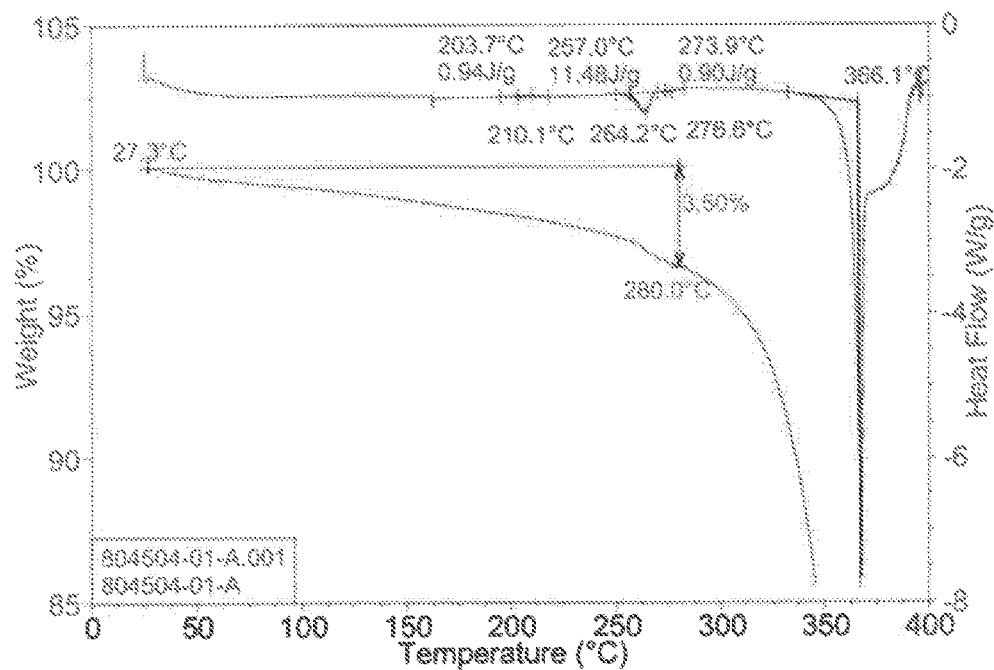
FIG. 2 shows the TGA and DSC thermograms of crystal form A of scutellarin aglycone.

The crystal form A prepared by the method has a typical XRPD pattern shown in FIG. 1, the peak information is shown in Table 3, and typical TGA and DSC thermograms are shown in FIG. 2. The melting point is 366.1° C. (it can be determined from DSC that the melting range is 366.1° C.-368.6° C.).

TABLE 3

XRPD peak information of crystal form A of scutellarin aglycone

| Pos. [°2Th.] | Height [cts] | d-spacing [Å] | Rel. Int. [%] |
|---|---|---|---|
| 7.22 | 74.6 | 12.24 | 4.1 |
| 11.20 | 382.3 | 7.90 | 20.8 |
| 13.82 | 535.8 | 6.41 | 29.2 |
| 14.53 | 1612.3 | 6.1 | 87.8 |
| 16.89 | 657.3 | 5.25 | 35.8 |
| 20.35 | 270.9 | 4.36 | 14.8 |
| 21.32 | 117.5 | 4.17 | 6.4 |
| 22.03 | 683.6 | 4.04 | 37.2 |
| 22.99 | 95.1 | 3.87 | 5.2 |
| 24.44 | 147.1 | 3.64 | 8.0 |
| 24.84 | 202.6 | 3.58 | 11.0 |
| 26.66 | 1836.2 | 3.34 | 100 |
| 27.42 | 1407.4 | 3.25 | 76.7 |
| 28.68 | 377.5 | 3.11 | 20.6 |
| 30.40 | 477.0 | 2.94 | 26.0 |
| 31.07 | 115.4 | 2.88 | 6.3 |
| 32.30 | 83.0 | 2.77 | 4.5 |
| 33.11 | 68.4 | 2.71 | 3.7 |
| 33.76 | 129.3 | 2.66 | 7.0 |
| 34.76 | 81.3 | 2.58 | 4.4 |
| 37.27 | 150.8 | 2.41 | 8.2 |

By methods such as suspending and stirring, slow cooling, addition of anti-solvent, reverse addition of anti-solvent, liquid-solid gas-phase permeation, ionic liquid-induced crystallization, humidity induction, and wet grinding, the crystal form A can also be obtained.

Method 1: about 15 mg sample of crystal form A was weighed at room temperature and added to a 1.5 mL glass bottle, and then 0.5 mL water or ethanol or acetic acid or acetonitrile or methyl isobutyl ketone or tetrahydrofuran or isopropyl acetate or methyl tert-butyl ether or 1,4-dioxane or a mixed solvent of ethylene glycol/water (for example, at a volume ratio of 1:1) or a mixed solvent of propylene glycol/water (for example, at a volume ratio of 1:1) or a mixed solvent of polyethylene glycol 400/heptane (for example, at a volume ratio of 1:1) or a mixed solvent of methylpyrrolidone/water (for example, at a volume ratio of 1:1) or a mixed solvent of methylpyrrolidone/water (for example, at a volume ratio of 1:1) or a mixed solvent of dimethyl sulfoxide/water (for example, at a volume ratio of 1:1) or a mixed solvent of dimethylformamide/water (for example, at a volume ratio of 1:1) was separately added to obtain a suspension. After magnetic stirring at room temperature (RT) for 6 days, the solid was separated by centrifugation. Alternatively, at 50° C., about 15 mg sample of crystal form A was weighed and added to a 1.5 mL glass bottle, and then 0.5 mL water or ethanol or acetic acid or acetone or methyl isobutyl ketone or tetrahydrofuran or isopropyl acetate or methyl tert-butyl ether or 1,4-dioxane or a mixed solvent of ethylene glycol/water (for example, at a volume ratio of 1:1) or a mixed solvent of propylene glycol/water (for example, at a volume ratio of 1:1) or a mixed solvent of polyethylene glycol 400/heptane (for example, at a volume ratio of 1:1) or a mixed solvent of methylpyrrolidone/water (for example, at a volume ratio of 1:1) or a mixed solvent of methylpyrrolidone/water (for example, at a volume ratio of 1:1) or a mixed solvent of dimethyl sulfoxide/water (for example, at a volume ratio of 1:1) or a mixed solvent of dimethylformamide/water (for example, at a volume ratio of 1:1) was separately added to obtain a suspension. After magnetic stirring for 6 days, the solid was separated by centrifugation to obtain the crystal form A.

Method 2: about 15 mg sample of crystal form A was weighed and added to a 1.5 mL glass bottle, and then 0.5 mL acetone was added to obtain a suspension. After magnetic stirring at room temperature for 6 days, the solid was separated by centrifugition. Alternatively, about 15 mg sample of crystal form A was weighed and added to a 1.5 mL glass bottle, and then 0.5 mL acetonitrile was added to obtain a suspension. After magnetic stirring at 50° C. for 6 days, the solid was separated by centrifugation. By the two methods, a mixed crystal of crystal form A and crystal form D can be obtained.

Acetone was added to obtain the crystal form A and crystal form D. The peak information is shown in Table 4.

TABLE 4

XRPD peak information of crystal form A and crystal form D of scutellarin aglycone

| Pos. [°2θ.] | Height [cts] | d-spacing [Å] | Rel. Int. [%] |
|---|---|---|---|
| 7.01 | 107.7 | 12.61 | 9.5 |
| 9.90 | 141.0 | 8.94 | 12.4 |
| 11.09 | 183.3 | 7.98 | 16.2 |
| 13.83 | 165.7 | 6.40 | 14.6 |
| 14.06 | 204.3 | 6.30 | 18.0 |
| 14.56 | 1135.2 | 6.08 | 100.0 |
| 15.72 | 577.2 | 5.64 | 50.9 |
| 16.88 | 227.7 | 5.25 | 20.1 |
| 17.98 | 108.2 | 4.93 | 9.5 |
| 19.91 | 79.2 | 4.46 | 7.0 |
| 21.93 | 189.7 | 4.05 | 16.7 |
| 26.06 | 55.7 | 3.42 | 4.9 |
| 26.69 | 77.8 | 3.34 | 6.9 |
| 27.45 | 67.3 | 3.25 | 5.9 |
| 27.95 | 54.2 | 3.19 | 4.8 |
| 29.37 | 26.3 | 3.04 | 2.3 |
| 30.33 | 42.2 | 2.95 | 3.7 |
| 31.83 | 54.0 | 2.81 | 4.8 |
| 34.36 | 26.8 | 2.61 | 2.4 |
| 37.07 | 85.2 | 2.43 | 7.5 |

Acetonitrile was added to obtain the crystal form A and crystal form D. The peak information is shown in Table 5.

TABLE 5

XRPD peak information of crystal form A and crsytal form D of scutellarin aglycone

| Pos. [°2Th.] | Height [cts] | d-spacing [Å] | Rel. Int. [%] |
|---|---|---|---|
| 6.96 | 66.9 | 12.70 | 7.9 |
| 9.92 | 68.3 | 8.92 | 8.0 |
| 11.16 | 138.2 | 7.93 | 16.2 |
| 13.83 | 193.1 | 6.40 | 22.7 |
| 14.54 | 852.2 | 6.09 | 100.0 |
| 15.67 | 225.0 | 5.66 | 26.4 |
| 16.89 | 212.1 | 5.25 | 24.9 |
| 17.95 | 43.1 | 4.94 | 5.1 |
| 20.32 | 62.7 | 4.37 | 7.4 |
| 21.93 | 139.6 | 4.05 | 16.4 |
| 23.98 | 36.0 | 3.71 | 4.1 |
| 26.03 | 127.5 | 3.42 | 15.0 |
| 26.68 | 282.1 | 3.34 | 33.1 |
| 27.44 | 235.1 | 3.25 | 27.6 |
| 28.00 | 78.2 | 3.19 | 9.2 |

TABLE 5-continued

XRPD peak information of crystal form A and crsytal form D of scutellarin aglycone

| Pos. [°2Th.] | Height [cts] | d-spacing [Å] | Rel. Int. [%] |
|---|---|---|---|
| 28.64 | 55.4 | 3.12 | 6.5 |
| 30.33 | 82.6 | 2.95 | 9.7 |
| 34.81 | 25.0 | 2.58 | 2.9 |
| 37.09 | 60.4 | 2.42 | 7.1 |

Method 3: about 15 mg sample of crystal form A was weighed and added to a 1.5 mL glass bottle, and then 0.5 mL hexane or toluene was added separately to obtain a suspensions. After magnetic stirring at room temperature or 50° C. for 6 days, the solid was separated by centrifugation to obtain a mixed crystal of the crystal form A and crystal form F.

Hexane was used as a solvent. After magnetic stirring at room temperature for 6 days, crystal form A and crystal form F were obtained. The peak information is shown in Table 6.

TABLE 6

XRPD peak information of crystal form A and crystal form F of scutellarin aglycone

| Pos. [°2Th.] | Height [cts] | d-spacing [Å] | Rel. Int. [%] |
|---|---|---|---|
| 7.13 | 33.6 | 12.40 | 1.3 |
| 11.25 | 517.1 | 7.86 | 20.5 |
| 13.92 | 655.5 | 6.36 | 26.0 |
| 14.64 | 1544.3 | 6.05 | 61.2 |
| 16.97 | 695.7 | 5.23 | 27.6 |
| 17.98 | 1368.4 | 4.93 | 54.2 |
| 18.09 | 1452.3 | 4.90 | 57.5 |
| 20.42 | 283.2 | 4.35 | 11.2 |
| 21.37 | 119.1 | 4.16 | 4.7 |
| 22.15 | 648.7 | 4.01 | 25.7 |
| 23.03 | 97.3 | 3.86 | 3.9 |
| 24.49 | 176.6 | 3.63 | 7.0 |
| 24.91 | 218.6 | 3.58 | 8.7 |
| 26.75 | 2525.5 | 3.33 | 100.0 |
| 27.51 | 1956.1 | 3.24 | 77.5 |
| 28.78 | 402.0 | 3.10 | 15.9 |
| 30.39 | 624.4 | 2.94 | 24.7 |
| 31.17 | 117.8 | 2.87 | 4.7 |
| 32.42 | 85.1 | 2.76 | 3.4 |
| 33.18 | 70.6 | 2.70 | 2.8 |
| 33.82 | 142.4 | 2.65 | 5.6 |
| 34.80 | 122.3 | 2.58 | 4.8 |
| 37.32 | 193.2 | 2.41 | 7.7 |

Toluene was used as a solvent After stirring at room temperature for 6 days, the crystal form A and crystal form F were obtained. The peak information is shown in Table 7.

TABLE 7

XRPD peak information of crystal form A and crystal form F of scutellarin aglycone

| Pos. [°2Th.] | Height [cts] | d-spacing [Å] | Rel. Int. [%] |
|---|---|---|---|
| 11.19 | 115.2 | 7.91 | 20.0 |
| 13.83 | 187.3 | 6.40 | 32.5 |
| 14.56 | 575.5 | 6.08 | 100.0 |
| 16.91 | 218.5 | 5.24 | 38.0 |
| 17.98 | 140.5 | 4.93 | 24.4 |
| 20.33 | 78.3 | 4.37 | 13.6 |
| 22.07 | 167.7 | 4.03 | 29.1 |
| 23.78 | 81.5 | 3.74 | 14.2 |
| 26.67 | 387.6 | 3.34 | 67.4 |
| 27.44 | 301.9 | 3.25 | 52.5 |
| 28.68 | 79.5 | 3.11 | 13.8 |

TABLE 7-continued

XRPD peak information of crystal form A and crystal form F of scutellarin aglycone

| Pos. [°2Th.] | Height [cts] | d-spacing [Å] | Rel. Int. [%] |
|---|---|---|---|
| 30.33 | 93.7 | 2.95 | 16.3 |
| 37.07 | 46.9 | 2.42 | 8.2 |

Hexane was used as a solvent. After magnetic stirring at 50° C. for 6 days the crystal form A and crystal form F were obtained. The peak information is shown in Table 8.

TABLE 8

XRPD peak information of crystal form A and crystal form F of scutellarin aglycone

| Pos. [°2Th.] | Height [cts] | d-spacing [Å] | Rel. Int. [%] |
|---|---|---|---|
| 11.16 | 87.2 | 7.93 | 9.5 |
| 13.84 | 141.7 | 6.40 | 15.4 |
| 14.54 | 541.4 | 6.09 | 59.0 |
| 16.89 | 198.8 | 5.25 | 21.7 |
| 17.96 | 918.0 | 4.94 | 100.0 |
| 20.29 | 49.6 | 4.38 | 5.4 |
| 21.96 | 94.4 | 4.05 | 10.3 |
| 26.69 | 200.4 | 3.34 | 21.8 |
| 27.43 | 156.2 | 3.25 | 17.0 |
| 28.65 | 36.5 | 3.12 | 4.0 |
| 30.30 | 51.6 | 2.95 | 5.6 |

Toluene was used as a solvent. After magnetic stirring at 50° C. for 6 days, the crystal form A and crystal form F were obtained. The peak information is shown in Table 9.

TABLE 9

XRPD peak information of crystal form A and crystal form F of scutellarin aglycone

| Pos. [°2Th.] | Height [cts] | d-spacing [Å] | Rel. Int. [%] |
|---|---|---|---|
| 14.66 | 29.2 | 6.04 | 19.1 |
| 18.05 | 153.1 | 4.92 | 100.0 |
| 22.11 | 34.0 | 4.02 | 22.2 |
| 26.74 | 116.0 | 3.33 | 75.8 |
| 27.50 | 90.1 | 3.24 | 58.9 |

Method 4: about 20 mg sample of crystal form A was weighed and added to 5 , and then 0.5 mL a mixed solvent of dimethyl sulfoxide/ethanol (for example, at a volume ratio of 1:5) or a mixed solvent of dimethyl sulfoxide/tetrahydrofuran (for example, at a volume ratio of 1:5) or a mixed solvent of methylpyrrolidone/methyl tert-butyl ether (for example, at a volume ratio of 1:5) or a mixed solvent of methylpyrrolidone/ethyl acetate (for example, at a volume ratio of 1:5) or a mixed solvent of dimethylformamide/acetone (for example, at a volume ratio of 1:5) or a mixed solvent of dimethylformamide/acetonitrile (for example, at a volume ratio of 1:5) was added separately. After equilibrating at 50° C. for 30 min, the temperature was cooled to 5° C. within three days. After suspending and stirring at 5° C. for 2 days the solid was separated by centrifugation to obtain the crystal form A.

Dimethyl sulfoxide/ethanol (for example, at a volume ratio of 1:5) was used as a solvent to obtain the crystal form A. The peak information is shown in Table 10.

TABLE 10

XRPD peak information of crystal form A of scutellarin aglycone

| Pos. [°2Th.] | Height [cts] | d-spacing [Å] | Rel. Int. [%] |
|---|---|---|---|
| 7.15 | 52.6 | 12.36 | 2.2 |
| 11.16 | 146.4 | 7.93 | 6.0 |
| 13.81 | 287.8 | 6.41 | 11.8 |
| 14.53 | 2439.5 | 6.10 | 100.0 |
| 16.88 | 387.3 | 5.25 | 15.9 |
| 20.37 | 55.4 | 4.36 | 2.3 |
| 21.93 | 285.7 | 4.05 | 11.7 |
| 26.68 | 212.8 | 3.34 | 8.7 |
| 27.43 | 192.5 | 3.25 | 7.9 |
| 28.71 | 39.8 | 3.11 | 1.6 |
| 30.28 | 69.8 | 2.95 | 2.9 |
| 34.32 | 51.6 | 2.61 | 2.1 |
| 37.02 | 118.0 | 2.43 | 4.8 |

Dimethyl sulfoxide/tetrahydrofuran (for example, at a volume ratio of 1:5) was used as a solvent to obtain the crystal form A. The peak information is shown in Table 11.

TABLE 11

XRPD peak information of crystal form A of scutellarin aglycone

| Pos. [°2Th.] | Height [cts] | d-spacing [Å] | Rel. Int. [%] |
|---|---|---|---|
| 11.23 | 155.7 | 7.88 | 5.0 |
| 13.91 | 385.6 | 6.37 | 12.4 |
| 14.62 | 3114.8 | 6.06 | 100.0 |
| 16.94 | 596.5 | 5.23 | 19.2 |
| 20.38 | 185.2 | 4.36 | 6.0 |
| 22.00 | 611.9 | 4.04 | 19.7 |
| 26.69 | 235.8 | 3.34 | 7.6 |
| 27.46 | 232.6 | 3.25 | 7.5 |
| 30.35 | 148.2 | 2.94 | 4.8 |
| 30.75 | 131.9 | 2.91 | 4.2 |
| 31.07 | 119.3 | 2.88 | 3.8 |
| 34.39 | 120.0 | 2.61 | 3.9 |
| 37.07 | 251.1 | 2.43 | 8.1 |

Methylpyrrolidone/methyl tert-butyl ether (for example, at a volume ratio of 1:5) was used as a solvent to obtain the crystal form A. The peak information is shown in Table 12.

TABLE 12

XRPD peak information of crystal form A of scutellarin aglycone

| Pos. [°2Th.] | Height [cts] | d-spacing [Å] | Rel. Int. [%] |
|---|---|---|---|
| 11.18 | 168.3 | 7.91 | 14.5 |
| 13.85 | 246.8 | 6.40 | 21.3 |
| 14.53 | 1158.1 | 6.10 | 100.0 |
| 16.89 | 369.9 | 5.25 | 31.9 |
| 20.41 | 100.5 | 4.35 | 8.7 |
| 22.09 | 265.2 | 4.02 | 22.9 |
| 23.04 | 32.6 | 3.86 | 2.8 |
| 24.89 | 54.4 | 3.58 | 4.7 |
| 26.65 | 523.9 | 3.35 | 45.2 |
| 27.45 | 532.6 | 3.25 | 46.0 |
| 28.68 | 139.1 | 3.11 | 12.0 |
| 30.33 | 201.6 | 2.95 | 17.4 |
| 31.13 | 77.5 | 2.87 | 6.7 |
| 32.40 | 32.5 | 2.76 | 2.8 |
| 33.80 | 47.2 | 2.65 | 4.1 |
| 34.55 | 36.7 | 2.60 | 3.2 |
| 37.15 | 126.5 | 2.42 | 10.9 |

Methylpyrrolidone/ethyl acetate (for example, at a volume ratio of 1:5) was used as a solvent to obtain the crystal form A. The peak information is shown in Table 13.

TABLE 13

XRPD peak information of crystal form A of scutellarin aglycone

| Pos. [°2Th.] | Height [cts] | d-spacing [Å] | Rel. Int. [%] |
|---|---|---|---|
| 7.24 | 60.5 | 12.20 | 4.2 |
| 11.19 | 141.4 | 7.90 | 9.7 |
| 13.84 | 222.7 | 6.40 | 15.4 |
| 14.56 | 1451.4 | 6.08 | 100.0 |
| 16.90 | 319.1 | 5.25 | 22.0 |
| 20.39 | 67.5 | 4.36 | 4.7 |
| 21.97 | 181.5 | 4.05 | 12.5 |
| 24.71 | 18.5 | 3.60 | 1.3 |
| 26.69 | 330.2 | 3.34 | 22.8 |
| 27.48 | 272.6 | 3.25 | 18.8 |
| 28.75 | 62.7 | 3.11 | 4.3 |
| 30.36 | 126.3 | 2.94 | 8.7 |
| 31.13 | 40.3 | 2.87 | 2.8 |
| 34.40 | 39.4 | 2.61 | 2.7 |
| 37.12 | 78.8 | 2.42 | 5.4 |

Dimethylformamide/acetone (for example, at a volume ratio of 1:5) was used as a solvent to obtain the crystal form A. The peak information is shown in Table 14.

TABLE 14

XRPD peak information of crystal form A of scutellarin aglycone

| Pos. [°2Th.] | Height [cts] | d-spacing [Å] | Rel. Int. [%] |
|---|---|---|---|
| 11.12 | 32.6 | 7.96 | 2.4 |
| 13.80 | 124.5 | 6.42 | 9.2 |
| 14.52 | 1347.7 | 6.10 | 100.0 |
| 16.86 | 192.0 | 5.26 | 14.3 |
| 21.92 | 137.3 | 4.05 | 10.2 |
| 26.65 | 35.6 | 3.34 | 2.6 |
| 27.40 | 46.1 | 3.26 | 3.4 |
| 30.61 | 16.2 | 2.92 | 1.2 |
| 34.35 | 20.4 | 2.61 | 1.5 |
| 37.02 | 56.2 | 2.43 | 4.2 |

Dimethylformamide/acetonitrile (for example, at a volume ratio of 1:5) was used as a solvent to obtain the crystal form A. The peak information is shown in Table 15.

TABLE 15

XRPD peak information of crystal form A of scutellarin aglycone

| Pos. [°2Th.] | Height [cts] | d-spacing [Å] | Rel. Int. [%] |
|---|---|---|---|
| 7.35 | 76.1 | 12.03 | 2.8 |
| 11.36 | 220.2 | 7.79 | 8.1 |
| 14.02 | 395.2 | 6.31 | 14.5 |
| 14.73 | 2734.8 | 6.01 | 100.0 |
| 17.05 | 490.4 | 5.20 | 17.9 |
| 20.48 | 81.0 | 4.34 | 3.0 |
| 22.13 | 326.9 | 4.02 | 12.0 |
| 25.04 | 32.5 | 3.56 | 1.2 |
| 26.83 | 249.9 | 3.32 | 9.1 |
| 27.62 | 198.8 | 3.23 | 7.3 |
| 28.84 | 59.4 | 3.10 | 2.2 |
| 30.49 | 95.7 | 2.93 | 3.5 |
| 34.51 | 49.8 | 2.60 | 1.8 |
| 37.23 | 107.0 | 2.42 | 3.9 |

Method 5: about 1.5 mg crystal form A of scutellarin aglycone was weighed and added to a 3 mL glass bottle, and 0.2 mL methylpyrrolidone was added to completely dissolve the solid. 0.2~2 mL water was then slowly added dropwise. If precipitate appeared, the precipitate was separated. If no precipitate appeared, the solution was quickly evaporated at room temperature. Alternatively, in 0.2 dimethyl sulfoxide, methanol or acetone was used as an anti-solvent, and the crystal form A could be obtained. Alternatively, in 0.2 mL, dimethylformamide, water was used as an anti-solvent and a mixture of crystal form A and crystal form D could be obtained.

Dimethylformamide was used as a solvent, and water was used as an anti-solvent to obtain the crystal form A and crystal form D. The peak information is shown in Table 16.

TABLE 16

XRPD peak information of crystal form A and crystal form D of scutellarin aglycone

| Pos. [°2Th.] | Height [cts] | d-spacing [Å] | Rel. Int. [%] |
|---|---|---|---|
| 7.04 | 42.6 | 12.55 | 2.5 |
| 9.91 | 125.8 | 8.93 | 7.5 |
| 11.14 | 201.9 | 7.94 | 12.0 |
| 13.82 | 321.0 | 6.41 | 19.1 |
| 14.53 | 1684.8 | 6.10 | 100.0 |
| 15.68 | 267.2 | 5.65 | 15.9 |
| 16.88 | 408.8 | 5.25 | 24.3 |
| 17.93 | 77.4 | 4.95 | 4.6 |
| 20.32 | 87.7 | 4.37 | 5.2 |
| 21.97 | 219.5 | 4.05 | 13.0 |
| 24.30 | 48.0 | 3.66 | 2.9 |
| 26.25 | 186.9 | 3.39 | 11.1 |
| 26.64 | 465.9 | 3.35 | 27.7 |
| 27.39 | 370.1 | 3.26 | 22.0 |
| 27.96 | 98.0 | 3.19 | 5.8 |
| 28.64 | 88.6 | 3.12 | 5.3 |
| 30.30 | 108.5 | 2.95 | 6.4 |
| 34.40 | 21.7 | 2.61 | 1.3 |
| 37.09 | 56.7 | 2.42 | 3.4 |

Method 6: about 15 mg crystal form A of scutellarin aglycone was weighed and added to a 3 mL glass bottle. The glass bottle was placed in a vessel at a constant humidity (a relative humidity of 32.8% or 57.6% or 75.3% or 97.3%), and stored at room temperature for 11 days, to obtain the crystal form A.

When placing at a relative humidity 32.8%, the crystal form A was obtained. The peak information is shown in Table 17.

TABLE 17

XRPD peak information of crystal form A of scutellarin aglycone

| Pos. [°2Th.] | Height [cts] | d-spacing [Å] | Rel. Int. [%] |
|---|---|---|---|
| 11.17 | 147.5 | 7.92 | 18.3 |
| 13.85 | 233.7 | 6.39 | 29.0 |
| 14.54 | 805.6 | 6.09 | 100.0 |
| 16.87 | 240.1 | 5.26 | 29.8 |
| 20.33 | 91.7 | 4.37 | 11.4 |
| 21.98 | 142.2 | 4.04 | 17.7 |
| 26.67 | 377.5 | 3.34 | 46.9 |
| 27.40 | 299.9 | 3.25 | 37.2 |
| 28.65 | 70.7 | 3.12 | 8.8 |
| 30.31 | 99.5 | 2.95 | 12.4 |
| 37.06 | 28.8 | 2.43 | 3.6 |

When placing at a relative humidity of 57.6%, the crystal form A was obtained. The peak information is shown in Table 18.

TABLE 18

XRPD peak information of crystal form A of scutellarin aglycone

| Pos. [°2Th.] | Height [cts] | d-spacing [Å] | Rel. Int. [%] |
|---|---|---|---|
| 11.15 | 126.7 | 7.93 | 18.6 |
| 13.86 | 148.4 | 6.39 | 21.8 |
| 14.53 | 681.4 | 6.09 | 100.0 |
| 16.90 | 209.2 | 5.25 | 30.7 |
| 20.33 | 75.8 | 4.37 | 11.1 |
| 21.98 | 125.5 | 4.04 | 18.4 |
| 26.65 | 307.1 | 3.35 | 45.1 |
| 27.39 | 246.9 | 3.26 | 36.2 |
| 28.64 | 50.7 | 3.12 | 7.4 |
| 30.29 | 79.7 | 2.95 | 11.7 |
| 32.97 | 11.7 | 2.72 | 1.7 |
| 37.03 | 18.3 | 2.43 | 2.7 |

When placing at a relative humidity of 75.3%, the crystal form A was obtained. The peak information is shown in Table 19.

TABLE 19

XRPD peak information of crystal form A of scutellarin aglycone

| Pos. [°2Th.] | Height [cts] | d-spacing [Å] | Rel. Int. [%] |
|---|---|---|---|
| 11.15 | 127.2 | 7.94 | 16.8 |
| 13.81 | 215.4 | 6.41 | 28.4 |
| 14.54 | 758.9 | 6.09 | 100.0 |
| 16.88 | 241.5 | 5.25 | 31.8 |
| 20.33 | 110.2 | 4.37 | 14.5 |
| 22.00 | 195.9 | 4.04 | 25.8 |
| 24.64 | 28.0 | 3.61 | 3.7 |
| 26.65 | 505.1 | 3.35 | 66.6 |
| 27.43 | 442.1 | 3.25 | 58.3 |
| 28.66 | 98.6 | 3.11 | 13.0 |
| 30.30 | 131.6 | 2.95 | 17.3 |
| 33.71 | 27.3 | 2.66 | 3.6 |
| 37.03 | 35.7 | 2.43 | 4.7 |

When placing at a relative humidity of 97.3%, the crystal form A was obtained. The peak information is shown in Table 20.

TABLE 20

XRPD peak information of crystal form A of scutellarin aglycone

| Pos. [°2Th.] | Height [cts] | d-spacing [Å] | Rel. Int. [%] |
|---|---|---|---|
| 7.04 | 42.8 | 12.56 | 5.7 |
| 11.19 | 142.7 | 7.91 | 18.9 |
| 13.84 | 219.4 | 6.40 | 29.1 |
| 14.55 | 753.9 | 6.09 | 100.0 |
| 16.89 | 263.9 | 5.25 | 35.0 |
| 20.33 | 76.6 | 4.37 | 10.2 |
| 21.99 | 162.1 | 4.04 | 21.5 |
| 24.59 | 21.2 | 3.62 | 2.8 |
| 26.66 | 420.3 | 3.34 | 55.8 |
| 27.42 | 328.0 | 3.25 | 43.5 |
| 28.65 | 82.8 | 3.12 | 11.0 |
| 30.33 | 100.3 | 2.95 | 13.3 |
| 36.92 | 25.0 | 2.43 | 3.3 |

Method 7: about 15 mg crystal form A of scutellarin aglycone was weighed and added to a 3 mL glass bottle, and 0.2 mL methylpyrrolidone was added to completely dissolve the solid. The resultant solution was then slowly and dropwise added to water. If precipitate appeared, the precipitate was separated. If no precipitate appeared, the solution was quickly evaporated at room temperature. Alternatively, in 0.2 mL dimethyl sulfoxide, methanol or acetone was used as an anti-solvent, and the crystal form A could be obtained.

Alternatively, in 0.2 mL dimethylformamide, water was used as an anti solvent, and the crystal form A could be obtained.

Method 8: about 15 mg crystal form A of scutellarin aglycone was weighed and added to a 3 mL glass bottle, and the 3 mL glass bottle with the mouth open was placed in a 20 mL sealed glass bottle containing 3 mL dichloromethane or ethanol or methanol or toluene or acetonitrile or tetrahydrofuran or dimethylformamide or acetone. After placing at room temperature in dark for 13 days, the solid obtained was the crystal form A.

Method 9: about 15 mg crystal form A of scutellarin aglycone was weighed and added to a 3 mL glass bottle, and then 0.4~0.5 mL a mixed solvent of dimethyl sulfoxide/tetrahydrofuran (at a volume ratio of 2:1) or a mixed solvent of dimethyl sulfoxide/ethanol (at a volume ratio of 2:1) or a mixed solvent of dimethylformamide/acetonitrile (for example, at a volume ratio of 2:1) was separately added, to obtain a clear solution. About 3.0 mg ionic liquid ([Bmim] PF6 or [Bmim]BF4 or [Bmim]Br, wherein Bmim: 1-butyl-3-methylimidazolium cation) was added to the clear solution. The resultant solution was evaporated at room temperature slowly, to obtain the crystal form A.

Method 10: about 15 mg crystal form A of scutellarin aglycone was weighed and placed in an agate mortar. About 10 µL isopropanol or acetic acid or acetonitrile or acetone or isopropyl acetate was added, and the resultant mixture was ground for 15 min, to obtain the crystal form A.

EXAMPLE 2

Preparation of Crystal Form B of Scutellarin Aglycone

About 10 mg crystal form A of scutellarin aglycone was weighed and added to a 3 mL glass bottle, and 0.5~1.25 mL pyridine/water (at a volume ratio of 3:1) or pyridine/acetonitrile (at a volume ratio of 3:1) or pyridine/ethyl acetate (at a volume ratio of 3:1) was added, to completely dissolve the sample to obtain a clear solution. The resultant solution was slowly evaporated at room temperature, and after evaporation of the solvent to dryness, the crystal form B was obtained.

Method 1: pyridine/water (at a volume ratio of 3:1) was used as a solvent to obtain the crystal form B. The peak information is shown in Table 21.

TABLE 21

XRPD peak information of crystal form B of scutellarin aglycone

| Pos. [°2Th.] | Height [cts] | d-spacing [Å] | Rel. Int. [%] |
|---|---|---|---|
| 7.21 | 226.5 | 12.26 | 100.0 |
| 9.91 | 83.8 | 8.93 | 37.0 |
| 11.07 | 60.2 | 7.99 | 26.6 |
| 14.05 | 97.8 | 6.30 | 43.2 |
| 15.73 | 183.9 | 5.63 | 81.2 |
| 18.02 | 53.7 | 4.92 | 23.7 |
| 20.87 | 43.6 | 4.26 | 19.3 |
| 24.06 | 74.5 | 3.70 | 32.9 |
| 24.83 | 81.7 | 3.59 | 36.1 |
| 26.16 | 158.9 | 3.41 | 70.2 |
| 28.02 | 66.0 | 3.18 | 29.5 |

Method 2: pyridine/acetonitrile (at a volume ratio of 3:0 was used as a solvent to obtain the crystal form B. The peak information is shown in Table 22.

TABLE 22

XRPD peak information of crystal form B of scutellarin aglycone

| Pos. [°2Th.] | Height [cts] | d-spacing [Å] | Rel. Int. [%] |
|---|---|---|---|
| 7.22 | 613.2 | 12.24 | 100.0 |
| 9.88 | 54.3 | 8.96 | 8.9 |
| 14.56 | 195.2 | 6.08 | 31.8 |
| 15.70 | 92.3 | 5.65 | 15.1 |
| 18.88 | 104.6 | 4.70 | 17.1 |
| 20.77 | 122.6 | 4.28 | 20.0 |
| 21.98 | 51.5 | 4.04 | 8.4 |
| 24.84 | 164.9 | 3.59 | 26.9 |
| 26.12 | 63.9 | 3.41 | 10.4 |

Method 3: pyridine/ethyl acetate (at a volume ratio of 3:1) was used as a solvent to obtain the crystal form B. The peak information is shown in Table 23.

TABLE 23

XRPD peak information of crystal form B of scutellarin aglycone

| Peak List: Pos. [°2Th.] | Height [cts] | d-spacing [Å] | Rel. Int. [%] |
|---|---|---|---|
| 7.25 | 689.2 | 12.20 | 100.0 |
| 9.92 | 163.2 | 8.92 | 23.7 |
| 11.17 | 75.3 | 7.92 | 10.9 |
| 14.11 | 124.1 | 6.28 | 18.0 |
| 14.57 | 259.9 | 6.08 | 37.7 |
| 15.72 | 219.7 | 5.64 | 31.9 |
| 18.91 | 80.8 | 4.69 | 11.7 |
| 20.76 | 124.5 | 4.28 | 18.1 |
| 22.00 | 68.5 | 4.04 | 9.9 |
| 24.98 | 123.2 | 3.56 | 17.9 |
| 26.23 | 141.6 | 3.40 | 20.5 |
| 27.95 | 76.6 | 3.19 | 11.1 |
| 35.47 | 13.5 | 2.53 | 2.0 |

Figure 3:
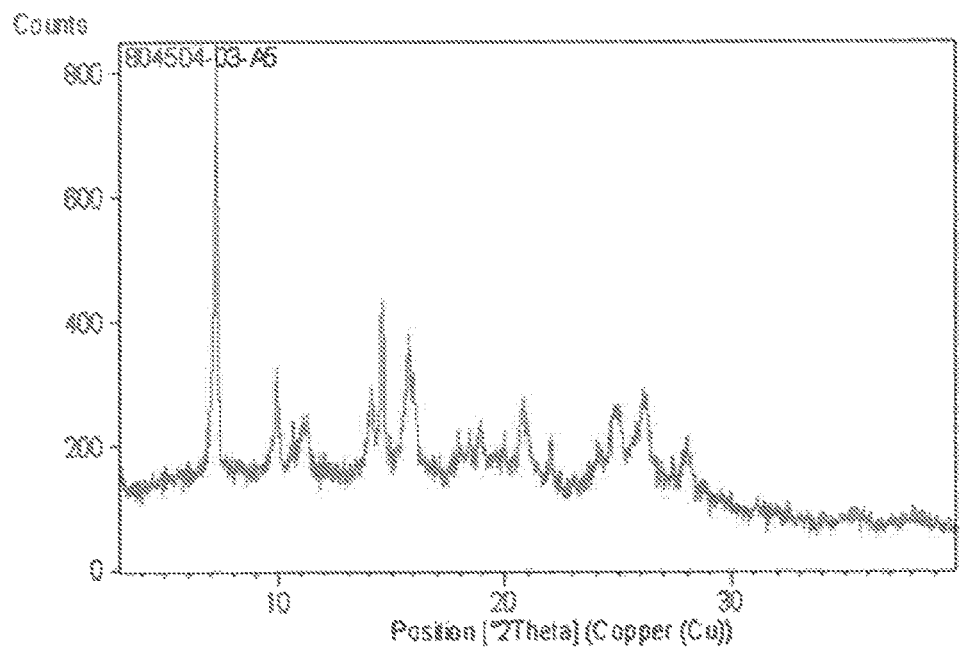
FIG. 3 shows the XRPD pattern of crystal form B of scutellarin aglycone.
Figure 4:
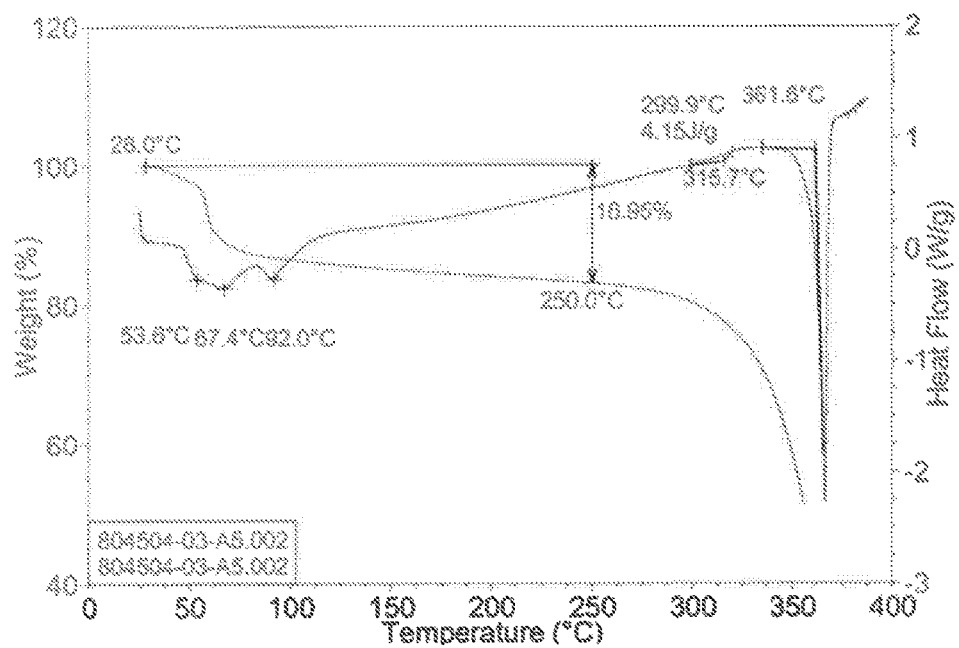
FIG. 4 shows the TGA and DSC thermograms of crystal form B of scutellarin aglycone.

The crystal form B prepared by Method 3 has a typical XRPD pattern shown in FIG. 3, the peak information is shown in Table 24, and typical TGA and DSC thermograms are shown in FIG. 4. The crystal form B has a melting range of (361.6° C.-368.3° C.), and a melting point of 361.6° C.

TABLE 24

XRPD peak information of crystal form B of scutellarin aglycone

| Peak List: Pos. [°2Th.] | Height [cts] | d-spacing [Å] | Rel. Int. [%] |
|---|---|---|---|
| 7.25 | 689.2 | 12.20 | 100.0 |
| 9.92 | 163.2 | 8.92 | 23.7 |
| 11.17 | 75.3 | 7.92 | 10.9 |
| 14.11 | 124.1 | 6.28 | 18.0 |
| 14.57 | 259.9 | 6.08 | 37.7 |
| 15.72 | 219.7 | 5.64 | 31.9 |
| 18.91 | 80.8 | 4.69 | 11.7 |
| 20.76 | 124.5 | 4.28 | 18.1 |
| 22.00 | 68.5 | 4.04 | 9.9 |
| 24.98 | 123.2 | 3.56 | 17.9 |
| 26.23 | 141.6 | 3.40 | 20.5 |
| 27.95 | 76.6 | 3.19 | 11.1 |
| 35.47 | 13.5 | 2.53 | 2.0 |

EXAMPLE 3

Preparation of Crystal Form C of Scutellarin Aglycone

Method 1 about 15 mg crystal form A of scutellarin aglycone was weighed and added to a 3 mL glass bottle, and 0.2 mL pyridine was added, to completely dissolve the solid, 0.2~2 mL heptane was then slowly added dropwise to the pyridine solution. If precipitate appeared, the precipitate was separated to obtain the solid sample. If no precipitate appeared, the solution was quickly evaporated a room temperature, to obtain the crystal form C. The peak information is shown in Table 25.

TABLE 25

XRPD peak information of crystal form C of scutellarin aglycone

| Pos. [°2Th.] | Height [cts] | d-spacing [Å] | Rel. Int. [%] |
|---|---|---|---|
| 5.84 | 75.7 | 15.13 | 3.5 |
| 7.24 | 2139.8 | 12.21 | 100.0 |
| 9.15 | 499.0 | 9.67 | 23.3 |
| 10.59 | 172.1 | 8.35 | 8.0 |
| 10.90 | 163.9 | 8.12 | 7.7 |
| 12.66 | 94.7 | 6.99 | 4.4 |
| 13.36 | 101.0 | 6.63 | 4.7 |
| 14.60 | 866.8 | 6.07 | 40.5 |
| 15.94 | 260.8 | 5.56 | 12.2 |
| 16.43 | 325.8 | 5.40 | 15.2 |
| 16.89 | 229.3 | 5.25 | 10.7 |
| 17.68 | 256.8 | 5.02 | 12.0 |
| 18.19 | 613.3 | 4.88 | 28.7 |
| 18.90 | 260.5 | 4.70 | 12.2 |
| 19.53 | 813.9 | 4.55 | 38.0 |
| 20.64 | 1519.3 | 4.30 | 71.0 |
| 21.52 | 429.0 | 4.13 | 20.1 |
| 22.01 | 225.4 | 4.04 | 10.5 |
| 22.84 | 382.2 | 3.89 | 17.9 |
| 23.77 | 203.4 | 3.74 | 9.5 |
| 24.39 | 579.2 | 3.65 | 27.1 |
| 24.62 | 1120.9 | 3.62 | 52.4 |
| 24.97 | 1977.7 | 3.57 | 92.4 |
| 25.70 | 354.1 | 3.47 | 16.6 |
| 26.70 | 359.7 | 3.34 | 16.8 |
| 26.99 | 650.9 | 3.30 | 30.4 |
| 27.66 | 447.4 | 3.22 | 20.9 |
| 28.67 | 242.4 | 3.11 | 11.3 |
| 29.31 | 213.3 | 3.05 | 10.0 |
| 30.91 | 63.6 | 2.89 | 3.0 |
| 32.43 | 198.2 | 2.76 | 9.3 |
| 33.48 | 59.7 | 2.68 | 2.8 |
| 35.53 | 120.3 | 2.53 | 5.6 |
| 37.18 | 41.7 | 2.42 | 2.0 |
| 38.11 | 149.1 | 2.36 | 7.0 |
| 39.07 | 65.8 | 2.31 | 3.1 |

Method 2: about 15 mg crystal form A of scutellarin aglycone was weighed and added to a 3 mL glass bottle, and 0.2 mL pyridine was added, to completely dissolve the solid. The resultant dear solution was slowly added to 5° C. heptane dropwise. If precipitate appeared, the precipitate was separated to obtain the solid sample. If no precipitate appeared, the solution was quickly evaporated at room temperature, to obtain the crystal form C. The peak information is shown in Table 26.

TABLE 26

XRPD peak information of crystal form C of scutellarin aglycone

| Pos. [°2Th.] | Height [cts] | d-spacing [Å] | Rel. Int. [%] |
|---|---|---|---|
| 7.23 | 657.8 | 12.22 | 100.0 |
| 9.15 | 88.8 | 9.66 | 13.5 |
| 14.58 | 248.7 | 6.08 | 37.8 |
| 16.17 | 53.5 | 5.48 | 8.1 |
| 16.86 | 42.6 | 5.26 | 6.5 |
| 18.20 | 113.3 | 4.87 | 17.2 |
| 19.52 | 149.3 | 4.55 | 22.7 |
| 20.62 | 294.6 | 4.31 | 44.8 |
| 21.52 | 74.8 | 4.13 | 11.4 |

TABLE 26-continued

XRPD peak information of crystal form C of scutellarin aglycone

| Pos. [°2Th.] | Height [cts] | d-spacing [Å] | Rel. Int. [%] |
|---|---|---|---|
| 22.83 | 52.4 | 3.90 | 8.0 |
| 24.96 | 308.8 | 3.57 | 47.0 |
| 26.97 | 75.4 | 3.31 | 11.5 |
| 27.69 | 59.3 | 3.22 | 9.0 |
| 32.39 | 27.5 | 2.76 | 4.2 |
| 35.47 | 23.9 | 2.53 | 3.6 |
| 37.96 | 26.6 | 2.37 | 4.0 |

Figure 5:
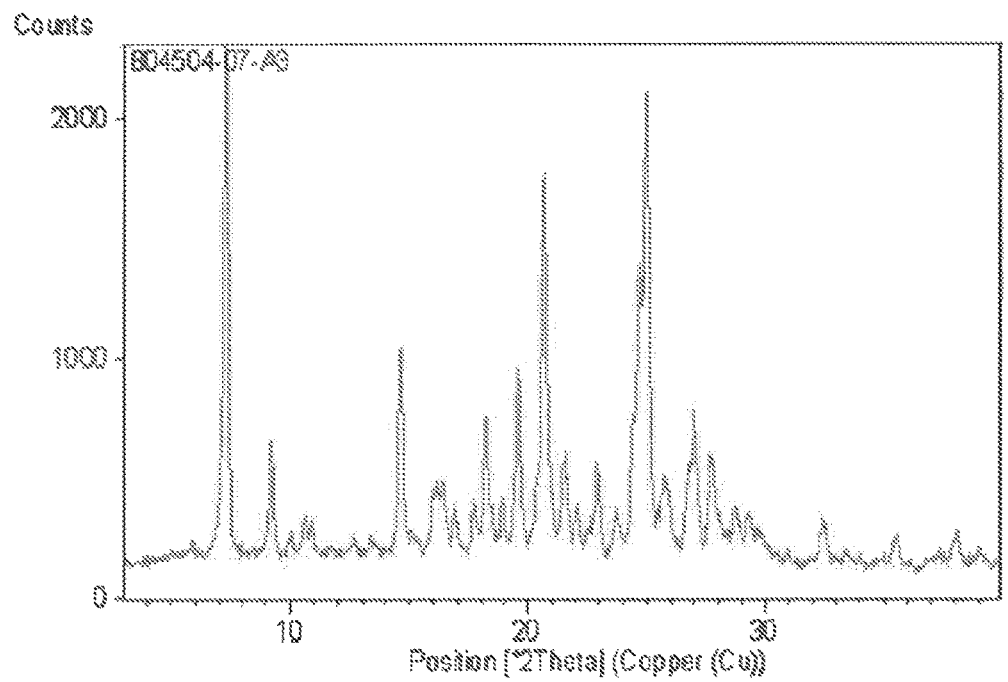
FIG. 5 shows the XRPD pattern of crystal form C of scutellarin aglycone.
Figure 6:
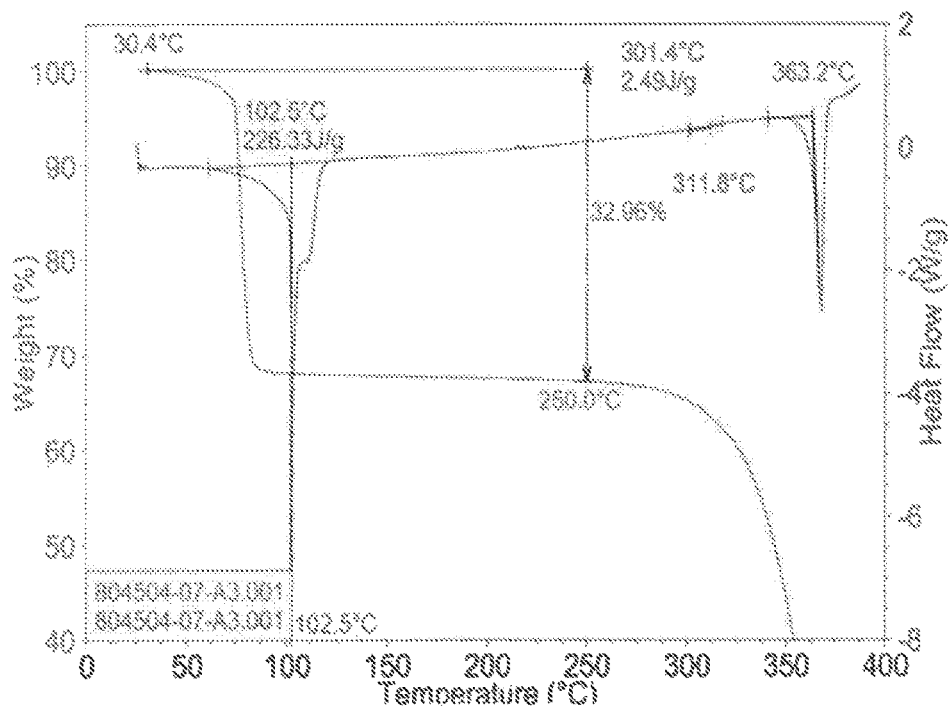
FIG. 6 shows the TGA and DSC thermograms of crystal form C of scutellarin aglycone.

The crystal form C prepared by Method 1 has a typical XRPD pattern shown in FIG. 5, the peak information is shown in Table 27, and typical TGA and DSC thermograms are shown in FIG. 6. The crystal form C has a melting range of (363.2° C.-369.9° C.), and a melting point of 363.2° C.

TABLE 27

XRPD peak information of crystal form C of scutellarin aglycone

| Pos. [°2Th.] | Height [cts] | d-spacing [Å] | Rel. Int. [%] |
|---|---|---|---|
| 5.84 | 75.7 | 15.13 | 3.5 |
| 7.24 | 2139.8 | 12.21 | 100.0 |
| 9.15 | 499.0 | 9.67 | 23.3 |
| 10.59 | 172.1 | 8.35 | 8.0 |
| 10.90 | 163.9 | 8.12 | 7.7 |
| 12.66 | 94.7 | 6.99 | 4.4 |
| 13.36 | 101.0 | 6.63 | 4.7 |
| 14.60 | 866.8 | 6.07 | 40.5 |
| 15.94 | 260.8 | 5.56 | 12.2 |
| 16.43 | 325.8 | 5.40 | 15.2 |
| 16.89 | 229.3 | 5.25 | 10.7 |
| 17.68 | 256.8 | 5.02 | 12.0 |
| 18.19 | 613.3 | 4.88 | 28.7 |
| 18.90 | 260.5 | 4.70 | 12.2 |
| 19.53 | 813.9 | 4.55 | 38.0 |
| 20.64 | 1519.3 | 4.30 | 71.0 |
| 21.52 | 429.0 | 4.13 | 20.1 |
| 22.01 | 225.4 | 4.04 | 10.5 |
| 22.84 | 382.2 | 3.89 | 17.9 |
| 23.77 | 203.4 | 3.74 | 9.5 |
| 24.39 | 579.2 | 3.65 | 27.1 |
| 24.62 | 1120.9 | 3.62 | 52.4 |
| 24.97 | 1977.7 | 3.57 | 92.4 |
| 25.70 | 354.1 | 3.47 | 16.6 |
| 26.70 | 359.7 | 3.34 | 16.8 |
| 26.99 | 650.9 | 3.30 | 30.4 |
| 27.66 | 447.4 | 3.22 | 20.9 |
| 28.67 | 242.4 | 3.11 | 11.3 |
| 29.31 | 213.3 | 3.05 | 10.0 |
| 30.91 | 63.6 | 2.89 | 3.0 |
| 32.43 | 198.2 | 2.76 | 9.3 |
| 33.48 | 59.7 | 2.68 | 2.8 |
| 35.53 | 120.3 | 2.53 | 5.6 |
| 37.18 | 41.7 | 2.42 | 2.0 |
| 38.11 | 149.1 | 2.36 | 7.0 |
| 39.07 | 65.8 | 2.31 | 3.1 |

EXAMPLE 4

Preparation of Crystal Form D of Scutellarin Aglycone

Method 1: about 10 mg crystal form A of scutellarin aglycone was weighed and added to a 3 mL glass bottle, and 0.5~1.25 mL a mixed solvent of pyridine/acetone (at a volume ratio of 3:1) or a mixed solvent of pyridine/heptane (at a volume ratio of 3:1) was added, to completely dissolve the sample to obtain a dear solution. The resultant solution was slowly evaporated at room temperature. After evaporation of the solvent to dryness, the solid obtained was the crystal form D.

Pyridine/acetone (at a volume ratio of 3:1) was used as a solvent to obtain the crystal form a The peak information is shown in Table 28.

TABLE 28

XRPD peak information of crystal form D of scutellarin aglycone

| Pos. [°2Th.] | Height [cts] | d-spacing [Å] | Rel. Int. [%] |
|---|---|---|---|
| 7.04 | 28.9 | 12.56 | 10.5 |
| 10.00 | 87.0 | 8.84 | 31.5 |
| 11.11 | 77.8 | 7.97 | 28.2 |
| 14.22 | 122.5 | 6.23 | 44.4 |
| 15.77 | 223.5 | 5.62 | 81.0 |
| 18.01 | 62.6 | 4.93 | 22.7 |
| 24.10 | 125.6 | 3.69 | 45.5 |
| 26.10 | 276.1 | 3.41 | 100.0 |
| 28.05 | 131.9 | 3.18 | 47.8 |
| 29.63 | 19.5 | 3.02 | 7.1 |
| 34.98 | 17.0 | 2.57 | 6.2 |

Pyridine/heptane (at a volume ratio of 3:1) was used as a solvent to obtain the crystal form D. The peak information is shown in Table 29.

TABLE 29

XRPD peak information of crystal form D of scutellarin aglycone

| Pos. [°2Th.] | Height [cts] | d-spacing [Å] | Rel. Int. [%] |
|---|---|---|---|
| 8.28 | 39.5 | 10.68 | 10.5 |
| 9.91 | 121.8 | 8.92 | 32.3 |
| 11.06 | 134.5 | 8.00 | 35.7 |
| 14.05 | 228.7 | 6.30 | 60.7 |
| 15.70 | 376.8 | 5.65 | 100.0 |
| 17.93 | 84.4 | 4.95 | 22.4 |
| 24.02 | 83.4 | 3.70 | 22.1 |
| 26.03 | 193.8 | 3.42 | 51.4 |
| 27.95 | 83.5 | 3.19 | 22.2 |

Method 2: about 15 mg crystal form A of scutellarin aglycone was weighed and added to a 3 mL glass bottle, and 0.2 mL pyridine was added, to completely dissolve the solid. 0.2~2 mL ethanol was then slowly added dropwise. If precipitate appeared, the precipitate was separated to obtain the solid sample. If no precipitate appeared, the solution was quickly evaporated at room temperature. Alternatively, in 0.2 mL dimethylformamide, tetrahydrofuran was used as an anti solvent, and the crystal form D could be obtained.

Pyridine was used as a normal solvent, and ethanol was used as an anti-solvent to obtain the crystal form D. The peak information is shown in Table 30.

TABLE 30

XRPD peak information of crystal form D of scutellarin aglycone

| Pos. [°2Th.] | Height [cts] | d-spacing [Å] | Rel. Int. [%] |
|---|---|---|---|
| 6.98 | 106.4 | 12.66 | 6.0 |
| 9.97 | 467.0 | 8.87 | 26.4 |
| 11.10 | 473.8 | 7.97 | 26.8 |
| 14.09 | 875.6 | 6.29 | 49.5 |
| 15.72 | 1427.2 | 5.64 | 80.6 |
| 18.00 | 501.7 | 4.93 | 28.3 |
| 19.94 | 205.3 | 4.45 | 11.6 |
| 21.24 | 183.8 | 4.18 | 10.4 |
| 24.04 | 923.5 | 3.70 | 52.2 |
| 24.56 | 278.9 | 3.62 | 15.8 |

TABLE 30-continued

XRPD peak information of crystal form D of scutellarin aglycone

| Pos. [°2Th.] | Height [cts] | d-spacing [Å] | Rel. Int. [%] |
|---|---|---|---|
| 25.56 | 341.1 | 3.49 | 19.3 |
| 26.07 | 1770.0 | 3.42 | 100.0 |
| 27.99 | 938.2 | 3.19 | 53.0 |
| 29.44 | 227.8 | 3.03 | 12.9 |
| 29.82 | 160.2 | 3.00 | 9.1 |
| 30.83 | 82.7 | 2.90 | 4.7 |
| 31.82 | 116.8 | 2.81 | 6.6 |
| 35.03 | 138.1 | 2.56 | 7.8 |
| 36.94 | 21.5 | 2.43 | 1.22 |

Dimethylformamide was used as a normal solvent, and tetrahydrofuran was used as an anti-solvent, to obtain the crystal form D. The peak information is shown in Table 31.

TABLE 31

XRPD peak information of crystal form D of scutellarin aglycone

| Pos. [°2Th.] | Height [cts] | d-spacing [Å] | Rel. Int. [%] |
|---|---|---|---|
| 6.97 | 114.3 | 12.69 | 3.2 |
| 9.86 | 798.9 | 8.97 | 22.0 |
| 11.07 | 976.1 | 7.99 | 26.9 |
| 14.06 | 1147.1 | 6.30 | 31.6 |
| 15.70 | 3630.9 | 5.64 | 100.0 |
| 17.96 | 622.1 | 4.94 | 17.1 |
| 19.91 | 416.1 | 4.46 | 11.5 |
| 21.22 | 126.3 | 4.19 | 3.5 |
| 22.24 | 28.6 | 4.00 | 0.8 |
| 24.04 | 187.2 | 3.70 | 5.2 |
| 24.56 | 41.1 | 3.62 | 1.1 |
| 25.08 | 41.6 | 3.55 | 1.2 |
| 25.50 | 151.9 | 3.49 | 4.2 |
| 26.06 | 575.4 | 3.42 | 15.9 |
| 27.12 | 61.6 | 3.29 | 1.7 |
| 27.95 | 421.9 | 3.19 | 11.6 |
| 29.38 | 138.6 | 3.04 | 3.8 |
| 29.77 | 65.2 | 3.00 | 1.8 |
| 31.80 | 221.1 | 2.81 | 6.1 |
| 35.00 | 93.4 | 2.56 | 2.6 |
| 36.82 | 38.8 | 2.44 | 1.1 |
| 38.72 | 18.1 | 2.33 | 0.5 |
| 39.70 | 31.1 | 2.27 | 0.9 |

Method 3: about 500 mg crystal form A of seutellarin aglycone was weighed and added to a 20 mL and 2.5 mL pyridine was added to dissolve it, to obtain a clear solution (magnetic stirring). 14.5 mL ethanol was added dropwise to the pyridine solution. The sample was precipitated and then separated by centrifugation to obtain the crystal form D.

Method 4: about 15 mg crystal form A of scutellarin aglycone was weighed and added to a 3 mL glass bottle, and 0.2 mL N-methylpyrrolidone was added, to completely dissolve the solid. The clear solution was slowly added dropwise to 5° C. acetonitrile. If precipitate appeared, the precipitate was separated to obtain the solid sample. If no precipitate appeared, the solution was quickly evaporated at room temperature to prepare it. The combination of said solvent and anti-solvent may be pyridine/ethanol or dimethylformamide/tetrahydrofuran and the crystal form could also be obtained.

N-methylpyrrolidone/acetonitrile was used to obtain the crystal form D. The peak information is shown in Table 32.

TABLE 32

XRPD peak information of crystal form D of scutellarin aglycone

| Pos. [°2Th.] | Height [cts] | d-spacing [Å] | Rel. Int. [%] |
|---|---|---|---|
| 6.98 | 185.3 | 12.66 | 5.0 |
| 9.86 | 742.0 | 8.97 | 20.0 |
| 11.07 | 945.8 | 7.99 | 25.5 |
| 14.08 | 1060.8 | 6.29 | 28.6 |
| 15.71 | 3705.9 | 5.64 | 100.0 |
| 17.98 | 809.5 | 4.93 | 21.8 |
| 19.91 | 603.5 | 4.46 | 16.3 |
| 21.25 | 188.1 | 4.18 | 5.1 |
| 22.40 | 98.7 | 3.97 | 2.7 |
| 24.06 | 234.5 | 3.70 | 6.3 |
| 24.58 | 85.5 | 3.62 | 2.3 |
| 25.18 | 132.7 | 3.54 | 3.6 |
| 25.52 | 238.9 | 3.49 | 6.5 |
| 26.04 | 591.4 | 3.42 | 16.0 |
| 27.94 | 434.3 | 3.19 | 11.7 |
| 29.44 | 201.5 | 3.03 | 5.4 |
| 29.78 | 115.4 | 3.00 | 3.1 |
| 30.89 | 55.0 | 2.89 | 1.5 |
| 31.80 | 422.4 | 2.81 | 11.4 |
| 35.01 | 127.1 | 2.56 | 3.4 |
| 36.84 | 97.0 | 2.44 | 2.6 |
| 38.57 | 89.5 | 2.33 | 2.4 |

Pyridine/ethanol was used to obtain crystal form D. The peak information is shown in Table 33.

TABLE 33

XRPD peak information of crystal form D of scutellarin aglycone

| Pos. [°2Th.] | Height [cts] | d-spacing [Å] | Rel. Int. [%] |
|---|---|---|---|
| 7.02 | 67.1 | 12.60 | 9.3 |
| 10.01 | 163.1 | 8.84 | 22.7 |
| 11.13 | 176.9 | 7.95 | 24.6 |
| 14.12 | 298.6 | 6.27 | 41.6 |
| 15.76 | 480.3 | 5.62 | 66.8 |
| 18.02 | 125.5 | 4.92 | 17.5 |
| 19.98 | 30.9 | 4.45 | 4.3 |
| 24.06 | 301.8 | 3.70 | 42.0 |
| 24.58 | 68.9 | 3.62 | 9.6 |
| 26.08 | 718.6 | 3.42 | 100.0 |
| 27.99 | 397.6 | 3.19 | 55.3 |
| 29.79 | 62.1 | 3.00 | 8.7 |
| 31.89 | 36.4 | 2.81 | 5.1 |
| 35.01 | 60.0 | 2.56 | 8.4 |

Dimethylformamide/tetrahydrofuran was used to obtain the crystal form D. The peak information is shown in Table 34.

TABLE 34

XRPD peak information of crystal form D of scutellarin aglycone

| Pos. [°2Th.] | Height [cts] | d-spacing [Å] | Rel. Int. [%] |
|---|---|---|---|
| 5.24 | 63.5 | 16.87 | 3.2 |
| 7.04 | 207.1 | 12.55 | 10.5 |
| 9.93 | 490.5 | 8.91 | 24.8 |
| 10.02 | 479.1 | 8.83 | 24.3 |
| 11.13 | 778.3 | 7.95 | 39.4 |
| 14.14 | 1084.0 | 6.26 | 54.9 |
| 15.77 | 1975.5 | 5.62 | 100.0 |
| 18.02 | 507.2 | 4.92 | 25.7 |
| 19.97 | 188.8 | 4.45 | 9.6 |
| 21.29 | 122.4 | 4.17 | 6.2 |
| 24.08 | 277.6 | 3.70 | 14.1 |
| 24.59 | 67.4 | 3.62 | 3.4 |
| 25.18 | 77.6 | 3.54 | 3.9 |
| 25.63 | 94.0 | 3.48 | 4.8 |
| 26.12 | 630.4 | 3.41 | 31.9 |
| 27.21 | 82.2 | 3.28 | 4.2 |
| 28.00 | 460.3 | 3.19 | 23.3 |
| 29.47 | 190.4 | 3.03 | 9.6 |
| 29.81 | 66.5 | 3.00 | 3.4 |
| 30.84 | 63.4 | 2.90 | 3.2 |
| 31.86 | 152.6 | 2.81 | 7.7 |
| 35.03 | 90.0 | 2.56 | 4.6 |

Method 5: about 15 mg crystal form A of scutellarin aglycone was weighed and added to a 3 mL glass bottle, and 0.5~1.0 mL dimethylformamide/butanone (at a volume ratio of 1:1) was added, to obtain a clear solution. About 1.5 mg mixed polymer (a mixed polymer: prepared by mixing polyvinyl pyrrolidone (PVP), polyvinyl alcohol (PVA), polyvinyl acetate) (PVAc), polyvinyl chloride (PVC), hydroxypropyl methyl cellulose (HPMC) and methylcellulose (MC) at a mass ratio of 1:1:1:1:1:1) was added to the clear solution. The resultant solution was evaporated at room temperature slowly, to obtain the crystal form D. The peak information is shown in Table 35.

TABLE 35

XRPD peak information of crystal form D of scutellarin aglycone

| Pos. [°2Th.] | Height [cts] | d-spacing [Å] | Rel. Int. [%] |
|---|---|---|---|
| 7.02 | 167.8 | 12.58 | 4.4 |
| 9.91 | 798.0 | 8.92 | 21.0 |
| 11.11 | 1098.2 | 7.96 | 28.9 |
| 14.11 | 1376.8 | 6.28 | 36.2 |
| 14.57 | 174.0 | 6.08 | 4.6 |
| 15.74 | 3805.6 | 5.63 | 100.0 |
| 18.00 | 819.2 | 4.93 | 21.5 |
| 19.95 | 443.1 | 4.45 | 11.6 |
| 21.27 | 183.5 | 4.18 | 4.8 |
| 22.36 | 70.6 | 3.98 | 1.9 |
| 24.08 | 399.9 | 3.70 | 10.5 |
| 24.61 | 114.7 | 3.62 | 3.0 |
| 25.13 | 110.1 | 3.54 | 2.9 |
| 25.59 | 224.2 | 3.48 | 5.9 |
| 26.11 | 1148.3 | 3.41 | 30.2 |
| 27.16 | 95.8 | 3.28 | 2.5 |
| 27.99 | 882.7 | 3.19 | 23.2 |
| 29.43 | 248.1 | 3.04 | 6.5 |
| 29.82 | 153.6 | 3.00 | 4.0 |
| 30.80 | 77.4 | 2.90 | 2.0 |
| 31.83 | 302.3 | 2.81 | 7.9 |
| 35.02 | 187.1 | 2.56 | 4.9 |
| 36.84 | 49.7 | 2.44 | 1.3 |
| 38.59 | 76.7 | 2.33 | 2.0 |
| 38.96 | 78.9 | 2.31 | 2.1 |

Method 6: about 15 mg sample of crystal form A was weighed and added to a 1.5 mL glass bottle, and 0.5 mL acetone was added to obtain a suspension. After magnetic stirring at room temperature for 6 days, the solid was separated by centrifugation. Alternatively, about 15 mg sample of crystal form A was weighed and added to a 1.5 mL glass bottle, and 0.5 mL acetonitrile was added to obtain a suspension. After magnetic stirring at 50° C. for 6 days, the solid was separated by centrifugation to obtain a mixed crystal of the crystal form D and crystal form A.

Acetone was added to obtain a suspension. After magnetic stirring at room temperature for 6 days, the crystal form D and crystal form A were obtained. The peak information is shown in Table 36.

TABLE 36

XRPD peak information of crystal form D and crystal form A of scutellarin aglycone

| Pos. [°2Th.] | Height [cts] | d-spacing [Å] | Rel. Int. [%] |
|---|---|---|---|
| 7.01 | 107.7 | 12.61 | 9.5 |
| 9.90 | 141.0 | 8.94 | 12.4 |
| 11.09 | 183.3 | 7.98 | 16.2 |
| 13.83 | 165.7 | 6.40 | 14.6 |
| 14.06 | 204.3 | 6.30 | 18.0 |
| 14.56 | 1135.2 | 6.08 | 100.0 |
| 15.72 | 577.2 | 5.64 | 50.9 |
| 16.88 | 227.7 | 5.25 | 20.1 |
| 17.98 | 108.2 | 4.93 | 9.5 |
| 19.91 | 79.2 | 4.46 | 7.0 |
| 21.93 | 189.7 | 4.05 | 16.7 |
| 26.06 | 55.7 | 3.42 | 4.9 |
| 26.69 | 77.8 | 3.34 | 6.9 |
| 27.45 | 67.3 | 3.25 | 5.9 |
| 27.95 | 54.2 | 3.19 | 4.8 |
| 29.37 | 26.3 | 3.04 | 2.3 |
| 30.33 | 42.2 | 2.95 | 3.7 |
| 31.83 | 54.0 | 2.81 | 4.8 |
| 34.36 | 26.8 | 2.61 | 2.4 |
| 37.07 | 85.2 | 2.43 | 7.5 |

Acetonitrile was added to obtain a suspension. After magnetic stirring at 50° C. for 6 days, the crystal form D and crystal form A were obtained. The peak information is shown in Table 37.

TABLE 37

XRPD peak information of crystal form D and crystal form A of scutellarin aglycone

| Pos. [°2Th.] | Height [cts] | d-spacing [Å] | Rel. Int. [%] |
|---|---|---|---|
| 6.96 | 66.9 | 12.70 | 7.9 |
| 9.92 | 68.3 | 8.92 | 8.0 |
| 11.16 | 138.2 | 7.93 | 16.2 |
| 13.83 | 193.1 | 6.40 | 22.7 |
| 14.54 | 852.2 | 6.09 | 100.0 |
| 15.67 | 225.0 | 5.66 | 26.4 |
| 16.89 | 212.1 | 5.25 | 24.9 |
| 17.95 | 43.1 | 4.94 | 5.1 |
| 20.32 | 62.7 | 4.37 | 7.4 |
| 21.93 | 139.6 | 4.05 | 16.4 |
| 23.98 | 36.0 | 3.71 | 4.2 |
| 26.03 | 127.5 | 3.42 | 15.0 |
| 26.68 | 282.1 | 3.34 | 33.1 |
| 27.44 | 235.1 | 3.25 | 27.6 |
| 28.00 | 78.2 | 3.19 | 9.2 |
| 28.64 | 55.4 | 3.12 | 6.5 |
| 30.33 | 82.6 | 2.95 | 9.7 |
| 34.81 | 25.0 | 2.58 | 2.9 |
| 37.09 | 60.4 | 2.42 | 7.1 |

Method 7: about 15 mg sample of crystal form A was weighed and added to a 3 mL glass bottle, and 0.2 mL dimethylformamide was added to completely dissolve the solid. 0.2-2 mL water was then slowly added dropwise. The solid was separated by centrifugation to obtain a mixed crystal of the crystal form D and crystal form A. The peak information is shown in Table 38.

TABLE 38

XRPD peak information of crystal form D and crystal form A of scutellarin aglycone

| Pos. [°2Th.] | Height [cts] | d-spacing [Å] | Rel. Int. [%] |
|---|---|---|---|
| 7.04 | 42.6 | 12.55 | 2.5 |
| 9.91 | 125.8 | 8.93 | 7.5 |
| 11.14 | 201.9 | 7.94 | 12.0 |
| 13.82 | 321.0 | 6.41 | 19.1 |
| 14.53 | 1684.8 | 6.10 | 100.0 |
| 15.68 | 267.2 | 5.65 | 15.9 |
| 16.88 | 408.8 | 5.25 | 24.3 |
| 17.93 | 77.4 | 4.95 | 4.6 |
| 20.32 | 87.7 | 4.37 | 5.2 |
| 21.97 | 219.5 | 4.05 | 13.0 |
| 24.30 | 48.0 | 3.66 | 2.9 |
| 26.25 | 186.9 | 3.39 | 11.1 |
| 26.64 | 465.9 | 3.35 | 27.7 |
| 27.39 | 370.1 | 3.26 | 22.0 |
| 27.96 | 98.0 | 3.19 | 5.8 |
| 28.64 | 88.6 | 3.12 | 5.3 |
| 30.30 | 108.5 | 2.95 | 6.4 |
| 34.40 | 21.7 | 2.61 | 1.3 |
| 37.09 | 56.7 | 2.42 | 3.4 |

Figure 7:
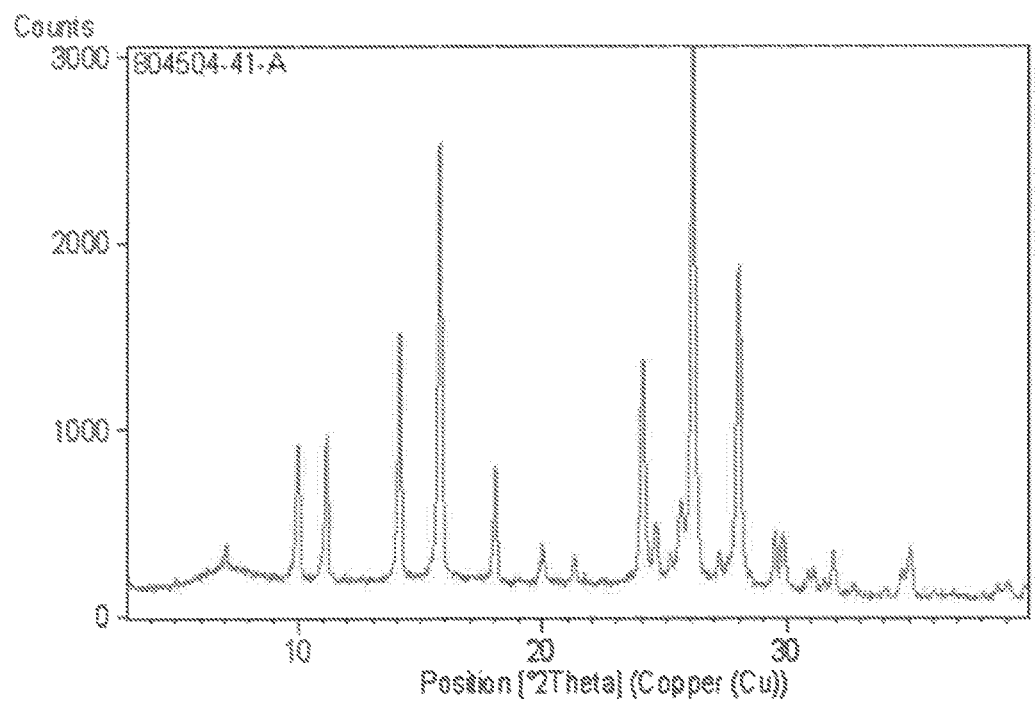
FIG. 7 shows the XRPD pattern of crystal form D of scutellarin aglycone.
Figure 8:
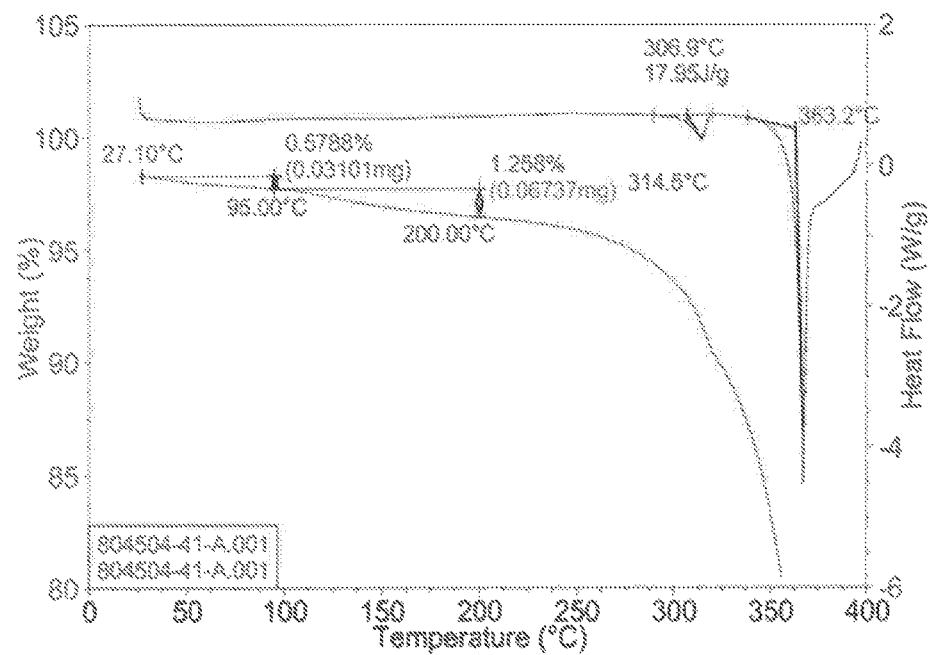
FIG. 8 shows the TGA and DSC thermograms of crystal form D of scutellarin aglycone.

The crystal form D, prepared by Method 4 using N-methylformamide as a solvent and acetonitrile as an anti-solvent, has a typical XRPD pattern shown in FIG. 7, the peak information is shown in Table 39, and typical TGA and DSC thermograms are shown in FIG. 8. The crystal form D has a melting range of (363.2° C.-369.7° C.), and a melting point of 363.2° C.

TABLE 39

XRPD peak information of crystal form D of scutellarin aglycone

| Pos. [°2Th.] | Height [cts] | d-spacing [Å] | Rel. Int. [%] |
|---|---|---|---|
| 7.04 | 196.2 | 12.55 | 6.7 |
| 9.98 | 730.5 | 8.86 | 24.9 |
| 11.15 | 784.5 | 7.94 | 26.8 |
| 14.13 | 1359.7 | 6.27 | 46.4 |
| 15.77 | 2385.7 | 5.62 | 81.3 |
| 18.04 | 651.8 | 4.92 | 22.2 |
| 19.97 | 249.6 | 4.45 | 8.5 |
| 21.29 | 177.2 | 4.17 | 6.0 |
| 24.08 | 1242.5 | 3.70 | 42.4 |
| 24.59 | 352.9 | 3.62 | 12.0 |
| 25.18 | 196.3 | 3.54 | 6.7 |
| 25.59 | 487.9 | 3.48 | 16.6 |
| 26.11 | 2933.3 | 3.41 | 100.0 |
| 27.21 | 219.4 | 3.28 | 7.5 |
| 28.00 | 1765.1 | 3.19 | 60.2 |
| 29.46 | 302.6 | 3.03 | 10.3 |
| 29.83 | 314.2 | 3.00 | 10.7 |
| 30.83 | 128.6 | 2.90 | 4.4 |
| 31.07 | 149.8 | 2.88 | 5.1 |
| 31.90 | 243.4 | 2.81 | 8.3 |
| 32.75 | 61.9 | 2.73 | 2.1 |
| 34.08 | 47.9 | 2.63 | 1.6 |
| 34.71 | 112.2 | 2.58 | 3.8 |
| 35.08 | 239.3 | 2.56 | 8.2 |
| 38.66 | 69.2 | 2.33 | 2.4 |
| 39.01 | 71.2 | 2.31 | 2.4 |

EXAMPLE 5

Preparation of Crystal Form E of Scutellarin Aglycone

Method 1: the sample of crystal form A was heated to 300° C. in TGA and kept for 5-10 min. After naturally cooling to the room temperature, the solid of crystal form E could be obtained. The peak information is shown in Table 40.

TABLE 40

XRPD peak information of crystal form E of scutellarin aglycone

| Pos. [°2Th.] | Height [cts] | d-spacing [Å] | Rel. Int. [%] |
| --- | --- | --- | --- |
| 9.58 | 200.1 | 9.23 | 43.6 |
| 10.19 | 130.3 | 8.68 | 28.4 |
| 10.88 | 133.1 | 8.14 | 29.0 |
| 14.05 | 278.6 | 6.31 | 60.7 |
| 15.33 | 458.9 | 5.78 | 100.0 |
| 16.11 | 117.7 | 5.50 | 25.7 |
| 17.75 | 157.2 | 5.00 | 34.3 |
| 19.34 | 82.1 | 4.59 | 17.9 |
| 21.19 | 50.3 | 4.19 | 11.0 |
| 25.85 | 159.7 | 3.45 | 34.8 |
| 26.61 | 230.9 | 3.35 | 50.3 |
| 28.48 | 50.4 | 3.13 | 11.0 |
| 29.75 | 57.8 | 3.00 | 12.6 |
| 31.06 | 58.7 | 2.88 | 12.8 |

Method 2: the sample of crystal form D was placed in TGA device, and was heated to 330° C. at 10° C./min and equilibrated for 3 min. After naturally cooling to the room temperature under the protection of $N_2$, the crystal form E was obtained.

Figure 9:
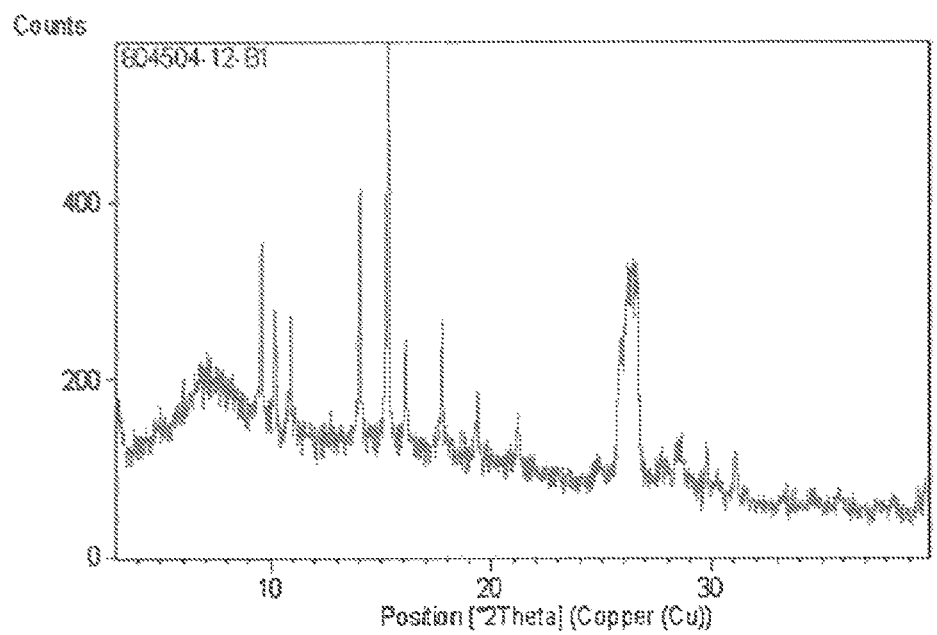
FIG. 9 shows the XRPD pattern of crystal form E of scutellarin aglycone.
Figure 10:
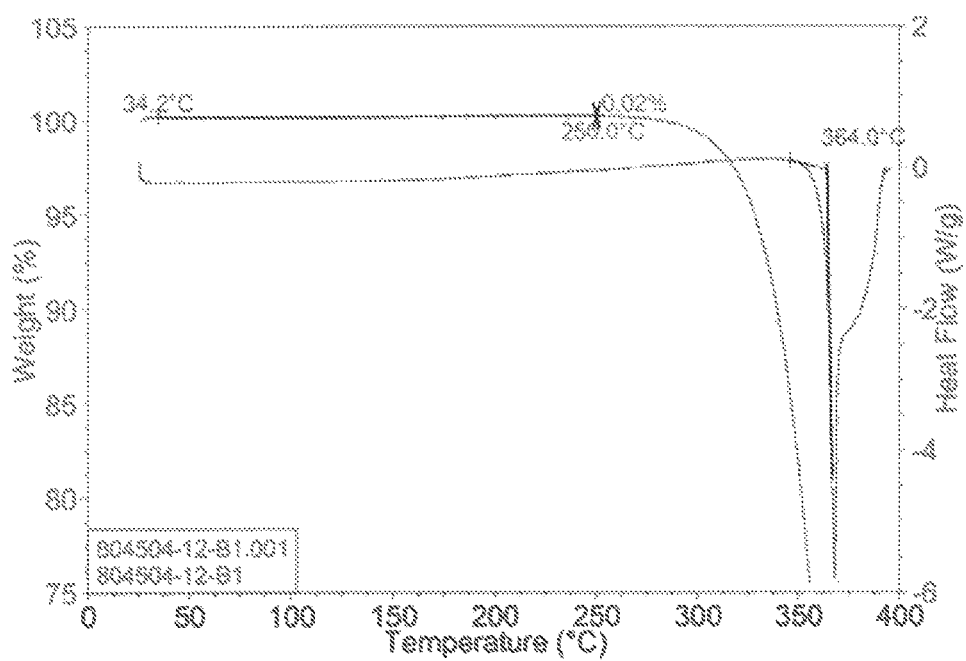
FIG. 10 shows the TGA and DSC thermograms of crystal form E of scutellarin aglycone.

The crystal form E, prepared by Method 1, has a typical XRPD pattern shown in FIG. 9, and the peak information is shown in Table 41. The typical TGA and DSC thermograms of the crystal form E are shown in FIG. 10. The crystal form E has a melting range of (364.0° C.-.369.2° C.), and a melting point of 364.0° C.

TABLE 41

XRPD peak information of crystal form E of scutellarin aglycone

| Pos. [°2Th.] | Height[cts] | d-spacing[Å] | Rel. Int. [%] |
| --- | --- | --- | --- |
| 9.58 | 200.1 | 9.23 | 43.6 |
| 10.19 | 130.3 | 8.68 | 28.4 |
| 10.88 | 133.1 | 8.14 | 29.0 |
| 14.05 | 278.6 | 6.31 | 60.7 |
| 15.33 | 458.9 | 5.78 | 100.0 |
| 16.11 | 117.7 | 5.50 | 25.7 |
| 17.75 | 157.2 | 5.00 | 34.3 |
| 19.34 | 82.1 | 4.59 | 17.9 |
| 21.19 | 50.3 | 4.19 | 11.0 |
| 25.85 | 159.7 | 3.45 | 34.8 |
| 26.61 | 230.9 | 3.35 | 50.3 |
| 28.48 | 50.4 | 3.13 | 11.0 |
| 29.75 | 57.8 | 3.00 | 12.6 |
| 31.06 | 58.7 | 2.88 | 12.8 |

EXAMPLE 6

Preparation of Crystal Form F of Scutellarin Aglycone

Method 1: about 15 mg sample of crystal form A was weighed and added to a 1.5 mL glass bottle, and 0.5 mL n-hexane or toluene was added to obtain a suspension. After magnetic stirring at room temperature for 6 days, the solid was separated by centrifugation to obtain a mixture of the crystal form A and crystal form F. Alternatively, a similar result could be obtained by subjecting the suspension to magnetic stirring at 50° C. for 6 days.

N-hexane was added to obtain a suspension. After magnetic stirring at room temperature for 6 days, the crystal form F and crystal form A were obtained. The peak information is shown in Table 42.

TABLE 42

XRPD peak information of crystal form F and crystal form A of scutellarin aglycone

| Pos. [°2Th.] | Height [cts] | d-spacing [Å] | Rel. Int. [%] |
| --- | --- | --- | --- |
| 7.13 | 33.6 | 12.40 | 1.3 |
| 11.25 | 517.1 | 7.86 | 20.5 |
| 13.92 | 655.5 | 6.36 | 26.0 |
| 14.64 | 1544.3 | 6.05 | 61.2 |
| 16.97 | 695.7 | 5.23 | 27.6 |
| 17.98 | 1368.4 | 4.93 | 54.2 |
| 18.09 | 1452.3 | 4.90 | 57.5 |
| 20.42 | 283.2 | 4.35 | 11.2 |
| 21.37 | 119.1 | 4.16 | 4.7 |
| 22.15 | 648.7 | 4.01 | 25.7 |
| 23.03 | 97.3 | 3.86 | 3.9 |
| 24.49 | 176.6 | 3.63 | 7.0 |
| 24.91 | 218.6 | 3.58 | 8.7 |
| 26.75 | 2525.5 | 3.33 | 100.0 |
| 27.51 | 1956.1 | 3.24 | 77.5 |
| 28.78 | 402.0 | 3.10 | 15.9 |
| 30.39 | 624.4 | 2.94 | 24.7 |
| 31.17 | 117.8 | 2.87 | 4.7 |
| 32.42 | 85.1 | 2.76 | 3.4 |
| 33.18 | 70.6 | 2.70 | 2.8 |
| 33.82 | 142.4 | 2.65 | 5.6 |
| 34.80 | 122.3 | 2.58 | 4.8 |

Toluene was added to obtain a suspension. After magnetic stirring at room temperature for 6 days, the crystal form F and crystal form A were obtained. The peak information is shown in Table 43.

TABLE 43

XRPD peak information of crystal form F and crystal form A of scutellarin aglycone

| Pos. [°2Th.] | Height [cts] | d-spacing [Å] | Rel. Int. [%] |
| --- | --- | --- | --- |
| 11.19 | 115.2 | 7.91 | 20.0 |
| 13.83 | 187.3 | 6.40 | 32.5 |
| 14.56 | 575.5 | 6.08 | 100.0 |
| 16.91 | 218.5 | 5.24 | 38.0 |
| 17.98 | 140.5 | 4.93 | 24.4 |
| 20.33 | 78.3 | 4.37 | 13.6 |
| 22.07 | 167.7 | 4.03 | 29.1 |
| 23.78 | 81.5 | 3.74 | 14.2 |
| 26.67 | 387.6 | 3.34 | 67.4 |
| 27.44 | 301.9 | 3.25 | 52.5 |
| 28.68 | 79.5 | 3.11 | 13.8 |
| 30.33 | 93.7 | 2.95 | 16.3 |
| 37.07 | 46.9 | 2.42 | 8.2 | n-Hexane was added to obtain a suspension. After magnetic stirring at 50° C. for 6 days, the crystal harm F and crystal form A were obtained. The peak information is shown in Table 44.

TABLE 44

XRPD peak information of crystal form F and crystal form A of scutellarin aglycone

| Pos. [°2Th.] | Height [cts] | d-spacing [Å] | Rel. Int. [%] |
| --- | --- | --- | --- |
| 11.16 | 87.2 | 7.93 | 9.5 |
| 13.84 | 141.7 | 6.40 | 15.4 |
| 14.54 | 541.4 | 6.09 | 59.0 |
| 16.89 | 198.8 | 5.25 | 21.7 |
| 17.96 | 918.0 | 4.94 | 100.0 |
| 20.29 | 49.6 | 4.38 | 5.4 |
| 21.96 | 94.4 | 4.05 | 10.3 |
| 26.69 | 200.4 | 3.34 | 21.8 |

TABLE 44-continued

XRPD peak information of crystal form F and crystal form A of scutellarin aglycone

| Pos. [°2Th.] | Height [cts] | d-spacing [Å] | Rel. Int. [%] |
|---|---|---|---|
| 27.43 | 156.2 | 3.25 | 17.0 |
| 28.65 | 36.5 | 3.12 | 4.0 |
| 30.30 | 51.6 | 2.95 | 5.6 |

Toluene was added to obtain a suspension. After magnetic stirring at 50° C. for 6 days, the crystal form F and crystal form A were obtained. The peak information is shown in Table 45.

TABLE 45

XRPD peak information of crystal form F and crystal form A of scutellarin aglycone

| Pos. [°2Th.] | Height [cts] | d-spacing [Å] | Rel. Int. [%] |
|---|---|---|---|
| 14.66 | 29.2 | 6.04 | 19.1 |
| 18.05 | 153.1 | 4.92 | 100.0 |
| 22.11 | 34.0 | 4.02 | 22.2 |
| 26.74 | 116.0 | 3.33 | 75.8 |
| 27.50 | 90.1 | 3.24 | 58.9 |

Method 2: the mixture of the crystal form A and crystal form F obtained by suspending and stirring was heated to 370° C. and then cooled to the room temperature to obtain the product.

Figure 11:
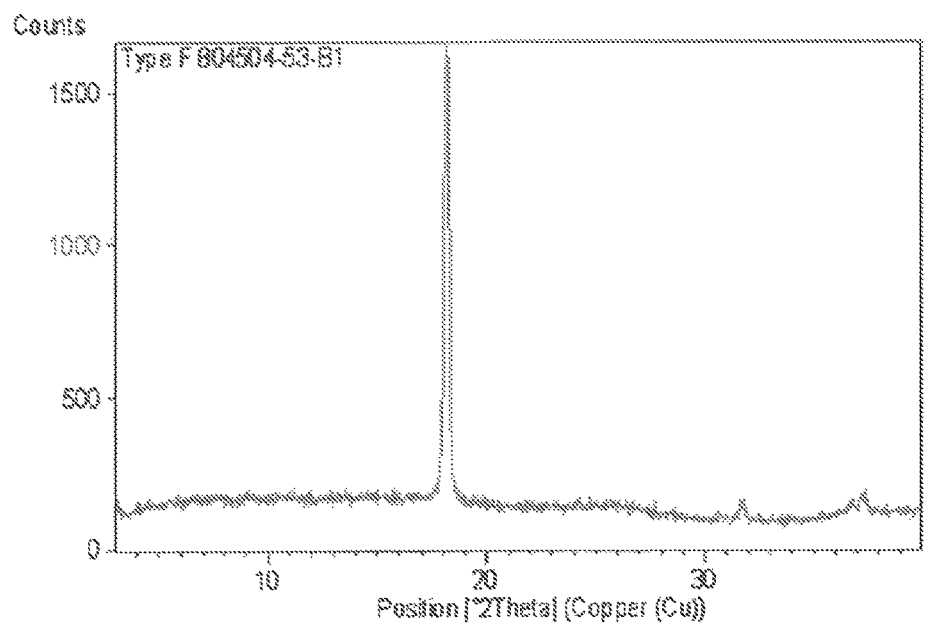
FIG. 11 shows the XRPD pattern of crystal form F of scutellarin aglycone.
Figure 12:
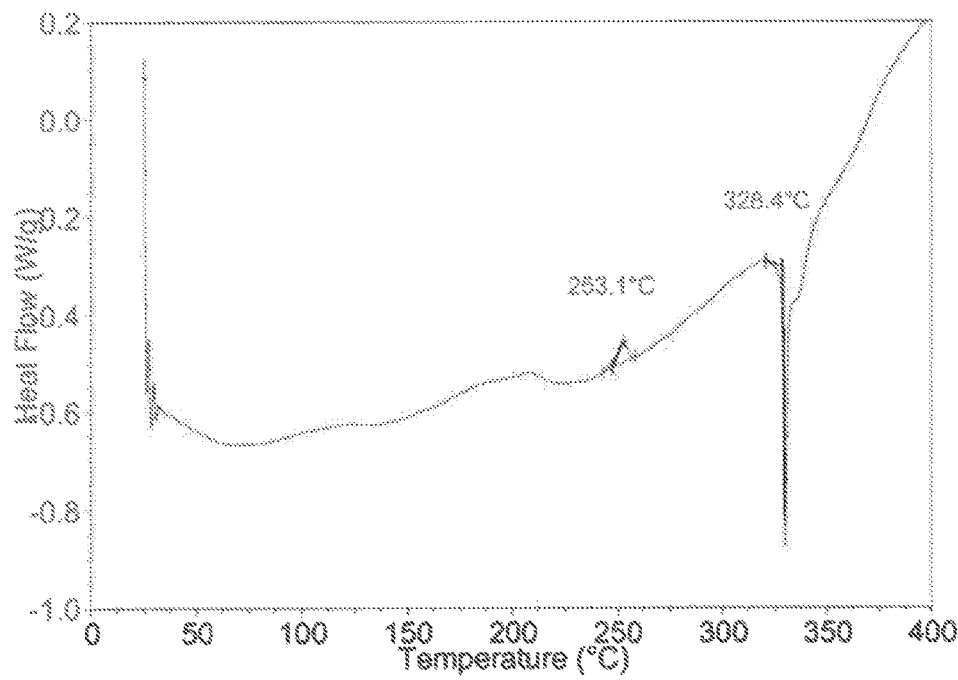
FIG. 12 shows the DSC thermogram of crystal form F of scutellarin aglycone.

The crystal form F prepared by Method 2 has a typical XRPD pattern shown in FIG. 11, and the peak information is shown in Table 46. The typical DSC thermogram of the crystal form F is shown in FIG. 12. The crystal form F has a melting range of (328.4° C.-331.5° C.), and a melting point of 328.4° C.

TABLE 46

XRPD peak information of crystal form F of scutellarin aglycone

| Pos. [°2Th.] | Height [cts] | d-spacing [Å] | Rel. Int. [%] |
|---|---|---|---|
| 18.07 | 1172.4 | 4.91 | 100.0 |
| 31.71 | 46.8 | 2.82 | 4.0 |
| 37.28 | 55.1 | 2.41 | 4.7 |

EXAMPLE 7

Preparation of Crystal Form G of Scutellarin Aglycone

Method 1: about 15 mg crystal form A of scutellarin aglycone was weighed and added to a 3 mL glass bottle, and 0.5~1.0 mL pyridine/heptane (at a volume ratio of 1:1) was added to obtain a clear solution. About 1.5 mg mixed polymer (a mixed polymer: prepared by mixing polyvinyl pyrrolidone (PVP), polyvinyl alcohol (PVA), polyvinyl acetate) (PVAc), polyvinyl chloride (PVC), hydroxypropyl methyl cellulose (HPMC) and methylcellulose (MC) at a mass ratio of 1:1:1:1:1:1) was added to the clear solution. The resultant solution was evaporated at room temperature slowly, to obtain the crystal form C. The peak information is shown in Table 47.

TABLE 47

XRPD peak information of crystal form G of scutellarin aglycone

| Pos. [°2Th.] | Height [cts] | d-spacing [Å] | Rel. Int. [%] |
|---|---|---|---|
| 6.80 | 159.2 | 13.00 | 11.8 |
| 7.22 | 226.7 | 12.25 | 16.8 |
| 8.27 | 1349.8 | 10.69 | 100.0 |
| 9.92 | 85.2 | 8.92 | 6.3 |
| 10.90 | 180.7 | 8.12 | 13.4 |
| 14.25 | 361.0 | 6.22 | 26.7 |
| 15.79 | 182.3 | 5.61 | 13.5 |
| 16.69 | 209.9 | 5.31 | 15.6 |
| 18.19 | 530.1 | 4.88 | 39.3 |
| 20.40 | 660.2 | 4.35 | 48.9 |
| 20.65 | 714.0 | 4.30 | 52.9 |
| 21.90 | 209.0 | 4.06 | 15.5 |
| 22.35 | 293.9 | 3.98 | 21.8 |
| 23.64 | 462.9 | 3.76 | 34.3 |
| 24.81 | 290.1 | 3.59 | 21.5 |
| 25.73 | 491.0 | 3.46 | 36.4 |
| 27.73 | 257.5 | 3.22 | 19.1 |
| 28.85 | 150.9 | 3.09 | 11.2 |
| 30.94 | 95.1 | 2.89 | 7.1 |
| 32.16 | 65.8 | 2.78 | 4.9 |
| 37.65 | 27.6 | 2.39 | 2.0 |

Method 2: about 10 mg crystal form A of scutellarin aglycone was weighed and added to a 3 mL glass bottle, and 0.5~1.25 mL pyridine or a mixed solvent of pyridine/methanol (at a volume ratio of 3:1) or pyridine/1,4-dioxane (at a volume ratio of 3:1) or pyridine/methyl tert-butyl ether (at a volume ratio of 3:1) or pyridine/2-methyl tetrahydrofuran (at a volume ratio of 3:1) or pyridine/toluene (at a volume ratio of 3:1) was added, to completely dissolve the sample to obtain a clear solution. The resultant solution was slowly evaporated at room temperature. After evaporation of the solvent to dryness, the obtained solid was the crystal form G.

Pyridine was added to obtain the crystal form G. The peak information is shown in Table 48.

TABLE 48

XRPD peak information of crystal form G of scutellarin aglycone

| Pos. [°2Th.] | Height [cts] | d-spacing [Å] | Rel. Int. [%] |
|---|---|---|---|
| 7.17 | 211.7 | 12.32 | 56.0 |
| 8.25 | 378.0 | 10.72 | 100.0 |
| 9.92 | 109.0 | 8.92 | 28.8 |
| 11.02 | 88.6 | 3.03 | 23.4 |
| 14.24 | 219.1 | 6.22 | 58.0 |
| 15.73 | 228.7 | 5.63 | 60.5 |
| 18.17 | 161.6 | 4.88 | 42.8 |
| 20.36 | 165.3 | 4.36 | 43.7 |
| 20.66 | 202.4 | 4.30 | 53.6 |
| 22.55 | 35.5 | 3.94 | 9.4 |
| 23.59 | 176.4 | 3.77 | 46.7 |
| 25.71 | 234.3 | 3.46 | 62.0 |
| 26.11 | 235.5 | 3.41 | 62.3 |
| 27.72 | 126.2 | 3.22 | 33.4 |

Pyridine/methanol (at a volume ratio of 3:1) was added to obtain the crystal form G. The peak information is shown in Table 49.

TABLE 49

XRPD peak information of crystal form G of scutellarin aglycone

| Pos. [°2Th.] | Height [cts] | d-spacing [Å] | Rel. Int. [%] |
|---|---|---|---|
| 6.89 | 183.7 | 12.83 | 9.6 |
| 7.32 | 186.0 | 12.09 | 9.7 |
| 8.35 | 1913.0 | 10.58 | 100.0 |
| 9.93 | 47.7 | 8.91 | 2.5 |
| 10.96 | 188.6 | 8.07 | 9.9 |
| 14.32 | 393.0 | 6.19 | 20.5 |
| 15.87 | 133.3 | 5.58 | 7.0 |
| 16.33 | 136.2 | 5.43 | 7.1 |
| 16.75 | 274.3 | 5.29 | 14.3 |
| 18.19 | 439.1 | 4.88 | 23.0 |
| 20.52 | 649.8 | 4.33 | 34.0 |
| 20.73 | 560.3 | 4.28 | 29.3 |
| 21.99 | 191.5 | 4.04 | 10.0 |
| 22.42 | 282.3 | 3.97 | 14.8 |
| 23.69 | 475.1 | 3.76 | 24.8 |
| 24.86 | 171.9 | 3.58 | 9.0 |
| 25.79 | 488.5 | 3.46 | 25.5 |
| 27.82 | 196.4 | 3.21 | 10.3 |
| 28.93 | 120.2 | 3.09 | 6.3 |
| 30.97 | 63.4 | 2.89 | 3.3 |
| 32.32 | 30.8 | 2.77 | 1.6 |

Pyridine/1,4-dioxane (at a volume ratio of 3:1) was added to obtain the crystal form G. The peak information is shown in Table 50.

TABLE 50

XRPD peak information of crystal form G of scutellarin aglycone

| Pos. [°2Th.] | Height [cts] | d-spacing [Å] | Rel. Int. [%] |
|---|---|---|---|
| 6.84 | 100.3 | 12.92 | 15.8 |
| 7.21 | 201.0 | 12.25 | 31.6 |
| 8.28 | 635.9 | 10.68 | 100.0 |
| 9.91 | 62.2 | 8.93 | 9.8 |
| 10.95 | 102.1 | 8.08 | 16.1 |
| 14.25 | 298.2 | 6.22 | 46.9 |
| 15.74 | 127.5 | 5.63 | 20.1 |
| 16.69 | 94.3 | 5.31 | 14.8 |
| 18.18 | 266.3 | 4.88 | 41.9 |
| 20.41 | 345.4 | 4.35 | 54.3 |
| 20.66 | 196.3 | 4.30 | 30.9 |
| 22.32 | 96.0 | 3.98 | 15.1 |
| 23.58 | 238.7 | 3.77 | 37.5 |
| 24.97 | 83.1 | 3.57 | 13.1 |
| 25.71 | 300.2 | 3.47 | 47.2 |
| 27.80 | 81.2 | 3.21 | 12.8 |
| 30.92 | 33.7 | 2.89 | 5.3 |

Pyridine/methyl tert-butyl ether (at a volume ratio of 3:1) was added to obtain the crystal form G. The peak information is shown in Table 51.

TABLE 51

XRPD peak information of crystal form G of scutellarin aglycone

| Pos. [°2Th.] | Height [cts] | d-spacing [Å] | Rel. Int. [%] |
|---|---|---|---|
| 6.80 | 47.6 | 12.99 | 24.3 |
| 8.33 | 118.0 | 10.61 | 60.3 |
| 9.94 | 76.1 | 8.89 | 38.9 |
| 11.10 | 70.5 | 7.97 | 36.0 |
| 14.21 | 115.3 | 6.23 | 58.9 |
| 15.77 | 157.2 | 5.62 | 80.3 |
| 18.28 | 81.6 | 4.85 | 41.7 |
| 20.58 | 47.6 | 4.32 | 24.3 |
| 22.20 | 18.6 | 4.00 | 9.5 |
| 23.65 | 92.3 | 3.76 | 47.1 |
| 25.79 | 195.7 | 3.45 | 100.0 |
| 26.25 | 180.3 | 3.39 | 92.1 |
| 28.03 | 92.4 | 3.18 | 47.2 |

Pyridine/2-methyl tetrahydrofuran (at a volume ratio of 3:1) was added to obtain the crystal form G. The peak information is shown in Table 52.

TABLE 52

XRPD peak information of crystal form G of scutellarin aglycone

| Pos. [°2Th.] | Height [cts] | d-spacing [Å] | Rel. Int. [%] |
|---|---|---|---|
| 6.85 | 74.4 | 12.91 | 10.7 |
| 8.33 | 694.4 | 10.62 | 100.0 |
| 11.01 | 75.4 | 8.04 | 10.9 |
| 14.32 | 168.8 | 6.19 | 24.3 |
| 16.77 | 75.2 | 5.29 | 10.8 |
| 18.26 | 222.2 | 4.86 | 32.0 |
| 20.47 | 273.2 | 4.34 | 39.4 |
| 22.32 | 42.3 | 3.98 | 6.1 |
| 22.72 | 63.1 | 3.91 | 9.1 |
| 23.65 | 148.7 | 3.76 | 21.4 |
| 25.77 | 117.8 | 3.46 | 17.0 |
| 27.78 | 33.0 | 3.21 | 4.8 |
| 28.88 | 33.6 | 3.09 | 4.8 |

Pyridine/toluene (at a volume ratio of 3:1) was added to obtain the crystal form G. The peak information is shown in Table 53.

TABLE 53

XRPD peak information of crystal form G of scutellarin aglycone

| Pos. [°2Th.] | Height [cts] | d-spacing [Å] | Rel. Int. [%] |
|---|---|---|---|
| 8.35 | 731.4 | 10.58 | 100.0 |
| 9.98 | 75.3 | 8.86 | 10.3 |
| 10.97 | 107.1 | 8.07 | 14.6 |
| 14.21 | 123.9 | 6.23 | 16.9 |
| 15.79 | 189.4 | 5.61 | 25.9 |
| 16.75 | 94.1 | 5.29 | 12.9 |
| 18.22 | 165.9 | 4.87 | 22.7 |
| 20.45 | 142.1 | 4.34 | 19.4 |
| 22.40 | 75.5 | 3.97 | 10.3 |
| 23.67 | 103.8 | 3.76 | 14.2 |
| 25.76 | 128.2 | 3.46 | 17.5 |
| 26.16 | 157.3 | 3.41 | 21.5 |
| 28.11 | 74.9 | 3.17 | 10.2 |

Figure 13:
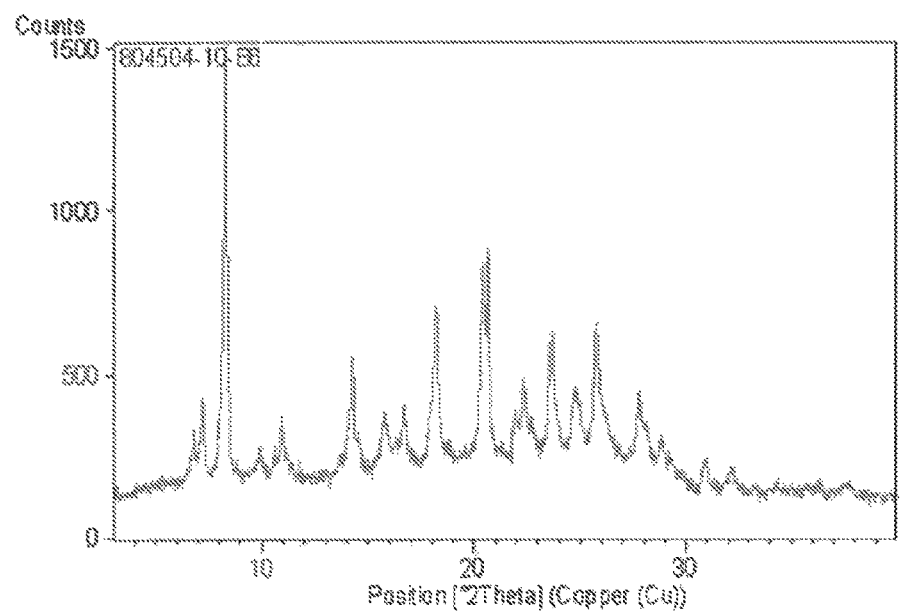
FIG. 13 shows the XRPD pattern of crystal form G of scutellarin aglycone.
Figure 14:
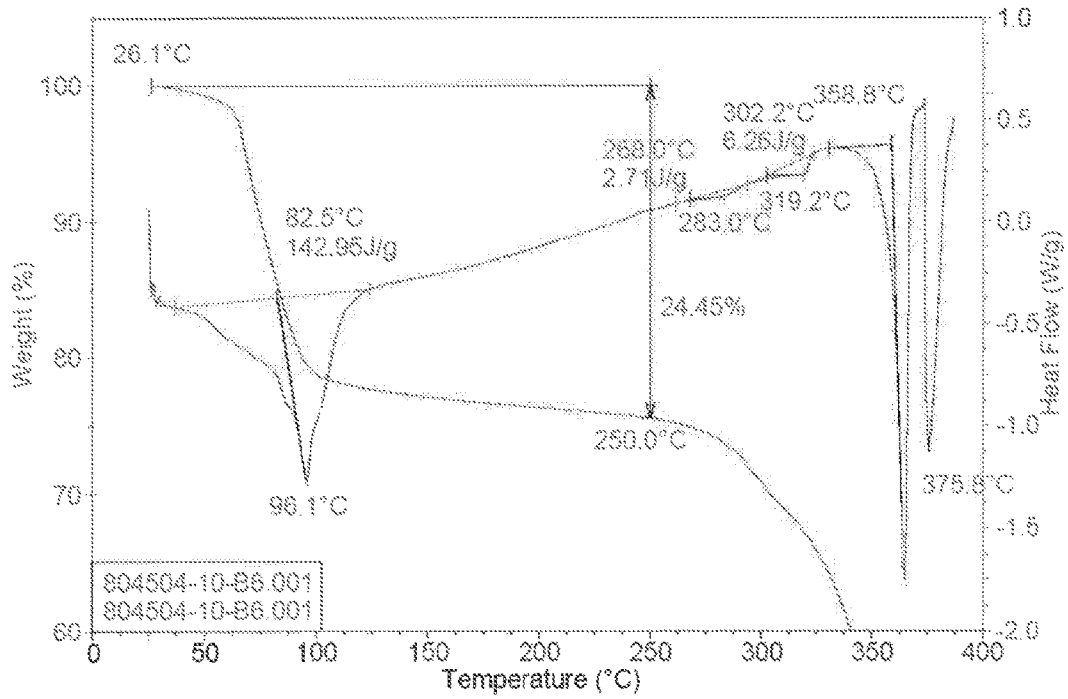
FIG. 14 shows the TGA and DSC thermograms of crystal form G of scutellarin aglycone.

The crystal form G prepared by Method 1 has a typical XRPD pattern shown in FIG. 13, peak information is shown in Table 54, and typical TGA and DSC thermograms are shown in FIG. 14. The crystal form G has a melting range of (358.8° C.-375.8° C.) and (367.2° C.-383.1° C.) and a melting point of 358.8° C. and 367.2° C.

TABLE 54

XRPD peak information of crystal form G of scutellarin aglycone

| pos. [°2Th.] | Height [cts] | d-spacing [Å] | Rel. Int. [%] |
|---|---|---|---|
| 6.80 | 159.2 | 13.00 | 11.8 |
| 7.22 | 226.7 | 12.25 | 16.8 |
| 8.27 | 1349.8 | 10.69 | 100.0 |

TABLE 54-continued

XRPD peak information of crystal form G of scutellarin aglycone

| pos. [°2Th.] | Height [cts] | d-spacing [Å] | Rel. Int. [%] |
|---|---|---|---|
| 9.92 | 85.2 | 8.92 | 6.3 |
| 10.90 | 180.7 | 8.12 | 13.4 |
| 14.25 | 361.0 | 6.22 | 26.7 |
| 15.79 | 182.3 | 5.61 | 13.5 |
| 16.69 | 209.9 | 5.31 | 15.6 |
| 18.19 | 530.1 | 4.88 | 39.3 |
| 20.65 | 714.0 | 4.30 | 52.9 |
| 21.90 | 209.0 | 4.06 | 15.5 |
| 22.35 | 293.9 | 3.98 | 21.8 |
| 23.64 | 462.9 | 3.76 | 34.3 |
| 24.81 | 290.1 | 3.59 | 21.5 |
| 25.73 | 491 | 3.46 | 36.4 |
| 27.73 | 257.5 | 3.22 | 19.1 |
| 28.85 | 150.9 | 3.09 | 11.2 |
| 30.94 | 95.1 | 2.89 | 7.1 |
| 32.16 | 65.8 | 2.78 | 4.9 |
| 37.65 | 27.6 | 2.39 | 2 |

EXAMPLE 8

Preparation of Crystal Form H of Scutellarin Aglycone

About 100 mg crystal form A of scutellarin aglycone was weighed, and dissolved in 8 mL pyridine/ethyl acetate (3:1, v/v). The resultant solution was evaporated at room temperature with the bottle's mouth open to obtain the crystal form D. The obtained crystal form D was dissolved in 2 mL pyridine/ethyl acetate (3:1, v/v). After evaporation at room temperature for 3 days, the crystal form H was obtained. The crystal form H could be obtained by dissolving the crystal form D obtained by other methods in 2 mL pyridine/ethyl acetate (3:1, v/v) and evaporating at room temperature for 3 days.

Figure 15:
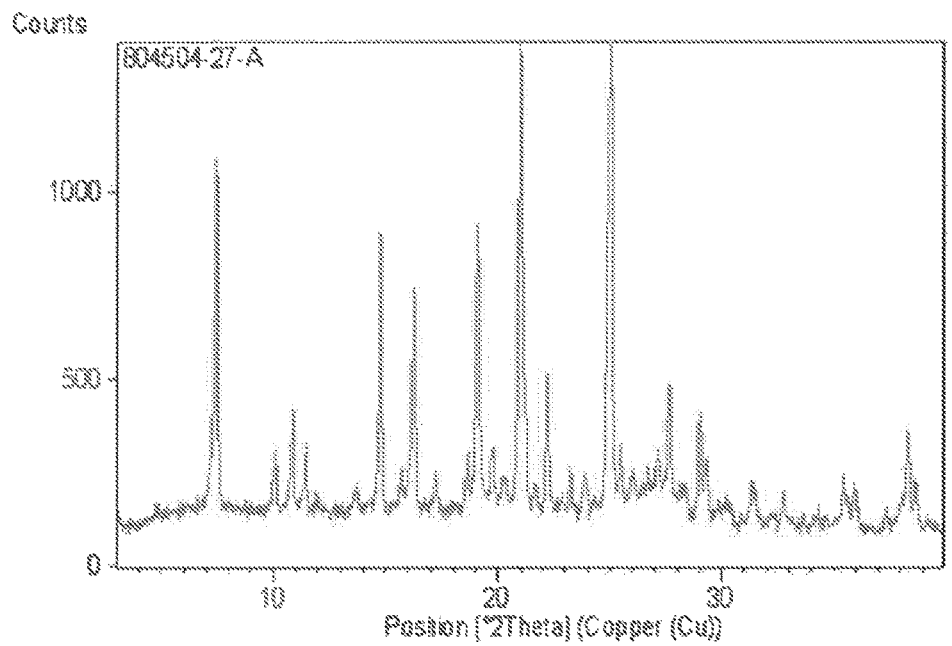
FIG. 15 shows the XRPD pattern of crystal form H of scutellarin aglycone.
Figure 16:
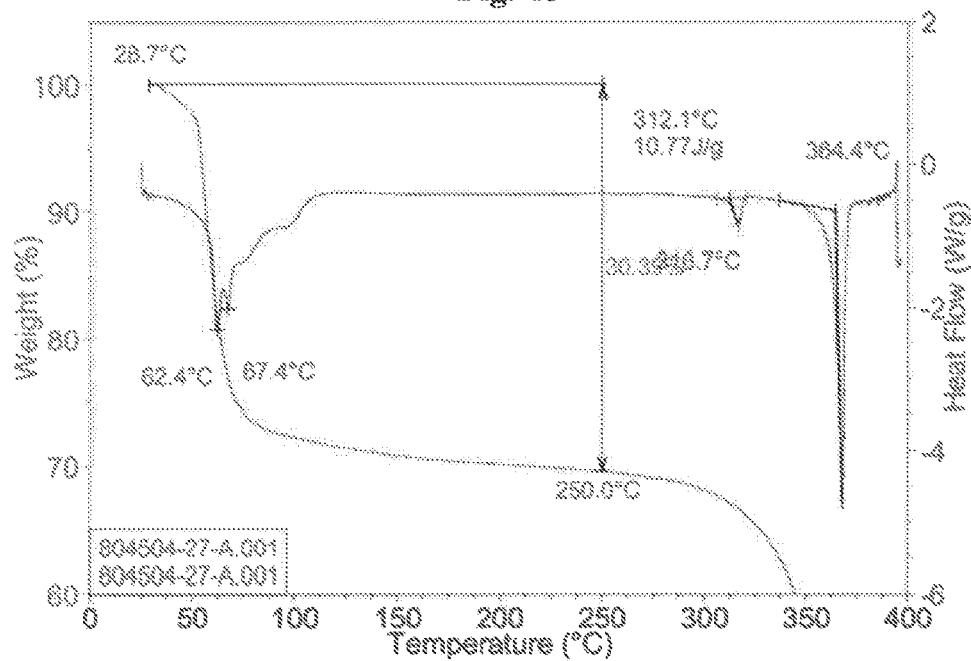
FIG. 16 shows the TGA and DSC thermograms of crystal form H of scutellarin aglycone.

The crystal form H has a typical XRPD pattern shown in FIG. 15 peak information is shown in Table 55, and typical TGA and DSC thermograms are shown in FIG. 16. The crystal form H has a melting range of (364.4° C.-369.3° C.) and a melting point of 364.4° C.

TABLE 55

XRPD peak information of crystal form H of scutellarin aglycone

| Pos. [°2Th.] | Height [cts] | d-spacing [Å] | Rel. Int. [%] |
|---|---|---|---|
| 7.44 | 934.6 | 11.89 | 73.5 |
| 10.07 | 166.1 | 8.78 | 13.1 |
| 10.86 | 278.1 | 8.14 | 21.9 |
| 11.48 | 174.4 | 7.71 | 13.7 |
| 13.67 | 66.3 | 6.48 | 5.2 |
| 14.81 | 666.3 | 5.98 | 52.4 |
| 15.66 | 108.4 | 5.66 | 8.5 |
| 16.22 | 607.8 | 5.46 | 47.8 |
| 17.23 | 109.8 | 5.15 | 8.6 |
| 18.60 | 169.0 | 4.77 | 13.3 |
| 19.08 | 785.3 | 4.65 | 61.8 |
| 19.77 | 185.3 | 4.49 | 14.6 |
| 20.23 | 98.5 | 4.39 | 7.8 |
| 20.96 | 1271.3 | 4.24 | 100.0 |
| 21.71 | 75.8 | 4.09 | 6.0 |
| 22.21 | 378.8 | 4.00 | 29.8 |
| 23.23 | 142.2 | 3.83 | 11.2 |
| 23.88 | 117.7 | 3.73 | 9.3 |
| 25.04 | 1226.1 | 3.56 | 96.5 |
| 25.48 | 203.4 | 3.50 | 16.0 |
| 25.96 | 129.5 | 3.43 | 10.2 |
| 27.12 | 168.1 | 3.29 | 13.2 |
| 27.66 | 332.5 | 3.23 | 26.2 |
| 28.36 | 94.1 | 3.15 | 7.4 |
| 28.99 | 284.9 | 3.08 | 22.4 |
| 29.31 | 178.5 | 3.05 | 14.0 |
| 30.20 | 66.4 | 2.96 | 5.2 |
| 31.38 | 104.1 | 2.85 | 8.2 |
| 32.71 | 73.6 | 2.74 | 5.8 |
| 35.44 | 133.2 | 2.53 | 10.5 |
| 35.95 | 121.6 | 2.50 | 9.6 |
| 37.33 | 39.7 | 2.41 | 3.1 |
| 38.34 | 270.0 | 2.35 | 21.2 |
| 38.67 | 124.0 | 2.33 | 9.8 |

EXAMPLE 9

Preparation of Crystal Form I of Scutellarin Aglycone

About 50 mg scutellarin aglycone crystal form A was weighed and dissolved in 2 mL pyridine/ethyl acetate (3:1 v/v). After evaporation at room temperature for 6 days, the crystal form I was obtained.

Figure 17:
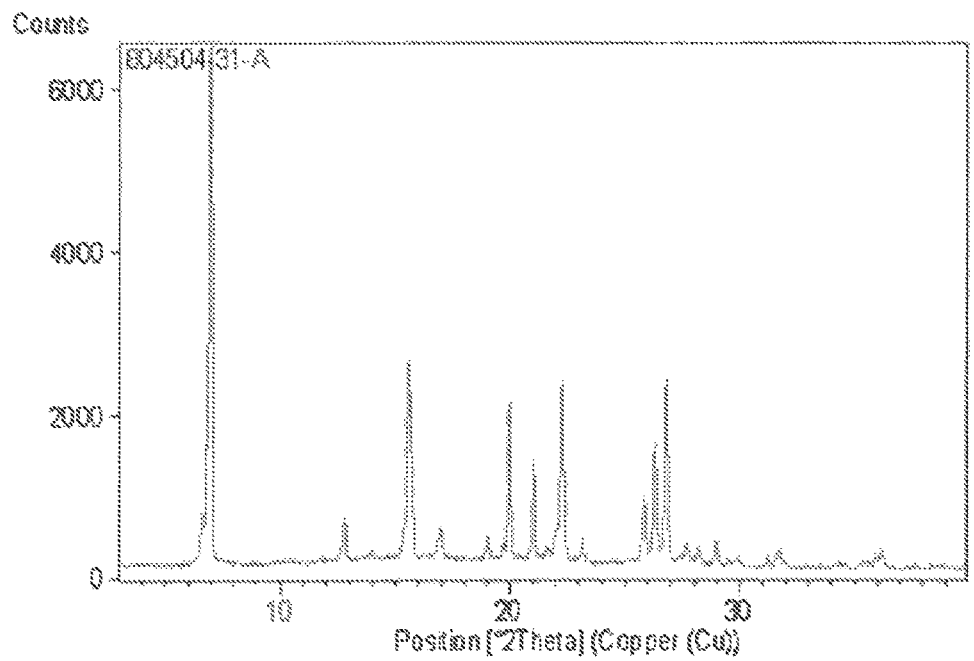
FIG. 17 shows the XRPD pattern of crystal form I of scutellarin aglycone.
Figure 18:
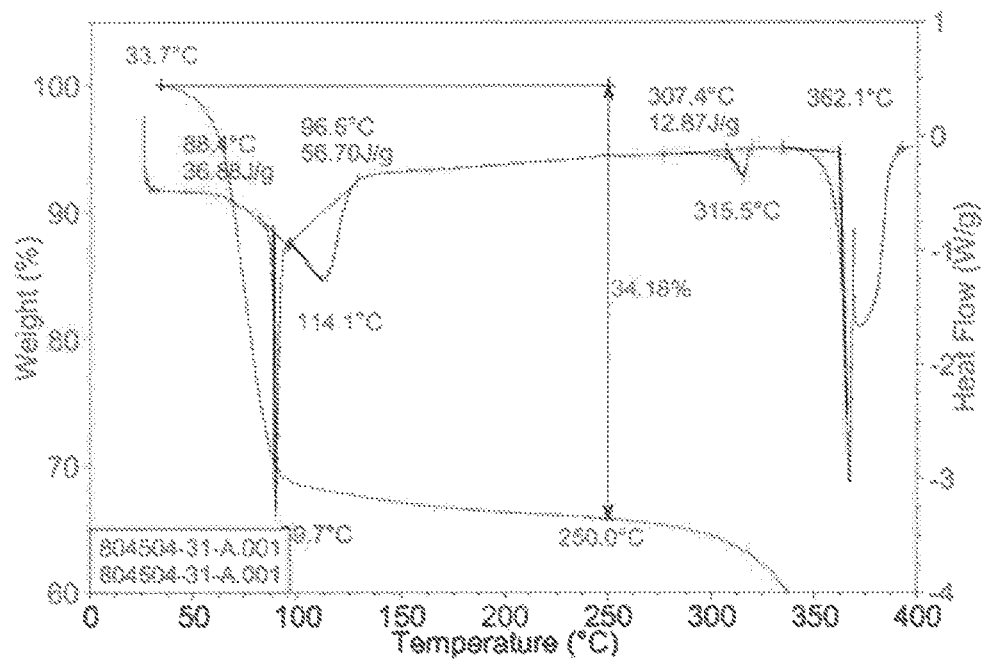
FIG. 18 shows the TGA and DSC thermograms of crystal form I of scutellarin aglycone.

The crystal form I has a typical XRPD pattern shown in FIG. 17, the peak information is shown in Table 56, and typical TGA and DSC thermograms are shown in 18. The crystal form I has a melting range of (362.1° C.-368.9° C.), and a melting point of 362.1° C.

TABLE 56

XRPD peak information of crystal form I of scutellarin aglycone

| Pos. [°2Th.] | Height [cts] | d-spacing [Å] | Rel. Int. [%] |
|---|---|---|---|
| 6.57 | 638.8 | 13.46 | 10.7 |
| 6.93 | 5964.6 | 12.76 | 100.0 |
| 12.81 | 507.0 | 6.91 | 8.5 |
| 13.98 | 131.7 | 6.34 | 2.2 |
| 15.57 | 2487.7 | 5.69 | 41.7 |
| 16.99 | 440.5 | 5.22 | 7.4 |
| 19.03 | 345.4 | 4.66 | 5.8 |
| 19.94 | 1915.9 | 4.45 | 32.1 |
| 21.04 | 1292.2 | 4.22 | 21.7 |
| 21.68 | 194.3 | 4.10 | 3.3 |
| 22.02 | 444.0 | 4.04 | 7.4 |
| 22.32 | 2219.5 | 3.98 | 37.2 |
| 23.19 | 343.5 | 3.84 | 5.8 |
| 25.85 | 846.1 | 3.45 | 14.2 |
| 26.29 | 1491.6 | 3.39 | 25.0 |
| 26.79 | 2292.8 | 3.33 | 38.4 |
| 27.69 | 259.4 | 3.22 | 4.4 |
| 28.18 | 254.8 | 3.17 | 4.3 |
| 28.96 | 307.3 | 3.08 | 5.2 |
| 29.50 | 86.2 | 3.03 | 1.5 |
| 29.92 | 131.3 | 2.99 | 2.2 |
| 31.22 | 124.7 | 2.87 | 2.1 |
| 31.71 | 239.2 | 2.82 | 4.0 |
| 34.34 | 58.8 | 2.61 | 1.0 |
| 35.38 | 69.2 | 2.54 | 1.2 |
| 35.92 | 171.8 | 2.50 | 2.9 |
| 36.19 | 254.5 | 2.48 | 4.3 |
| 37.67 | 43.2 | 2.39 | 0.7 |
| 38.59 | 33.6 | 2.33 | 0.6 |

EXAMPLE 10

Preparation of Crystal Form of Scutellarin Aglycone's Ammonium Salt

Method 1: about 20 mg sample of crystal form A was weighed and added to a 1.5 mL glass bottle. Ammonia water was added at a molar ratio of 1:1, and 0.5 mL acetone was added to obtain a suspension. After magnetic stirring at room temperature (RT) for 6 days (after 2 days, most of the solid was determined to be crystal form A of free acid), the solid was separated by centrifugation as the crystal form A of the aglycone and the crystal form of aglycone's ammonium salt.

Method 2: alternatively, 500 mg sample of crystal form A and 17.5 mL 0.1 mol/L ammonia water were placed in a 20 mL vial. After suspending and stirring at room temperature for about 48 h, the solid was separated by centrifugation and subjected to XRPD, and the solid still comprised crystal form A of free acid. 0.1 mol/L ammonia water was added to the initial volume, followed by further stirring. 0.1 mol/L ammonia water was added to the initial volume when the volume of ammonia water decreased, followed by further stirring. After 15 days, it was completely converted to ammonium salt. The total volume of 0.1 mol/L ammonia water added was about 10 mL (0.1 mol/L ammonia water was prepared by strong ammonia water and acetone).

Figure 19:
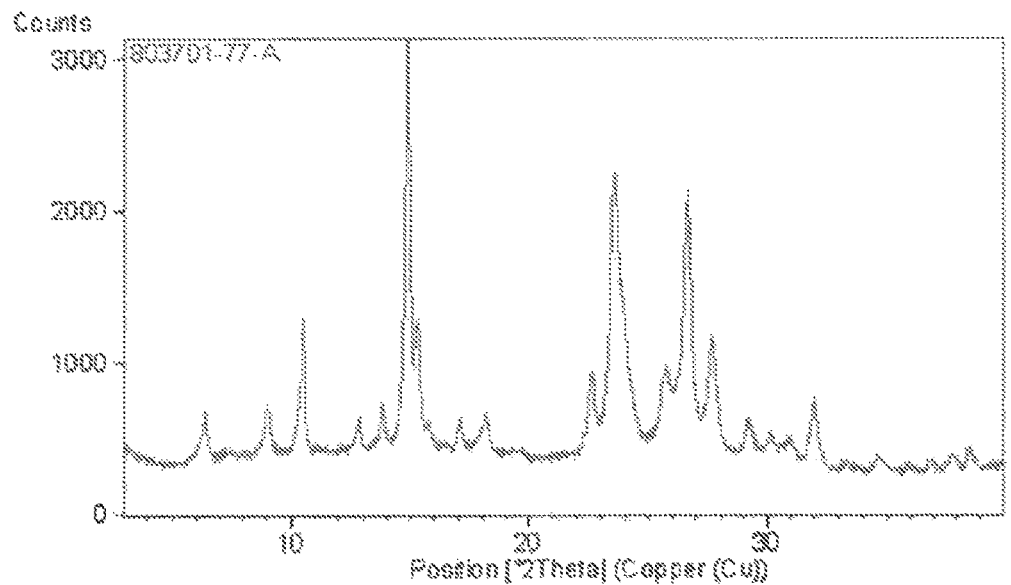
FIG. 19 shows the XRPD pattern of the crystal form of scutellarin aglycone's ammonium salt hydrate.
Figure 20:
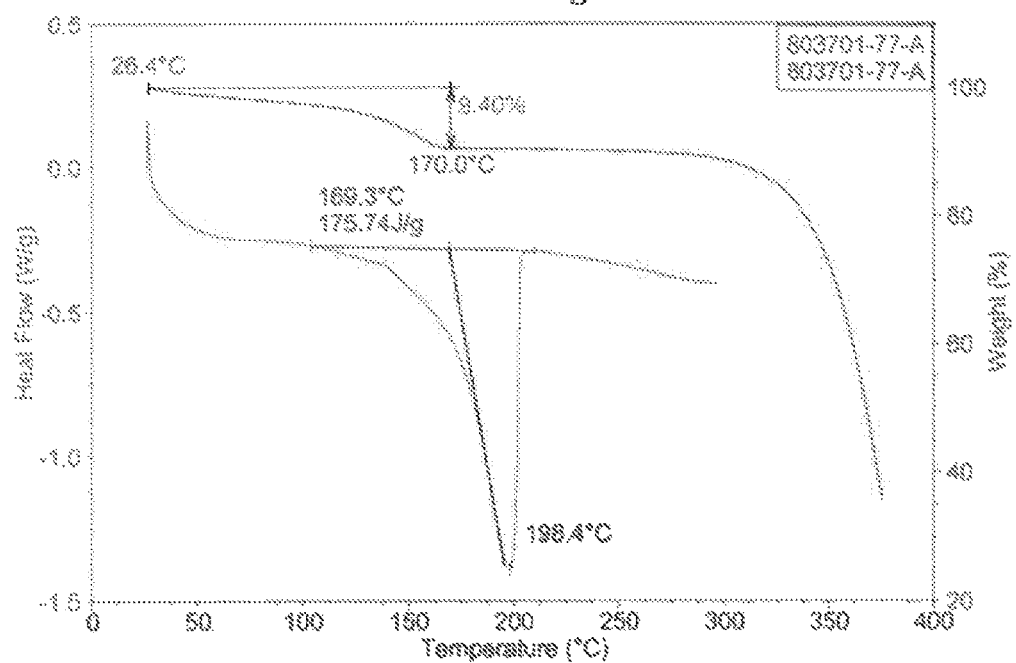
FIG. 20 shows the TGA and DSC thermograms of the crystal form of scutellarin aglycone's ammonium salt hydrate.

The crystal form of scutellarin aglycone's ammonium salt prepared by Method 1 has a typical XRPD pattern shown in FIG. 19, and the peak information of the pattern is shown in Table 57. The typical TGA and DSC thermograms of the crystal form of the ammonium salt are shown in FIG. 20, and no sharp melting point is observed.

TABLE 57

XRPD peak information of crystal form of scutellarin aglycone's ammonium salt

| Pos. [°2Th.] | Height [cts] | d-spacing [Å] | Rel. Int. [%] |
|---|---|---|---|
| 6.38 | 336.8 | 13.84 | 12.7 |
| 9.03 | 354.7 | 9.80 | 13.3 |
| 10.52 | 910.8 | 8.41 | 34.2 |
| 12.82 | 278.5 | 6.90 | 10.5 |
| 13.83 | 344.6 | 6.40 | 13.0 |
| 14.86 | 2660.6 | 5.96 | 100.0 |
| 15.32 | 905.5 | 5.78 | 34.0 |
| 17.08 | 239.0 | 5.19 | 9.0 |
| 18.19 | 257.0 | 4.88 | 9.7 |
| 22.65 | 563.1 | 3.93 | 21.2 |
| 23.62 | 1819.3 | 3.77 | 68.4 |
| 25.70 | 618.8 | 3.47 | 23.3 |
| 26.62 | 1744.3 | 3.35 | 65.6 |
| 27.70 | 797.9 | 3.22 | 30.0 |
| 29.13 | 286.2 | 3.07 | 10.8 |
| 30.10 | 207.1 | 2.97 | 7.8 |
| 31.98 | 437.3 | 2.80 | 16.4 |
| 34.76 | 68.0 | 2.58 | 2.6 |
| 37.81 | 87.9 | 2.38 | 3.3 |
| 38.51 | 136.5 | 2.34 | 5.1 |

EXAMPLE 11

Analysis of the Crystal Forms and HPLC Results

XRPD is mainly used to determine the crystal forms of a compound, and provides the characteristic diffraction peak information for the crystal forms of a compound. TGA determines the weight loss during the heating of a crystal, and mainly provides the information concerning whether a sample is present in the form of solvate or not.

It is found by TGA that the crystal forms A, D, E, and F are anhydrous crystal forms, and the other crystal forms are solvate crystal forms, and it is further found by GC and HNMR analysis that the other crystal forms are pyridine complex crystal forms.

Crystal form B: the TGA result shows that when crystal form B was heated to 250° C., a weight loss of 17.0% was determined, and the GC result of a sample of crystal form B shows that 18.0% of the sample was pyridine, and after removing the solvent by heating, crystal form B was converted to crystal form D, indicating that crystal form B was a pyridine solvate.

Figure 21:
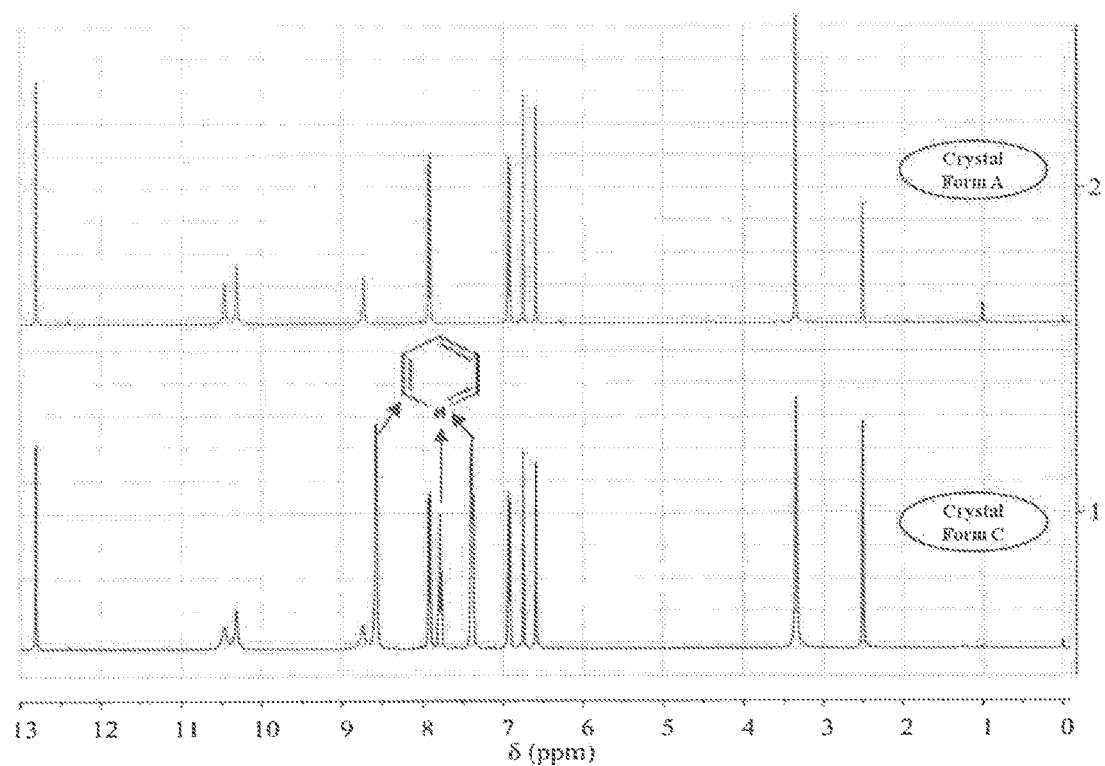
FIG. 21 shows the 1H-NMR comparison spectra of crystal form A and crystal form C.

Crystal form C: the TGA result shows that when crystal form C was heated to 250° C., a weight loss of 33.0% was determined, and the GC result of a sample of crystal form C shows that pyridine accounted for 36.4%, and after removing the solvent by heating, crystal form C was converted to crystal form D, indicating that crystal form C was a pyridine solvate. The 1H-NMR comparison spectra of crystal form C and crystal form A are shown in FIG. 21, and the result shows that as compared to the sample of crystal form A, the sample of crystal form C further had three peaks (739, 7.79, 8.58 ppm), which were resulted from the hydrogens of pyridine in deuterated-DMSO, also indicating that the sample of crystal form C was a pyridine solvate, and no degraded product was contained in the sample of crystal form C.

Crystal form G: the DSC and TGA results show that during the heating of crystal form G, the endothermic peak may be resulted from desolvation, and the other endothermic peak may be resulted from crystal transformation or melting. TGA shows that a weight loss of 24.5% was determined in the sample. The GC result of crystal form G shows that crystal form G comprised pyridine, and after removing the solvent by heating, crystal form G was converted to crystal form D indicating that crystal form C was a pyridine solvate.

Figure 22:
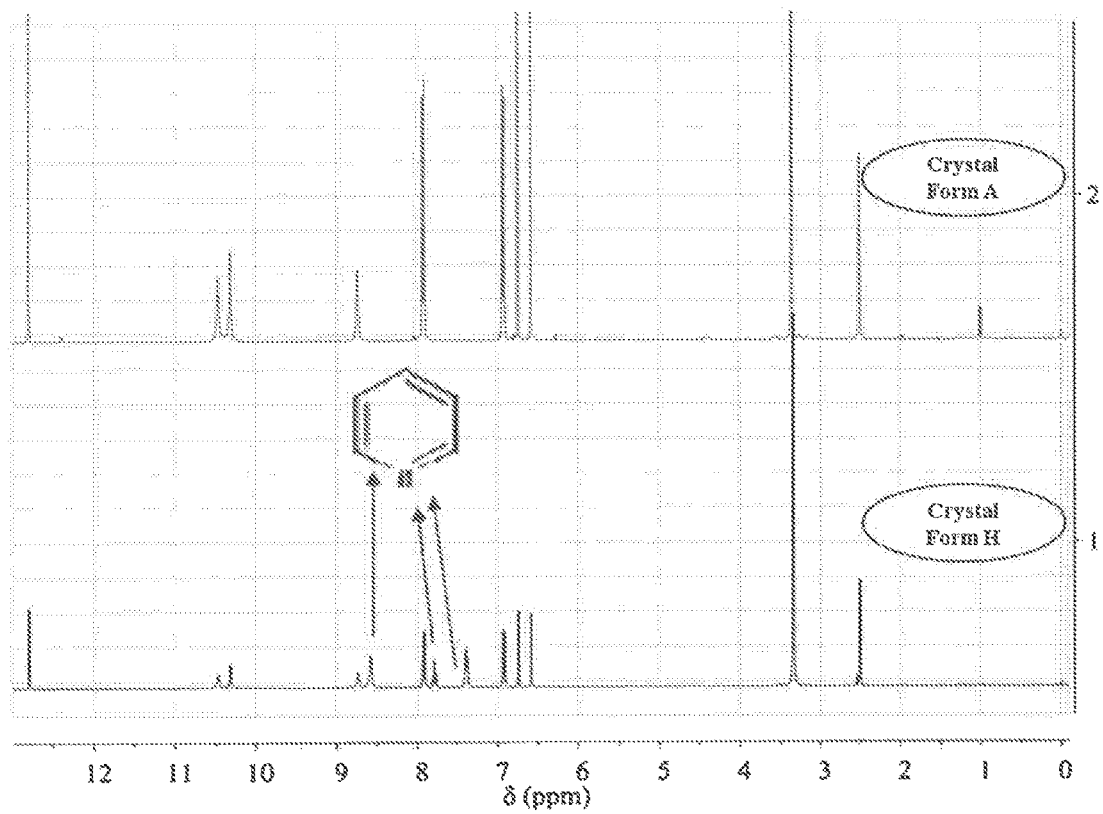
FIG. 22 shows the 1H-NMR comparison spectra of crystal form A and crystal form H.

Crystal form H: the DSC and TGA thermograms of crystal form H show that it has endothermic peaks resulted from desolvation, crystal transformation and melting during the heating of the sample; and the TGA shows that a weight loss of ~30.4% was determined. The 1H-NMR comparison spectra of a sample of crystal form H and a sample of crystal form A are shown in FIG. 22. The result shows that as compared to the sample of crystal form A, the sample of crystal form H further had three peaks (7.39, 7.79, 8.58 ppm), which were resulted from the hydrogens of pyridine in deuterated-DMSO, also indicating that no degraded product was contained in the sample of crystal form H. After removing the solvent by heating, crystal form H was converted to crystal form D, indicating that crystal form H was a pyridine solvate.

Crystal form I: the DSC and TGA thermograms of crystal form I show that during the heating of the sample, desolvation, crystal transformation and melting resulted in multiple endothermic peaks, and TGA shows that a weight loss of about 34.2% was determined in the sample. The GC result of crystal form I shows that crystal form I comprised pyridine, and after removing the solvent by heating, crystal form I was converted to crystal form D, indicating that crystal form I was a pyridine solvate.

DSC is used to monitor the melting point of a sample when heated, so as to obtain the data on the melting point of the sample.

It was determined by HPLC that except for crystal forms F, H and I, the other crystal forms had a purity of above 95%.

HPLC method is shown in Table 58:

TABLE 58

HPLC Test

| HPLC method | Parameters |
|---|---|
| Instrument | Agilent 1100 with DAD detector |
| Column | Agela venusil AQ C18, 4.6 × 150 mm, 3 μm |
| Mobile phase | A: 0.05% TFA in water |
| | B: 0.05% TFA in methanol |

| Gradient | Time (min) | B % |
|---|---|---|
| | 0.0 | 10 |
| | 35.0 | 95 |
| | 37.0 | 95 |
| | 37.1 | 10 |
| | 40.0 | 10 |

| | |
|---|---|
| Flow rate | 1 ml/min |
| Wavelength | UV@210 nm & 280 nm |
| Injection volume | 5 ul |
| Run time | 40 min |
| Column temperature | 40° C. |
| Sample temperature | RT |
| diluent | Methanol |

The results of HPLC are shown in Table 59:

TABLE 59

HPLC Results

| Crystal form | Retention time (min) | Purity/% |
|---|---|---|
| Crystal form A | 21.82 | 97.27 |
| Crystal form B | 21.97 | 94.32 |
| Crystal form C | 21.95 | 99.17 |
| Crystal form D | 21.83 | 96.94 |
| Crystal form E | 21.94 | 99.03 |
| Crystal form F and Crystal form A | 21.97 | 97.76 |
| Crystal form G | 21.93 | 95.48 |

Note:
since crystal forms F, H, and I were obtained in a small amount, they are not subjected to HPLC analysis.

By multiple detection means such as XRPD, TGA and DSC, said 10 crystal forms can be qualitative described.

At about 330° C., crystal form A and crystal form D can be converted to crystal form E, while when the room temperature is below 50° C., crystal forms A, D, and E are the most stable crystal forms. It is found by determining the solubility in isopropanol that their solubility is as follows: crystal form A>crystal form D>crystal form E.

The crystal form of scutellarin aglycone's ammonium salt is a hydrate, and its melting point is not detected. The advantage is that the aglycone salt itself has a good stability, and no significant degradation is observed.

EXAMPLE 12

Assay on Activity of Crystal Form A of Scutellarin Aglycone

1. Experimental Materials

Test drug; scutellarin aglycone (called aglycone hereafter for short): brownish green powder, with a batch number of 20120206, which was crystal form A, prepared by the method described in Example 1. In the experiment, it was used in a dose of 45.8 mg/kg (which was 6-fold of the intended dose in clinical treatment);

Reagents and drugs: triphenyltetrazolium chloride (TTC), a product from Sigma Company, with a batch number of 120K5305; 0.5% injection, with a batch Dumber of 12020604, produced by Kunming Yusi Pharmaceutical Co., Ltd. Chloral hydrate (a batch number of T20061114, Sinopharm Chemical Reagent Co., Ltd.); MDA kit (a batch number of 20120401), SOD kit (a batch number of 20120401), nitric oxide (NO) kit (a batch number of 20120401), and Protein Quantitation Kit (a batch number of 20120401), provided by Nanjing Jiancheng Bioengineering Institute.

Experimental Apparatus:

UV-2501 UV Spectrophotometer (produced by Shimadzu Corporation); Centrifuge 5810R Refrigerated Centrifuge (German Eppendoff Company); BS110 type electronic analytical balance (Sartorius Company); COOLPIXS550 digital camera, a Nikon product. Medical Microscopic Image Compute-aided Analysis System (MIAS) (Image Center of Beihang University).

Experimental Animal and Feeding Conditions

SD male rat, weighed 250±20 g, Center of Medical Laboratory Animal of Guangdong Province. Animal certificate number: SCXK (Yue) 2008-0002. Feed license: SCXK (Dian) 20050009: raised in Animal Laboratory of Natural Medicine Screening Research Center of Yunnan Institute of Materia Medica. Animal laboratory, temperature: 20~26° C.(daily temperature difference ≤4° C.); humidity: 40%~70%; air change rate: 10~20 times/h; airflow rate: 0.1~0.2 m/s; noise: ≤60 dB; working illuminance: 150~300 lx, animal illuminance: 15~20 lx; lighting: 12:12 h light-dark alternation.

2. Experimental Method 2.1 Model Establishment

SD male rat was fasted one night, with free access to water. At the day of experiment, the rat was anesthetized by intraperitoneal injection of 35% chloral hydrate (350 mg/kg), and fixed on its back. The skin was incised along the neck median line to expose the carotid artery at the right side, and the internal and external carotid artery were separated. 3# nylon wire (a diameter of 0.285 mm) was inserted from the free end of the external carotid artery, introduced into the internal carotid artery from the distal end of the external carotid artery, and inserted at the artery of Willis's circle in brain, to effectively occlude the middle cerebral artery. The inserted nylon wire was 18~20 mm away from carotid artery bifurcation. The free end of the external carotid artery and the intra cavitary nylon wire were ligated, to prevent bleeding. The subcutaneous fascia and skin were sewn up layer by layer, and antibiotics were topically added dropwise to prevent infection. After middle cerebral artery occlusion (MCAO) for 2 h, the nylon wire was carefully drawn out from the internal carotid artery, and the internal carotid artery was subjected to reperfusion. The rats, in which no significant hemiplegia was observed at the right upper limb, were excluded from the experiment. The animals were grouped depending on the score of nerve function.

2.2 Administration

Three groups were classified in the experiment, 15 animals for each group. The three groups were a sham-operated group, a model control group, and a scutellarin aglycone (45.8 mg/kg) group, respectively. In the sham-operated group and the model control group, an equal volume of 0.3% sodium carboxymethyl cellulose (CMC-Na) was administered. In all of the sham-operated group, the model control group, and the scutellarin aglycone group, intragastric administration was continuously performed for 4 times, and then administration was performed once at each of 1 h, 12 h, 24 h, 36 h after reperfusion, wherein the volume for intragastric administration in rat was 1 mL/100 g.

2.3 Indexes 2.3.1 Evaluation of the degree of nerve function impairment: the behavioral disorder of the animal was scored by double blind method at 1 h (before administration), 12 h, 24 h, 36 h, 48 h after reperfusion, according to the score standards in the following table, so as to evaluate the degree of nerve function impairment, wherein the total score is 16, the higher the score is, the more serious the degree of nerve function impairment is in the animal (Li Qian, Wang Qiujuan, Guo Qinglong, Protective effect of TQ0701-2 on cerebral ischemia reperfusion injury in rats [J]. CHINESE JOURNAL OF CLINICAL PHARMACOLOGY AND THERAPEUTICS, 2010, 15(1): 36-40.)

2.3.2 Effect on Infarction Percentage after 48 h.

The rat was decapitated and the brain was taken 48 h after reperfusion, and was quickly frozen. The brain was cut along the coronal plane to obtain a 2 mm-thick slice. The brain slice was put in 1% TTC stain solution, and stained at 37° C. in dark by incubation for 30 min. After fixing with 10% formaldehyde solution for 1 week, the digits and images were stored in computer by digital camera imaging system. The infarction area and the whole brain area were determined by Medical Microscopic image Compute-aided Analysis System (MIAS) of Image Center of Beihang University, and the cerebral infarction percentage was calculated (the percentage of the infarction area in the whole brain area).

Statistical Method

Data was processed by the statistical analysis software SPSS11.5, and the results were expressed by x±s, and mathematical statistics were performed by using t-test for normal distribution data and using rank-sum test for skewed distribution.

3. Experimental Result 3.1 Effect on Nerve Function Impairment 3.2 Effect on Cerebral Infarction Percentage 48 h after Reperfusion

TABLE 61

Effect of scutellarin aglycone on cerebral infarction percentage in ischemia/reperfusion rats ($\bar{x} \pm s$, n = 15)

| Group | Dose (mg/kg) | Cerebral infarction percentage (%) | Reducing rate (%) |
|---|---|---|---|
| Sham-operated group | 0.3% CMC-Na | 0.00 ± 0.00 | |
| Model control group | 0.3% CMC-Na | 15.92 ± 0.07▲▲ | |
| Scutellarin aglycone group | 45.8 | 9.16 ± 0.09* | 42.46 |

Note:
compared with the sham-operated group: ▲P < 0.05, ▲▲P < 0.01; compared with the model control group: *P < 0.05, **P < 0.01.

The experimental results show (Table 61): as compared to the model control group, seutellarin aglycone at a dose of 45.8 mg/kg could significantly reduce the cerebral infarction area in MCAO-induced ischemia-reperfusion rat, at a reducing rate of 42.46% (P<0.05).

Although the embodiments of the invention have been described in detail, a person skilled in the art would understand that according to all the disclosed teachings, the details can be amended and modified, and these alterations all fall into the protection scope of the invention. All the scope of the invention is defined by the attached claims and any equivalent thereof.

The invention claimed is:

1. Crystal form E of scutellarin aglycone, characterized in that said crystal form E has an X-ray powder diffraction pattern having main characteristic absorption peaks at least at about the following 2θ positions: 9.6±0.2°, 14.0±0.2°, 15.3±0.2°, 17.8±0.2° and 26.6±0.2°, as determined by using Cu—Kα radiation.

2. The crystal form E according to claim 1, characterized in that the X-ray powder diffraction pattern further has one or more characteristic absorption peaks at about 2θ position

TABLE 60

Effect of scutellarin aglycone on nerve function in ischemia/reperfusion rats ($\bar{x} \pm s$, n = 15)

| | | Behavior score at different time after reperfusion | | | | |
|---|---|---|---|---|---|---|
| Group | Dose (mg/kg) | 1 h | 12 h | 24 h | 36 h | 48 h |
| Sham-operated group | 0.3% CMC-Na | 0 | 0 | 0 | 0 | 0 |
| Model control group | 0.3% CMC-Na | 10.35 ± 2.3▲▲ | 9.64 ± 3.0▲▲ | 9.21 ± 3.7▲▲ | 9.14 ± 4.12▲▲ | 8.75 ± 4.24▲▲ |
| Scutellarin aglycone group | 45.8 | 10.57 ± 2.22 | 7.96 ± 2.29 | 7.15 ± 2.56 | 6.23 ± 2.87 | 5.69 ± 2.67* |

Note:
compared with the sham-operated group: ▲P < 0.05, ▲▲P < 0.01;
compared with the model control group: *P < 0.05, **P < 0.01.

The experimental result shows (Table 60): after the model rat was established by thread occlusion method, as compared with the sham-operated group, serious never function disorder appeared in the animals in each of the groups (P<0.01), which demonstrated that the model was successful. The never function disorder in the animals was significantly improved 48 h after administration of scutellarin aglycone at a dose of 45.8 mg/kg, which was of significance (P<0.05) as compared to the model control group, with an improvement rate of 34.97%.

selected from: 10.2±0.2°, 10.9±0.2°, 16.1±0.2°, 19.3±0.2°, 21.2±0.2°, 28.5±0.2°, 29.8±0.2°, 31.1±0.2°, etc., as determined by using Cu—Kα radiation.

3. The crystal form E according to claim 1, which has a melting point of about 364.0±3.0° C. as determined by differential scanning calorimetry.

4. A method for preparing the crystal form E according to claim 1, comprising the following steps of:
heating scutellarin aglycone solid to 250-350° C., and then naturally cooling it to room temperature, to obtain the crystal form E of scutellarin aglycone.

5. The crystal form E according to claim 1, which is an anhydrous substance.

6. A pharmaceutical composition, comprising the crystal form E according to claim 1 and a pharmaceutically acceptable carrier or excipient.

7. A method for treating cerebral infarction, comprising the step of administering to a subject in need thereof a therapeutically effective amount of the crystal form E according to claim 1.

* * * * *